United States Patent
Hsiau et al.

(10) Patent No.: US 11,970,733 B2
(45) Date of Patent: Apr. 30, 2024

(54) METHODS FOR ANALYZING NUCLEIC ACID SEQUENCES

(71) Applicant: Synthego Corporation, Redwood City, CA (US)

(72) Inventors: Timothy Hsiau, Hayward, CA (US); Richard Stoner, San Jose, CA (US); Travis Maures, Pacifica, CA (US); David Conant, San Francisco, CA (US)

(73) Assignee: Synthego Corporation, Redwood City, CA (US)

( * ) Notice: Subject to any disclaimer, the term of this patent is extended or adjusted under 35 U.S.C. 154(b) by 768 days.

(21) Appl. No.: 16/671,979

(22) Filed: Nov. 1, 2019

(65) Prior Publication Data

US 2020/0270680 A1    Aug. 27, 2020

Related U.S. Application Data

(60) Provisional application No. 62/754,451, filed on Nov. 1, 2018, provisional application No. 62/754,382, filed on Nov. 1, 2018.

(51) Int. Cl.
| | |
|---|---|
| *C12Q 1/6869* | (2018.01) |
| *B01L 3/00* | (2006.01) |
| *C12N 9/22* | (2006.01) |
| *C12N 15/113* | (2010.01) |
| *C12Q 1/6806* | (2018.01) |
| *C12Q 1/6853* | (2018.01) |
| *G01N 33/487* | (2006.01) |
| *G06F 17/18* | (2006.01) |

(52) U.S. Cl.
CPC .......... *C12Q 1/6869* (2013.01); *C12N 9/22* (2013.01); *C12N 15/113* (2013.01); *C12Q 1/6806* (2013.01); *C12Q 1/6853* (2013.01); *G01N 33/48721* (2013.01); *G06F 17/18* (2013.01); *B01L 3/502761* (2013.01); *B01L 2200/10* (2013.01); *C12N 2310/20* (2017.05); *C12Q 2563/116* (2013.01)

(58) Field of Classification Search
None
See application file for complete search history.

(56) References Cited

U.S. PATENT DOCUMENTS

| | | | |
|---|---|---|---|
| 8,697,359 B1 * | 4/2014 | Zhang | C12N 15/85 435/6.13 |
| 2012/0142051 A1 | 6/2012 | Ogawa et al. | |
| 2017/0198302 A1 | 7/2017 | Feng | |

FOREIGN PATENT DOCUMENTS

| | | |
|---|---|---|
| JP | 4243680 | 3/2009 |
| WO | 2014/093595 | 6/2014 |
| WO | 2018/067826 | 4/2018 |
| WO | WO-2019118948 A2 | 6/2019 |
| WO | 2019/204668 | 10/2019 |
| WO | WO-2020093025 A1 | 5/2020 |

OTHER PUBLICATIONS

Amir et al. Bacterial Community Reconstruction Using Compressed Sensing. V. Bafna and S.C. Sahinalp (Eds.): RECOMB 2011, LNBI 6577, pp. 1-15, 2011. Copyright Springer-Verlag Berlin Heidelberg 2011.

Brinkman et al. Easy quantification of template-directed CRISPR/Cas9 editing. Supplementary Data. Nucleic Acids Research 46(10):e58 (2018). Published online Mar. 10, 2018. doi: 10.1093/nar/gky164.

Brinkman et al. Easy quantification of template-directed CRISPR/Cas9 editing. Nucleic Acids Research 46(10):e58 (2018). Published online Mar. 10, 2018. doi: 10.1093/nar/gky164. 9 pages.

Brinkman et al. Easy quantitative assessment of genome editing by sequence trace decomposition. Nucleic Acids Research 42(22):e168 (Dec. 16, 2014). Published online Oct. 9, 2014.

Chang et al. Mixed Sequence Reader: A Program for Analyzing DNA Sequences with Heterozygous Base Calling. The Scientific World Journal, vol. 2012, Article ID 365401. Copyright 2012. doi:10.1100/2012/365104. 10 pages.

CRISPResso: Analysis of CRISPR-Cas9 genome editing outcomes from deep sequencing data. Retrieved Aug. 6, 2018 at URL: http://crispresso.rocks/help. 12 pages.

Dehairs et al. CRISP-ID: decoding CRISPR mediated indels by Sanger sequencing. Scientific Reports 6:28973 (Jul. 1, 2016). DOI: 10.1038/srep28973. 5 pages.

Hsiau et al.Inference of CRISPR Edits from Sanger Trace Data. Version 1. bioRxiv (Jan. 20, 2018). Retrieved from URL: https://www.biorxiv.org/content/10.1101/251082v1. 14 pages.

Hsiau et al.Inference of CRISPR Edits from Sanger Trace Data. Version 2. bioRxiv (published Jan. 20, 2018, updated Jan. 14, 2019). Retrieved from URL: https://www.biorxiv.org/content/10.1101/251082v2. 16 pages.

Hsiau et al.Inference of CRISPR Edits from Sanger Trace Data. Version 3. bioRxiv (published Jan. 20, 2018; updated Aug. 10, 2019). Retrieved from URL: https://www.biorxiv.org/content/10.1101/251082v3. 17 pages.

O'Geen et al. A genome-wide analysis of Cas9 binding specificity using ChIP-seq and targeted sequence capture. Nucleic Acids Research 43(6):3389-3404 (2015). Published online Feb. 20, 2015. doi: 10.1093/nar/gkv137.

(Continued)

*Primary Examiner* — Nancy J Leith
(74) *Attorney, Agent, or Firm* — Quarles & Brady, LLP

(57) ABSTRACT

The present disclosure provides a method for analyzing nucleic acid sequences. The method can comprise determining, by a computer system, a base trace by trimming a Sanger sequencing trace of a plurality of nucleic acid molecules from a sample based on a first target sequence and a second target sequence. Each of the first and second target sequences can be in the plurality of nucleic acid molecules or can be in the complement of sequence of the plurality of nucleic acid molecules.

18 Claims, 30 Drawing Sheets

Specification includes a Sequence Listing.

(56) References Cited

OTHER PUBLICATIONS

Pinello, et al. Analyzing CRISPR genome-editing experiments with CRISPResso. Nat Biotechnol. Jul. 12, 2016; 34(7): 695-697.
Poly Peak Parser. Retrieved Sep. 17, 2018 at URL: yosttools.genetics.utah.edu/PolyPeakParser. 4 pages.
Quality Scores for Next-Generation Sequencing. Illumina. Copyright 2011. 2 pages.
Shigemizu et al. IMSindel: An accurate intermediate-size indel detection tool incorporating de novo assembly and gapped global-local alignment with split read analysis. Scientific Reports 8:5608 (2018). Published online Apr. 4, 2018. DOI:10.1038/s41598-018-23978-z. 9 pages.
TIDE: Tracking of Indels by DEcomposition. Retrieved Sep. 13, 2018 at URL: https://tide.deskgen.com/. 4 pages.
Tider. Retrieved Sep. 13, 2018 at URL: https://tider.deskgen.com. 5 pages.
Zhidkov et al. CHILD: a new tool for detecting low-abundance insertions and deletions in standard sequence traces. Nucleic Acids Research 39(7):e47 (2011). Published online Jan. 28, 2011. 8 pages.
International Search Report and Written Opinion for International Patent Application No. PCT/US2019/059557, dated Feb. 20, 2020.

\* cited by examiner

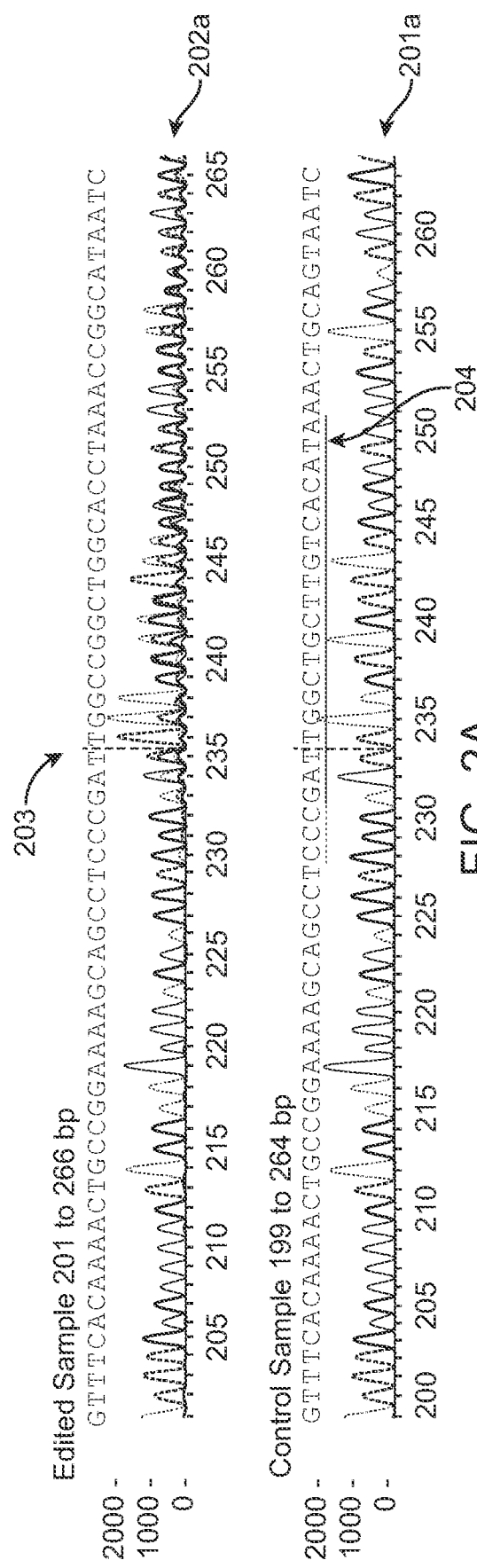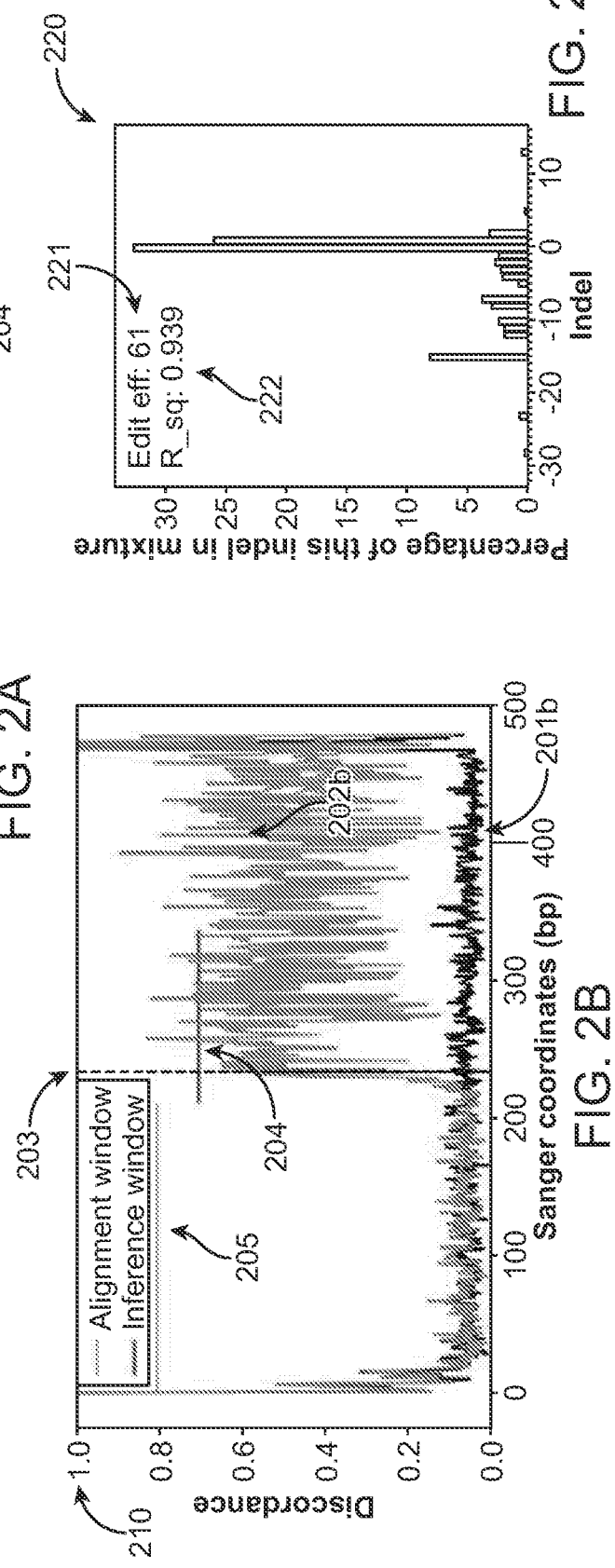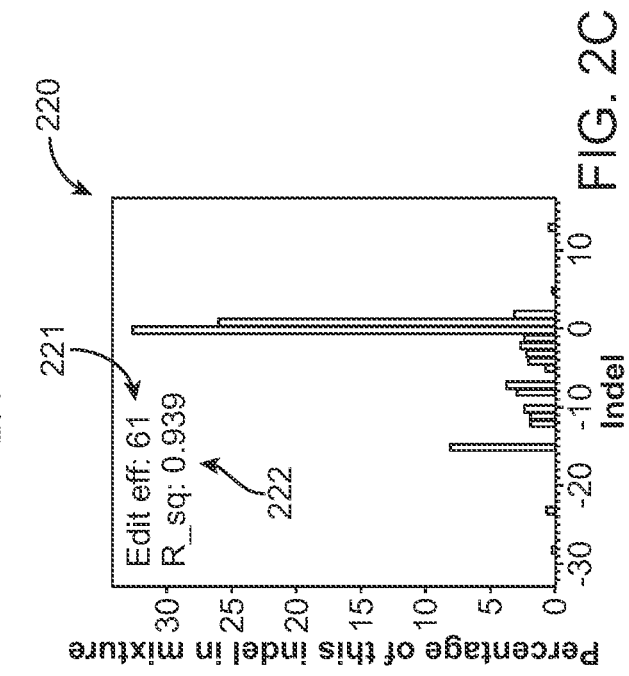
FIG. 2A
FIG. 2B
FIG. 2C

350 →

Edit proposal 1

51.7%  -51:md-0[g1],-0[g3]  ATTATCTGCTCTGTGCTTTGCAGGA
355 →  ----------|TCCTGGCCTTCTACTCCCAGGAGGTACGAGACCTGT ← 353
                                                        352

>G11_CG11_CONTIG_219_p1 24222 pairs of Amp-Seq reads, 40.5%
GGCTCTGTGTAAGACCATATTAGCCAAGTCTTTAGCCCCCGCTTGAAGTCTGTGGGGCAAGGAACCCAGCC
cagccagatgttctggccttgttctctgtccctgctagccctggctttgcccattatctgCTCTGTGCTT ← 356
TGCAGGAATCCTGGCCTTCTACTCCCAGGAGGTACGAGACCTGTTCCAGATGAAGCTTTTTGTGGA
                                                                      357

Edit proposal 2

9.8%  -30:md-0[g1],-0[g2]  CATTATCTGCTCTGTGCTTTGCAGGA
365 →  ----------|ACGTGGTGCTCTTTGAAGG ← 363
                                    362

>G11_CG11_CONTIG_240_p2 5977 pairs of Amp-Seq reads, 9.99%
GGCTCTGTGTAAGACCATATTAGCCAAGTCTTTAGCCCCCGCTTGAAGTCTGTGGGGCAAGGAACCCAGCC
CAGCCAGATGTTCTGGCCTTgttctctgtccctgctagccctggctttggcccattatctgCTCTGTGCTT ← 366
TGCAGGAACGTGGTGCTCTTTGAAGGATCCTGGCCTTCTACTCCCAGGAGGTACGAGACCTGTTCCAGATGAAGCT
TTTTGTGGA
         368

FIG. 3F

| | | | |
|---|---|---|---|
| -20 | 0.3% | CTTCATGATG----------- | ------GCTGCGGGCCACACGCTCCTCCGTCTCCAGCTTCTCGTACTT |
| +7 | 0.3% | CTTCATGATGATGTATGAGTCCGAAGATC | NNNNNNTCCCGGCCACACGCTCCTCCGTCTCCAGCTTCTCCAGCTTCT |
| -24 | 0.2% | CTTCATGATGATGTATGA--------- | ------CACACGCTCCTCCGTCTCCAGCTTCTCGTACTT |
| -30 | 0.2% | CTTCATGATG---------------- | ------ACACGCTCCTCCGTCTCCAGCTTCTCGTACTT |
| -7 | 0.2% | CTTCATGATGATGTATGAGTCCGAAGATC | -TGCGGGCCACACGCTCCTCCGTCTCCAGCTTCTCGTACTT |
| -23 | 0.2% | CTTCATGATGATGTATGA----- | -CCACACGCTCCTCCGTCTCCAGCTTCTCGTACTT |
| -16 | 0.1% | CTTCATGATGATGTATGAGTC--- | -CCCGGCTGCGGGCCACACGCTCCTCCGTCTCCAGCTTCTCGTACTT |
| -8 | 0.1% | CTTCATGATGATGTATGAGTC--- | -CCCGGCTGCGGGCCACACGCTCCTCCGTCTCCAGCTTCTCGTACTT |
| -8 | 0.1% | CTTCATGATGATGTATGAGTC--- | -CCCGGCTGCGGGCCACACGCTCCTCCGTCTCCAGCTTCTCGTACTT |
| -16 | 0.2% | CTTCATGATG-------------- | -CCCGGCTGCGGGCCACACGCTCCTCCGTCTCCAGCTTCTCGTACTT |
| -23 | 0.2% | CTTCATGATGA------------ | -CCCGGCTGCGGGCCACACGCTCCTCCGTCTCCAGCTTCTCGTACTT |
| -7 | 0.2% | CTTCATGATGATGTATGAGTCCGAAGATC | -TGCGGGCCACACGCTCCTCCGTCTCCAGCTTCTCGTACTT |
| -30 | 0.2% | CTTCATGATGATGTATGA---- | ------ACACGCTCCTCCGTCTCCAGCTTCTCGTACTT |
| -24 | 0.3% | CTTCATGATG-------------- | ------CACACGCTCCTCCGTCTCCAGCTTCTCGTACTT |
| +7 | 0.3% | CTTCATGATGATGTATGAGTCCGAAGATC | NNNNNNNTCCCGGCCACACGCTCCTCCGTCTCCAGCTTCT |
| -20 | 0.4% | CTTCATGATG----------- | ------GCTGCGGGCCACACGCTCCTCCGTCTCCAGCTTCTCGTACTT |
| -17 | 0.4% | CTTCATGATGA----------- | -CCCGGCTGCGGGCCACACGCTCCTCCGTCTCCAGCTTCTCGTACTT |
| -11 | 0.4% | CTTCATGATGATGTATGA----- | -CCCGGCTGCGGGCCACACGCTCCTCCGTCTCCAGCTTCTCGTACTT |
| -14 | 0.5% | CTTCATGATGATGTATGAGTCGAAGATC | -CACGCTCCTCCGTCTCCAGCTTCTCGTACTT |

← 630

→ 603 ⬇ DOWNLOAD ANALYSIS DATA

← 625

⬈ SHARE

FIG. 6A (Cont.)

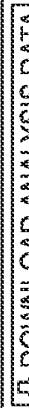
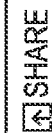
FIG. 8A (Cont.)

| Name | Type |
|---|---|
| ☐ 19bp_guide_PIK3CB_control.ab1 | AB1 File |
| ☐ 19bp_guide_PIK3CB_experiment.ab1 | AB1 File |
| ☐ high_edit_GRK2_control.ab1 | AB1 File |
| ☐ high_edit_GRK2_experiment.ab1 | AB1 File |
| ☐ knockin_control.ab1 | AB1 File |
| ☐ knockin_edited.ab1 | AB1 File |
| ☐ low_edit_PRKAG1_control.ab1 | AB1 File |
| ☐ low_edit_PRKAG1_experiment.ab1 | AB1 File |
| ☐ low_ko_RYK_control.ab1 | AB1 File |
| ☐ low_ko_RYK_experiment.ab1 | AB1 File |
| ☐ low_quality_DMPK_control.ab1 | AB1 File |
| ☐ low_quality_DMPK_experiment.ab1 | AB1 File |
| ☐ multiplex_AKT1_control.ab1 | AB1 File |
| ☐ multiplex_AKT1_experiment.ab1 | AB1 File |

FIG. 12A

SAMPLE BY SAMPLE UPLOAD | BATCH UPLOAD

AB1 FILES

Drop .zip file here or browse your files

*A ZIP archive containing your AB1 files.*

DEFINITION FILE

Drop .xlsx file here or browse your files

*An Excel spreadsheet with the definitions for the AB1 files.*

FIG. 11

| Label | Control File | Experiment File | Guide Sequence | Donor Sequence |
|---|---|---|---|---|
| Low Quality - DMPK | low_quality_DMPK_control.ab1 | low_quality_DMPK_experiment.ab1 | CAGCCGAGGTGCGGCTGAGG | |
| 19bp Guide - PIK3CB | 19bp_guide_PIK3CB_control.ab1 | 19bp_guide_PIK3CB_experiment.ab1 | UUGUUUGAACAGUUCCCAU | |
| High Edit - GRK2 | high_edit_GRK2_control.ab1 | high_edit_GRK2_experiment.ab1 | UGUAUGAGUCGAAGAUCUCC | |
| Low Edit - PRKAG | low_edit_PRKAG1_control.ab1 | low_edit_PRKAG1_experiment.ab1 | GGAAGUAUACACGCUAUUGU | |
| Multiplex - AKT1 | multiplex_AKT1_control.ab1 | multiplex_AKT1_experiment.ab1 | TGAAGGTGCCATCATTCTTG; TCACGTTGGTCCACATCCTG | |
| Low KO - RYK | low_ko_RYK_control.ab1 | low_ko_RYK_experiment.ab1 | AUGUAAGGCAAUAUCACCAU | |
| Knockin | knockin_control.ab1 | knockin_edited.ab1 | AAGTGCAGCTTCGTCCGGCGT | ATCCTCCCGGGAACGTCTCCA CCAGCTTCCCTTCCAGCCGAC GAGATTGATCTCCGACCCGAC GAGCTGCACTTCCTGTCCAAG CACTTCCGCAGCTCAGAGA |

FIG. 12B

SEQUENCE LISTING

<160> NUMBER OF SEQ ID NOS: 125

<210> SEQ ID NO 1
<211> LENGTH: 20
<212> TYPE: RNA
<213> ORGANISM: Unknown
<220> FEATURE:
<223> OTHER INFORMATION: Description of Unknown:
      Guide target sequence

<400> SEQUENCE: 1
gauucaaguc caagcaucau                                                  20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

```
ctggaagccg ccctgcagc                                              19

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gaagccgccc tgc                                                    13

<210> SEQ ID NO 4
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtttcacaaa actgccggaa aagcagcctc ccgattggcc ggctggcacc taaaccggca    60
taatc                                                              65

<210> SEQ ID NO 5
<211> LENGTH: 65
<212> TYPE: DNA
<213> ORGANISM: Homo sapiens

<400> SEQUENCE: 5
gtttcacaaa actgccggaa aagcagcctc ccgattggct gcttgtcaca taaactgcag    60
taatc                                                              65

<210> SEQ ID NO 6
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
attatctgct ctgtgctttg caggatcctg gccttctact cccaggaggt acgagacctg    60
t                                                                  61

<210> SEQ ID NO 7
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ggctctgtaa gaccatatta gccaagtctt tagcccccgc ttgaagtctg tgggggcaag    60
gaacccagaa cccagcccag ccagatgttc tggcccttgt tctctgtccc ttgctagccc   120
ctgcctggct tggcccatta tctgctctgt gctttgcagg atcctggcct tctactccca   180
ggaggtacga gacctgttcc agatgaagct ttttgtgga                         219

<210> SEQ ID NO 8
<211> LENGTH: 46
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cattatctgc tctgtgcttt gcaggaacgt ggtgctcttt gaaggg            46

<210> SEQ ID NO 9
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ggctctgtaa gaccatatta gccaagtctt tagcccccgc ttgaagtctg tggggggcaag     60 gaacccagaa cccagcccag ccagatgttc tggcccttgt tctctgtccc ttgctagccc    120
ctgcctggct tggcccatta tctgctctgt gctttgcagg aacgtggtgc tctttgaagg    180
gatcctggcc ttctactccc aggaggtacg agacctgttc cagatgaagc tttttgtgga    240

<210> SEQ ID NO 10
<211> LENGTH: 20
<212> TYPE: RNA
<213> ORGANISM: Unknown
<220> FEATURE:
<223> OTHER INFORMATION: Description of Unknown:
      Guide target sequence

<400> SEQUENCE: 10
uguaugaguc gaagaucucc                                         20

<210> SEQ ID NO 11
<211> LENGTH: 20
<212> TYPE: DNA
<213> ORGANISM: Unknown
<220> FEATURE:
<223> OTHER INFORMATION: Description of Unknown:
      Guide target sequence

<400> SEQUENCE: 11
tgtatgagtc gaagatctcc                                         20

<210> SEQ ID NO 12
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cttcatgatg tatgagtcga agatcccggc tgcgggccac acgctcctcc tccgtctcca    60
gcttctcgta ctt                                                73

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 13
cttcatgatg tatgagtcga agattcccgg ctgcgggcca cacgctcctc ctccgtctcc    60
agcttctcgt actt                                                     74

<210> SEQ ID NO 14
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cttcatgatg tatgagtcga agatccccgg ctgcgggcca cacgctcctc ctccgtctcc    60
agcttctcgt actt                                                     74

<210> SEQ ID NO 15
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a, c, t, g, unknown or other

<400> SEQUENCE: 15
cttcatgatg tatgagtcga agatcntccc ggctgcgggc cacacgctcc tcctccgtct    60
ccagcttctc gtact                                                    75

<210> SEQ ID NO 16
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cttcatgatg tatgagtcga agatccggct gcgggccaca cgctcctcct ccgtctccag    60
cttctcgtac tt                                                       72

<210> SEQ ID NO 17
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cttcatgatg tatgagtcga agatgcgggc cacacgctcc tcctccgtct ccagcttctc    60
gtactt                                                              66

<210> SEQ ID NO 18
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 18
cttcatgatg tatgagtcga agatctcccg gctgcgggcc acacgctcct cctccgtctc    60
cagcttctcg tactt                                                    75

<210> SEQ ID NO 19
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cttcatgatg tatgatcccg gctgcgggcc acacgctcct cctccgtctc cagcttctcg    60
tactt                                                               65

<210> SEQ ID NO 20
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cttcatgatg tatgagtcga ccggctgcgg gccacacgct cctcctccgt ctccagcttc    60
tcgtactt                                                            68

<210> SEQ ID NO 21
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cttcatgatg tatgagtcga agatgctgcg ggccacacgc tcctcctccg tctccagctt    60
ctcgtactt                                                           69

<210> SEQ ID NO 22
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cttcatgatg tatgagtcga agattgcggg ccacacgctc ctcctccgtc tccagcttct    60
cgtactt                                                             67

<210> SEQ ID NO 23
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cttcatgatg tatgagtcga agatcggctg cgggccacac gctcctcctc cgtctccagc    60
```
ttctcgtact t                                                          71

<210> SEQ ID NO 24
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, t, g, unknown or other

<400> SEQUENCE: 24
cttcatgatg tatgagtcga agatcnntcc cggctgcggg ccacacgctc ctcctccgtc     60
tccagcttct cgtac                                                      75

<210> SEQ ID NO 25
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cttcatgatg tatgagtcga agatcgctgc gggccacacg ctcctcctcc gtctccagct     60
tctcgtactt                                                            70

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cttcatgatg tatgagtcga agatcacacg ctcctcctcc gtctccagct tctcgtactt     60

<210> SEQ ID NO 27
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cttcatgatg tatgagtccc ggctgcgggc cacacgctcc tcctccgtct ccagcttctc     60
gtactt                                                                66

<210> SEQ ID NO 28
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cttcatgatg tatgagtcga agatccgggc cacacgctcc tcctccgtct ccagcttctc     60
gtactt                                                                66

<210> SEQ ID NO 29
<211> LENGTH: 69
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 29
cttcatgatg tatgagtcgt cccggctgcg ggccacacgc tcctcctccg tctccagctt    60
ctcgtactt                                                             69

<210> SEQ ID NO 30
<211> LENGTH: 61
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 30
cttcatgatg tatgagtcga agatccacac gctcctcctc cgtctccagc ttctcgtact    60
t                                                                     61

<210> SEQ ID NO 31
<211> LENGTH: 64
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 31
cttcatgatg tatgacccgg ctgcgggcca cacgctcctc ctccgtctcc agcttctcgt    60
actt                                                                  64

<210> SEQ ID NO 32
<211> LENGTH: 58
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 32
cttcatgatg ccggctgcgg gccacacgct cctcctccgt ctccagcttc tcgtactt      58

<210> SEQ ID NO 33
<211> LENGTH: 55
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 33
cttcatgatg gctgcgggcc acacgctcct cctccgtctc cagcttctcg tactt          55

<210> SEQ ID NO 34
<211> LENGTH: 75
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<221> NAME/KEY: modified_base
<222> LOCATION: (26)..(32)
<223> OTHER INFORMATION: a, c, t, g, unknown or other

<400> SEQUENCE: 34
cttcatgatg tatgagtcga agatcnnnnn nntcccggct gcgggccaca cgctcctcct      60
ccgtctccag cttct                                                      75

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cttcatgatg tatgacacac gctcctcctc cgtctccagc ttctcgtact t               51

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cttcatgatg acacgctcct cctccgtctc cagcttctcg tactt                     45

<210> SEQ ID NO 37
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cttcatgatg tatgagtcga agatctgcgg gccacacgct cctcctccgt ctccagcttc      60
tcgtactt                                                              68

<210> SEQ ID NO 38
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cttcatgatg tatgaccaca cgctcctcct ccgtctccag cttctcgtac tt              52

<210> SEQ ID NO 39
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cttcatgatg cccggctgcg ggccacacgc tcctcctccg tctccagctt ctcgtactt      59
```

```
<210> SEQ ID NO 40
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cttcatgatg tatgagtccc cggctgcggg ccacacgctc ctcctccgtc tccagcttct    60
cgtactt                                                              67

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cttcatgatg tatga                                                     15

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccacacgctc ctcctccgtc tccagcttct cgtactt                             37

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cttcatgatg tatgagtcga agatc                                          25

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gccacacgct cctcctccgt ctccagcttc tcgtactt                            38

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cttcatgatg                                                           10
```

```
<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acacgctcct cctccgtctc cagcttctcg tactt                              35

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cacacgctcc tcctccgtct ccagcttctc gtactt                             36

<210> SEQ ID NO 48
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccagcagctc cttcatgatg tatgagtcga agatcccggc tgcgggccac acgctcctcc   60
tccgtc                                                              66

<210> SEQ ID NO 49
<211> LENGTH: 66
<212> TYPE: DNA
<213> ORGANISM: Unknown
<220> FEATURE:
<223> OTHER INFORMATION: Description of Unknown:
      Control sample sequence

<400> SEQUENCE: 49
ccagcagctc cttcatgatg tatgagtcga agatctcccg gctgcgggcc acacgctcct   60
cctccg                                                              66

<210> SEQ ID NO 50
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other

<400> SEQUENCE: 50
tgtgaccaag agnnactaaa tcattcataa aagacctttt tgnnacgttt tcttatttta   60
gtttga                                                              66
```

```
<210> SEQ ID NO 51
<211> LENGTH: 66
<212> TYPE: DNA
<213> ORGANISM: Unknown
<220> FEATURE:
<223> OTHER INFORMATION: Description of Unknown:
      Control sample sequence

<400> SEQUENCE: 51
agctcatccc aggagcgcct ccgtgttctc ccctactttg ggggctgaga tgaaaggatt      60
ttctga                                                                66

<210> SEQ ID NO 52
<211> LENGTH: 20
<212> TYPE: DNA
<213> ORGANISM: Unknown
<220> FEATURE:
<223> OTHER INFORMATION: Description of Unknown:
      Guide target sequence

<400> SEQUENCE: 52
tgaaggtgcc atcattcttg                                                 20

<210> SEQ ID NO 53
<211> LENGTH: 20
<212> TYPE: DNA
<213> ORGANISM: Unknown
<220> FEATURE:
<223> OTHER INFORMATION: Description of Unknown:
      Guide target sequence

<400> SEQUENCE: 53
tcacgttggt ccacatcctg                                                 20

<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggcggccacg ctacttcctc ctcaagatgt ggaccaacgt gaggctcccc                 50

<210> SEQ ID NO 55
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggcggccacg ctacttcctc ctcaagaatg atggcacctt cattggctac aaggagcggc      60
cgcaggatgt ggacc                                                      75

<210> SEQ ID NO 56
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (25)..(25)
<223> OTHER INFORMATION: a, c, t, g, unknown or other

<400> SEQUENCE: 56
gcggccacgc tacttcctcc tcaangatgt ggaccaacgt gaggctcccc                50

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cattggctac aaggagcggc cgcaggaggc tcccctcaac aacttctctg tggcgcgtaa    60

<210> SEQ ID NO 58
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, t, g, unknown or other

<400> SEQUENCE: 58
cattggctac aaggagcggc cgcagnngat gtggaccaac gtgaggctcc cctcaacaac    60
ttctctgtgg cgcgt                                                     75

<210> SEQ ID NO 59
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cattggctac aaggaggtgg accaacgtga ggctcccctc aacaacttct ctgtggcgcg    60
taa                                                                  63

<210> SEQ ID NO 60
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a, c, t, g, unknown or other

<400> SEQUENCE: 60
cattggctac aaggagcggc cgcagngatg tggaccaacg tgaggctccc ctcaacaact    60
tctctgtggc gcgta                                                     75

<210> SEQ ID NO 61
<211> LENGTH: 59
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 61
cattggctac aaggagacca acgtgaggct cccctcaaca acttctctgt ggcgcgtaa      59

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cattggctac aaggaggacc aacgtgaggc tccctcaac aacttctctg tggcgcgtaa      60

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cattggctac gaggctcccc tcaacaactt ctctgtggcg cgtaa                    45

<210> SEQ ID NO 64
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cattggctac aaggagcggc cgcagatgtg gaccaacgtg aggctcccct caacaacttc    60
tctgtggcgc gtaa                                                      74

<210> SEQ ID NO 65
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggcggccacg ctacgaatga tggcaccttc attggctaca aggagcggcc gcaggatgtg    60
gacc                                                                 64

<210> SEQ ID NO 66
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cattggctac aaggagcggc cgatgtggac caacgtgagg ctcccctcaa caacttctct    60
gtggcgcgta a                                                         71

```
<210> SEQ ID NO 67
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cattggctac aaggagcggc cgcagcgtga ggctcccctc aacaacttct ctgtggcgcg    60
taa                                                                  63

<210> SEQ ID NO 68
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other

<400> SEQUENCE: 68
cggccacgct acttcctcct caanngaatg atggcacctt cattggctac aaggagcggc    60
cgcagngatg tggaccaacg tgaggctccc c                                   91

<210> SEQ ID NO 69
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cattggctac gatgtggacc aacgtgaggc tcccctcaac aacttctctg tggcgcgtaa    60

<210> SEQ ID NO 70
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(28)
<223> OTHER INFORMATION: a, c, t, g, unknown or other

<400> SEQUENCE: 70
cattggctac aaggagcggc cgcagnnnga tgtggaccaa cgtgaggctc ccctcaacaa    60
cttctctgtg gcgcg                                                     75

<210> SEQ ID NO 71
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
```
ggcggccacg atgatggcac cttcattggc tacaaggagc ggccgcagga tgtggacc    58

<210> SEQ ID NO 72
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cattggctac aaggagcggc cgcagtgtgg accaacgtga ggctcccctc aacaacttct    60
ctgtggcgcg taa    73

<210> SEQ ID NO 73
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cattggctac aaggagatgt ggaccaacgt gaggctcccc tcaacaactt ctctgtggcg    60
cgtaa    65

<210> SEQ ID NO 74
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ggcggccacg ctacttcctc ctgaatgatg gcaccttcat tggctacaag gagcggccga    60
tgtggaccaa cgtgaggctc ccc    83

<210> SEQ ID NO 75
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: a, c, t, g, unknown or other

<400> SEQUENCE: 75
cggccacgct acttcctcct caanngatgt ggaccaacgt gaggctcccc    50

<210> SEQ ID NO 76
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(29)
<223> OTHER INFORMATION: a, c, t, g, unknown or other

<400> SEQUENCE: 76

```
ggcggccacg ctacttcctc ctcaannnng aatgatggca ccttcattgg ctacaaggag      60
cggccgcagg atgtg                                                      75

<210> SEQ ID NO 77
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cattggctac aaggagcggg accaacgtga ggctcccctc aacaacttct ctgtggcgcg      60
taa                                                                   63

<210> SEQ ID NO 78
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cattggctac aaggagcggg atgtggacca acgtgaggct cccctcaaca acttctctgt      60
ggcgcgtaa                                                             69

<210> SEQ ID NO 79
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cattggctac aaggagcgga tgtggaccaa cgtgaggctc cctcaacaa cttctctgtg      60 gcgcgtaa                                                              68

<210> SEQ ID NO 80
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cattggctac cgtgaggctc ccctcaacaa cttctctgtg gcgcgtaa                  48

<210> SEQ ID NO 81
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cattggctac aaggagcgtg aggctcccct caacaacttc tctgtggcgc gtaa           54

<210> SEQ ID NO 82
<211> LENGTH: 17
```

```
<212> TYPE: DNA
<213> ORGANISM: Unknown
<220> FEATURE:
<223> OTHER INFORMATION: Description of Unknown:
      Guide target sequence

<400> SEQUENCE: 82
tcacgttggt ccacatc                                                    17

<210> SEQ ID NO 83
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
atcaagacct ggcggccacg ctacttcctc ctcaagatgt ggaccaacgt gaggctcccc    60
tcaaca                                                                66

<210> SEQ ID NO 84
<211> LENGTH: 22
<212> TYPE: DNA
<213> ORGANISM: Unknown
<220> FEATURE:
<223> OTHER INFORMATION: Description of Unknown:
      Control sample sequence

<400> SEQUENCE: 84
atcaagacct ggcggccacg ct                                              22

<210> SEQ ID NO 85
<211> LENGTH: 24
<212> TYPE: DNA
<213> ORGANISM: Unknown
<220> FEATURE:
<223> OTHER INFORMATION: Description of Unknown:
      Control sample sequence

<400> SEQUENCE: 85
cctcaagaat gatggcacct tcat                                            24

<210> SEQ ID NO 86
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggaccaacgt gaggctcccc tcaacaactt ctctgtggcg cgtaagtatc cccttggcct    60
ctcggg                                                                66

<210> SEQ ID NO 87
<211> LENGTH: 22
<212> TYPE: DNA
<213> ORGANISM: Unknown
<220> FEATURE:
<223> OTHER INFORMATION: Description of Unknown:
      Control sample sequence

<400> SEQUENCE: 87
atggcacctt cattggctac aa                                              22
```

```
<210> SEQ ID NO 88
<211> LENGTH: 23
<212> TYPE: DNA
<213> ORGANISM: Unknown
<220> FEATURE:
<223> OTHER INFORMATION: Description of Unknown:
      Control sample sequence

<400> SEQUENCE: 88
ccgcaggatg tggaccaacg tga                                          23

<210> SEQ ID NO 89
<211> LENGTH: 20
<212> TYPE: DNA
<213> ORGANISM: Unknown
<220> FEATURE:
<223> OTHER INFORMATION: Description of Unknown:
      Guide target sequence

<400> SEQUENCE: 89
aagtgcagct cgtccggcgt                                              20

<210> SEQ ID NO 90
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
atcctcccgg gaacgtctcc accagcttcc cttccagccg acgagattga tctccgaccc   60
gacgagctgc actt                                                    74

<210> SEQ ID NO 91
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ccaccagctt cccttccagc cgacgagatt gatctccgac ccgacgagct gcacttcctg   60
tccaagcact ccgc                                                    75

<210> SEQ ID NO 92
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ccaccagctt cccttccagc cgacgagctg cacttcctgt ccaagcactt ccgcagctca   60
gagaatgt                                                           68

<210> SEQ ID NO 93
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<221> NAME/KEY: modified_base
<222> LOCATION: (26)..(26)
<223> OTHER INFORMATION: a, c, t, g, unknown or other

<400> SEQUENCE: 93
ccaccagctt cccttccagc cgacgnccgg acgagctgca cttcctgtcc aagcacttcc    60
gcagctcaga gaatg                                                    75

<210> SEQ ID NO 94
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ccaccagctt cccttccagc cggacgagct gcacttcctg tccaagcact tccgcagctc    60
agagaatgt                                                           69

<210> SEQ ID NO 95
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccaccagctt cccttccagc cgacgccgga cgagctgcac ttcctgtcca agcacttccg    60
cagctcagag aatgt                                                    75

<210> SEQ ID NO 96
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ccaccagctt cccttccagc cgaacgagct gcacttcctg tccaagcact tccgcagctc    60
agagaatgt                                                           69

<210> SEQ ID NO 97
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ccaccagctt cccttccagc cgacggacga gctgcacttc ctgtccaagc acttccgcag    60
ctcagagaat gt                                                       72

<210> SEQ ID NO 98
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 98
ccaccagctt ccctccagc cgacctgcac ttcctgtcca agcacttccg cagctcagag      60
aatgt                                                                 65

<210> SEQ ID NO 99
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccaccagctt ccctccagc cgacggagct gcacttcctg tccaagcact tccgcagctc      60
agagaatgt                                                             69

<210> SEQ ID NO 100
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccaccagctt ccctccagc cgacgcgagc tgcacttcct gtccaagcac ttccgcagct      60
cagagaatgt                                                            70

<210> SEQ ID NO 101
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccaccagctt ccctccagc cgacgggacg agctgcactt cctgtccaag cacttccgca      60
gctcagagaa tgt                                                        73

<210> SEQ ID NO 102
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(33)
<223> OTHER INFORMATION: a, c, t, g, unknown or other

<400> SEQUENCE: 102
ccaccagctt ccctccagc cgacgnnnnn nnccggacg agctgcactt cctgtccaag       60
cacttccgca gctca                                                      75

<210> SEQ ID NO 103
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<221> NAME/KEY: modified_base
<222> LOCATION: (26)..(38)
<223> OTHER INFORMATION: a, c, t, g, unknown or other

<400> SEQUENCE: 103
ccaccagctt cccttccagc cgacgnnnnn nnnnnnnncc ggacgagctg cacttcctgt     60
ccaagcactt ccgca                                                     75

<210> SEQ ID NO 104
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ccaccagctt cccttccagc cgacccggac gagctgcact tcctgtccaa gcacttccgc     60
agctcagaga atgt                                                      74

<210> SEQ ID NO 105
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(36)
<223> OTHER INFORMATION: a, c, t, g, unknown or other

<400> SEQUENCE: 105
ccaccagctt cccttccagc cgacgnnnnn nnnnnccgg acgagctgca cttcctgtcc      60
aagcacttcc gcagc                                                     75

<210> SEQ ID NO 106
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, t, g, unknown or other

<400> SEQUENCE: 106
ccaccagctt cccttccagc cgacgnnccg gacgagctgc acttcctgtc caagcacttc     60
cgcagctcag agaat                                                     75

<210> SEQ ID NO 107
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(40)
<223> OTHER INFORMATION: a, c, t, g, unknown or other

<400> SEQUENCE: 107

```
ccaccagctt cccttccagc cgacgnnnnn nnnnnnnnnn ccggacgagc tgcacttcct    60
gtccaagcac ttccg                                                    75
```

<210> SEQ ID NO 108
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

```
ccaccagctt cccttccagc cccggacgag ctgcacttcc tgtccaagca cttccgcagc    60
tcagagaatg t                                                        71
```

<210> SEQ ID NO 109
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109

```
ccaccagctt cccttccagc cgagctgcac ttcctgtcca agcacttccg cagctcagag    60
aatgt                                                               65
```

<210> SEQ ID NO 110
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110

```
ccaccagctt cccttccttc ctgtccaagc acttccgcag ctcagagaat gt            52
```

<210> SEQ ID NO 111
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111

```
ccaccagctt cccttccagc ccgagctgca cttcctgtcc aagcacttcc gcagctcaga    60
gaatgt                                                              66
```

<210> SEQ ID NO 112
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112

```
ccaccagctt cccttccagc cgacgcggac gagctgcact tcctgtccaa gcacttccgc    60
agctcagaga atgt                                                     74
```

<210> SEQ ID NO 113

<210> SEQ ID NO 113
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ccaccagctt cccttccagc cgacggctgc acttcctgtc caagcacttc cgcagctcag    60
agaatgt                                                              67

<210> SEQ ID NO 114
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ccaccagctt cccttcccgg acgagctgca cttcctgtcc aagcacttcc gcagctcaga    60
gaatgt                                                               66

<210> SEQ ID NO 115
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ccaccagctt cccttccagc ttcctgtcca agcacttccg cagctcagag aatgt         55

<210> SEQ ID NO 116
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ccagcttccc ttccagccga cgagattgat ctccgacccg acgagctgca cttcctgtcc    60
aagcacttcc                                                           70

<210> SEQ ID NO 117
<211> LENGTH: 56
<212> TYPE: DNA
<213> ORGANISM: Unknown
<220> FEATURE:
<223> OTHER INFORMATION: Description of Unknown:
      Control sample sequence

<400> SEQUENCE: 117
ccagcttccc ttccagccga cgccggacga gctgcacttc ctgtccaagc acttcc        56

<210> SEQ ID NO 118
<211> LENGTH: 20
<212> TYPE: DNA
<213> ORGANISM: Unknown
<220> FEATURE:
<223> OTHER INFORMATION: Description of Unknown:
      Guide target sequence

<400> SEQUENCE: 118

```
cagccgaggt gcggctgagg                                              20

<210> SEQ ID NO 119
<211> LENGTH: 19
<212> TYPE: RNA
<213> ORGANISM: Unknown
<220> FEATURE:
<223> OTHER INFORMATION: Description of Unknown:
      Guide target sequence

<400> SEQUENCE: 119
uuguuugaac aguucccau                                               19

<210> SEQ ID NO 120
<211> LENGTH: 20
<212> TYPE: RNA
<213> ORGANISM: Unknown
<220> FEATURE:
<223> OTHER INFORMATION: Description of Unknown:
      Guide target sequence

<400> SEQUENCE: 120
ggaaguauac acgcuauugu                                              20

<210> SEQ ID NO 121
<211> LENGTH: 20
<212> TYPE: RNA
<213> ORGANISM: Unknown
<220> FEATURE:
<223> OTHER INFORMATION: Description of Unknown:
      Guide target sequence

<400> SEQUENCE: 121
auguaaggca auaucaccau                                              20

<210> SEQ ID NO 122
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
atcctcccgg gaacgtctcc accagcttcc cttccagccg acgagattga tctccgaccc    60
gacgagctgc acttcctgtc caagcacttc cgcagctcag aga                    103

<210> SEQ ID NO 123
<211> LENGTH: 20
<212> TYPE: DNA
<213> ORGANISM: Unknown
<220> FEATURE:
<223> OTHER INFORMATION: Description of Unknown:
      Guide target sequence

<400> SEQUENCE: 123
ggaagtatac acgctattgt                                              20

<210> SEQ ID NO 124
<211> LENGTH: 19
<212> TYPE: DNA
<213> ORGANISM: Unknown
<220> FEATURE:
<223> OTHER INFORMATION: Description of Unknown:
      Guide target sequence
```

```
<400> SEQUENCE: 124
ttgtttgaac agttcccat                                           19

<210> SEQ ID NO 125
<211> LENGTH: 20
<212> TYPE: DNA
<213> ORGANISM: Unknown
<220> FEATURE:
<223> OTHER INFORMATION: Description of Unknown:
      Guide target sequence

<400> SEQUENCE: 125
atgtaaggca atatcaccat                                          20
```

METHODS FOR ANALYZING NUCLEIC ACID SEQUENCES

CROSS-REFERENCE

This application claims the benefit of U.S. Patent Application No. 62/754,382, filed Nov. 1, 2018, and U.S. Patent Application No. 62/754,451, filed Nov. 1, 2018, each of which is incorporated herein by reference in its entirety. The subject matter of this application relates to the patent application titled "METHODS FOR KNOCK-OUT OF A TARGET SEQUENCE THROUGH INTRODUCTION OF A PREMATURE STOP CODON", and filed on even date herewith. The aforementioned application is incorporated herein by reference.

SEQUENCE LISTING

The instant application contains a Sequence Listing which has been filed electronically in ASCII format and is hereby incorporated by reference in its entirety. Said ASCII copy, created on Mar. 6, 2020, is named 54108-718_201_SL.txt and is 36,937 bytes in size.

BACKGROUND

Engineered nuclease technologies designed to target and manipulate specific nucleic acid sequences are rapidly being adopted as useful techniques for a number of different applications including genetic manipulation of cells and whole organisms, targeted gene deletion, replacement and repair, and insertion of exogenous sequences (e.g., transgenes) into the genome. Examples of nucleic acid editing tools include zinc finger nucleases, transcription activator-like effector (TALE) nucleases, and clustered regularly interspaced short palindromic repeats (CRISPR)/CRISPR-associated (Cas) ("CRISPR/Cas") systems.

In an example, the CRISPR/Cas system can be used as a nucleic acid editing tool in a plethora of different organisms in order to generate breaks at a target site and subsequently introduce altered sequence. At least two components can be used for nucleic acid editing: an endonuclease (e.g., Cas9 and Cpf1) and a short nucleic acid molecule (e.g., a customizable short RNA molecule, such as a guide RNA (gRNA)) that can be used to recruit the endonuclease to a specific nucleic acid target sequence. The CRISPR/Cas system can be used in prokaryotic and eukaryotic systems for genome editing.

Subsequent to nucleic acid editing (e.g., genome editing), nucleic acids from a single cell or a population of cells (or amplified products thereof, e.g., polymerase chain reaction (PCR) products)) can be analyzed by a massive parallel sequencing (i.e., next-generation sequencing (NGS)) technique to assess nucleic acid editing outcomes. For example, the massive parallel sequencing technique can detect one or more insertions and/or deletions ("indels") that are present in edited nucleic acids of the single cell or the population of cells. In some cases, the massive parallel sequencing technique can be costly and/or time consuming. In some cases, the massive parallel sequencing technique cannot be readily available. There is a need for improved methods for assessing nucleic acid editing outcomes.

SUMMARY

The present disclosure describes technologies relating to characterizing nucleic acid editing (e.g., by engineered endonucleases), and more specifically, the present disclosure describes methods of generating a plurality of predicted mutated sequencing traces of an unedited sequencing trace of a nucleic acid to deduce a nucleic acid editing outcome. The present disclosure describes systems and methods for performing the design and analysis of such plurality of predicted mutated sequencing traces.

In an aspect, the present disclosure provides a method comprising determining, by a computer system, a plurality of predicted sequences of individual nucleic acid molecules in a sample contacted by at least two different nucleic acid editing tools based on a Sanger sequencing trace of a plurality of nucleic acid molecules from the sample contacted by the at least two different nucleic acid editing tools.

The determining can be further based on an additional Sanger sequencing trace of a plurality of nucleic acid molecules from an additional sample not contacted by a nucleic acid editing tool. The determining can be further based on at least two different guide sequences of the at least two different nucleic acid editing tools.

The method can further comprise determining a base trace by trimming the additional Sanger sequencing trace based on the at least two different guide sequences. The trimming can comprise subtracting a portion of the additional Sanger sequencing trace disposed between (i) a predicted cut site operatively coupled to a first guide sequence of the at least two different guide sequences and (ii) an additional predicted cut site operatively coupled to a second guide sequence of the at least two different guide sequences.

The method can further comprise identifying a subset of the plurality of predicted sequences by performing a regression analysis. The regression analysis can comprise a non-negative least squares regression analysis or a regularized regression analysis. An R-squared value of the regression analysis is at least 0.5, 0.55, 0.6, 0.65, 0.7, 0.75, 0.8, 0.85, 0.9, or 0.95. The method can further comprise reporting to a user a predicted sequence of the subset and a frequency of the predicted sequence in the subset.

An individual nucleic acid editing tool of the at least two different nucleic acid editing tools can comprise a CRISPR/Cas complex.

In another aspect, the present disclosure provides a computer program product comprising a non-transitory computer-readable medium having computer-executable code encoded therein, the computer-executable code adapted to be executed to implement any one of the subject methods for determining a plurality of predicted sequences of individual nucleic acid molecules in a sample contacted by at least two different nucleic acid editing tools based on a Sanger sequencing trace of a plurality of nucleic acid molecules from the sample contacted by the at least two different nucleic acid editing tools. In another aspect, the present disclosure provides a computer system comprising one or more processors to execute the computer program product.

In an aspect, the present disclosure provides a method comprising determining, by a computer system, a plurality of predicted sequences of individual nucleic acid molecules in a sample contacted by at least two different CRISPR/Cas complexes based on (i) at least two different guide sequences of the at least two different CRISPR/Cas complexes and (ii) a control Sanger sequencing trace of a plurality of nucleic acid molecules from a control sample not contacted by a CRISPR/Cas complex.

The determining can be further based on a Sanger sequencing trace of a plurality of nucleic acid molecules from the sample contacted by the at least two different CRISPR/Cas complexes.

The method can further comprise determining a base trace by trimming the control Sanger sequencing trace based on the at least two different guide sequences. The trimming can comprise subtracting a portion of the control Sanger sequencing trace disposed between (i) a predicted cut site of a CRISPR/Cas complex of the at least two different CRISPR/Cas complexes and (ii) an additional predicted cut site of an additional CRISPR/Cas complex of the at least two different CRISPR/Cas complexes.

The method can further comprise identifying a subset of the plurality of predicted sequences by performing a regression analysis. The regression analysis can comprise a non-negative least squares regression analysis or a regularized regression analysis. An R-squared value of the regression analysis is at least 0.5, 0.55, 0.6, 0.65, 0.7, 0.75, 0.8, 0.85, 0.9, or 0.95. The method can further comprise reporting to a user a predicted sequence of the subset and a frequency of the predicted sequence in the subset.

In another aspect, the present disclosure provides a computer program product comprising a non-transitory computer-readable medium having computer-executable code encoded therein, the computer-executable code adapted to be executed to implement any of the subject methods for determining a plurality of predicted sequences of individual nucleic acid molecules in a sample contacted by at least two different CRISPR/Cas complexes based on (i) at least two different guide sequences of the at least two different CRISPR/Cas complexes and (ii) a control Sanger sequencing trace of a plurality of nucleic acid molecules from a control sample not contacted by a CRISPR/Cas complex. In another aspect, the present disclosure provides a computer system comprising one or more processors to execute the computer program product.

In an aspect, the present disclosure provides a method comprising determining, by a computer system, a base trace by trimming a Sanger sequencing trace of a plurality of nucleic acid molecules from a sample based on a first target sequence and a second target sequence, wherein each of the first and second target sequences is in the plurality of nucleic acid molecules, or is in the complement of sequence of the plurality of nucleic acid molecules.

The trimming can comprise subtracting a portion of the Sanger sequencing trace disposed between a first predicted cut site of a nucleic acid editing tool in the first target sequence and a second predicted cut site of the nucleic acid editing tool in the second target sequence. The nucleic acid editing tool can comprise a nuclease.

The method can further comprise obtaining an additional Sanger sequencing trace of an additional plurality of nucleic acid molecules from an additional sample, wherein the sample and the additional sample are different. The additional plurality of nucleic acid molecules can comprise nucleic acid molecules contacted with the nucleic acid editing tool. The nucleic acid editing tool may not have contacted the plurality of nucleic acid molecules.

The method can further comprise generating an initial set of predicted sequences of individual nucleic acid molecules based on the base trace. The initial set of predicted sequences of individual nucleic acid molecules can comprise insertions or deletions. The insertions or deletions can be adjacent to the first and second predicted cut sites.

The determining can comprise comparing the initial set of predicted sequences of individual nucleic acid molecules to the additional Sanger sequencing trace of the additional plurality of nucleic acid molecules from the additional sample. The comparing can comprise identifying a subset of the initial set of predicted sequences of individual nucleic acid molecules by performing a regression analysis.

The regression analysis can comprise a non-negative least squares regression analysis or a regularized regression analysis (e.g., a Lasso regression analysis). The regression analysis can identify sequences of the initial set of predicted sequences of individual molecules, wherein the identified sequences in combination resemble the first Sanger sequencing trace. An R-squared value of the regression analysis can be at least 0.5, 0.55, 0.6, 0.65, 0.7, 0.75, 0.8, 0.85, 0.9, or 0.95.

The method can further comprise reporting to a user a predicted sequence and a frequency of the predicted sequence in the subset of the initial set. The frequency of the predicted sequence can comprise a relative amount of the predicted sequence relative to other predicted sequences.

The Sanger sequencing trace or the additional Sanger sequencing trace can be from capillary electrophoresis. The Sanger sequencing trace or the additional Sanger sequencing trace can comprise a single electropherogram.

The first target sequence can comprise a first guide RNA sequence for CRISPR/Cas, or a complement of the first guide RNA sequence for CRISPR/Cas. The second target sequence can comprise a second guide RNA sequence for CRISPR/Cas, or a complement of the second guide RNA sequence for CRISPR/Cas.

The nucleic acid editing tool can comprise CRISPR/Cas. The nucleic acid editing tool can comprise a CRISPR/Cas comprising a single guide RNA.

The initial set of predicted sequences can include at least 1, 10, 100, 1,000, 10,000, or 100,000 predicted sequences.

The determining can comprise identifying an alignment window in the Sanger sequencing trace. The alignment window can comprise at least three nucleotides. The alignment window can be 5' of the first predicted cut site in the first target sequence. The alignment window can have an average Phred quality score of at least about 15, 20, 25, or 30. The first predicted cut site can be upstream of the second predicted cut site in the Sanger sequencing trace.

The determining can comprise aligning the Sanger sequencing trace and the base trace to the alignment window. A 3' end of the alignment window can be about 5, 10, 15, 20, or 25 nucleotides 5' of the first predicted cut site in the target sequence. The alignment window can comprise at least 10, 25, 50, 100, 150, or 200 nucleotides.

The determining can comprise identifying an inference window comprising the first and second predicted cut sites in the Sanger sequencing trace, wherein (i) a 5' end of the inference window is at about 10 to about 50 nucleotides 5' of the first predicted cut site and (ii) a 3' end of the inference window at about 10 to about 200 nucleotides 3' of the second predicted cut site. The 5' end of the inference window can be at 25 nucleotides 5' of the first predicted cut site in the target sequence. The 3' end of the inference window can be at 100 nucleotides 3' of the second predicted cut site in the target sequence. The identifying the inference window can comprise trimming the inference window based on a quality score of the Sanger sequence trace. The inference window can comprise an average Phred quality score of at least 15, 20, 25, or 30. The inference window can be determined automatically without a human intervention.

The method can further comprise performing a regression analysis between the initial set of predicted sequences and the additional Sanger sequencing trace at the inference window, thereby identifying a subset of predicted sequences from the initial set, wherein the identified subset of resembles the additional Sanger sequencing trace.

The first plurality of nucleic acid molecules and the second plurality of nucleic acid molecules can be from a same cell type. The initial set can further comprise an additional set of predicted sequences of individual nucleic acid molecules based on the Sanger sequencing trace. The additional set of predicted sequences of individual nucleic acid molecules can comprise insertions or deletions adjacent to the first predicted cut site. The additional set of predicted sequences of individual nucleic acid molecules can comprise insertions or deletions adjacent to the second predicted cut site.

In another aspect, the present disclosure provides a computer program product comprising a non-transitory computer-readable medium having computer-executable code encoded therein, the computer-executable code adapted to be executed to implement any one of the subject methods for determining a base trace by trimming a Sanger sequencing trace of a plurality of nucleic acid molecules from a sample based on a first target sequence and a second target sequence, wherein each of the first and second target sequences is in the plurality of nucleic acid molecules, or is in the complement of sequence of the plurality of nucleic acid molecules. In another aspect, the present disclosure provides a computer system comprising one or more processors to execute the computer program product.

In an aspect, the present disclosure provides a method comprising determining, by a computer system, a predicted knockout sequence of a single nucleic acid molecule based on a first Sanger sequencing trace and a second Sanger sequencing trace, wherein the predicted knockout sequence comprises an indel when compared to the second Sanger sequencing trace, and wherein the indel of the predicted knockout sequence is not a multiple of three nucleotides and/or longer than a threshold length.

The threshold length of the indel can be at least 10, 11, 12, 13, 14, 15, 16, 17, 18, 19, 20, 21, 22, 23, 24, or 25 nucleotides. The first Sanger sequencing trace can be from a first plurality of nucleic acid molecules from a first sample, wherein the second Sanger sequencing trace can be from a second plurality of nucleic acid molecules from a second sample, and wherein the first sample and second sample can be different.

The first plurality of nucleic acid molecules can comprise nucleic acid molecules contacted with a nucleic acid editing tool. The nucleic acid editing tool can comprise a nuclease. The nucleic acid editing tool may not have contacted the second plurality of nucleic acid molecules.

The determining can comprise obtaining a first target sequence, wherein the target sequence is in the second plurality of nucleic acid molecules or is in the complement of sequence of the second plurality of nucleic acid molecules.

The determining can comprise generating an initial set of predicted sequences of individual nucleic acid molecules based on the second Sanger sequencing trace, wherein the initial set comprises the predicted knockout sequence. The initial set of predicted sequences of individual nucleic acid molecules can comprise insertions or deletions relative to the first target sequence. The insertions or deletions can be adjacent to a site in the first target sequence predicted to be cut by the nucleic acid editing tool.

The determining can comprise comparing the initial set of predicted sequences of individual nucleic acid molecules to the first Sanger sequencing trace of the first plurality of nucleic acid molecules from the first sample. The comparing can comprise identifying a subset of the initial set of predicted sequences of individual nucleic acid molecules by performing a regression analysis. The regression analysis can comprise a non-negative least squares regression analysis or a regularized regression analysis (e.g., a Lasso regression analysis). The regression analysis can identify sequences of the initial set of predicted sequences of individual molecules, wherein the identified sequences in combination resemble the first Sanger sequencing trace. An R-squared value of the regression analysis can be at least 0.5, 0.55, 0.6, 0.65, 0.7, 0.75, 0.8, 0.85, 0.9, or 0.95.

The first Sanger sequencing trace can be from capillary electrophoresis. The first Sanger sequencing trace can comprise a single electropherogram.

The first target sequence can comprise a first guide RNA sequence for CRISPR/Cas, or a complement of the first guide RNA sequence for CRISPR/Cas. The determining can comprise obtaining a second target sequence, wherein the second target sequence comprises a second guide RNA sequence for CRISPR/Cas or a complement of the second guide RNA sequence for CRISPR/Cas. The determining can comprise obtaining a sequence of a donor nucleic acid for homology-directed repair.

The nucleic acid editing tool can comprise CRISPR/Cas. The nucleic acid editing tool can comprise more than one guide RNA sequence for a CRISPR/Cas. The nucleic acid editing tool can comprise a CRISPR/Cas comprising a single guide RNA. The nucleic acid editing tool can comprise a CRISPR/Cas and a donor nucleic acid for homology-directed repair.

The frequency of the predicted sequence can comprise a relative amount of the predicted sequence relative to other predicted sequences. The initial set of predicted sequences can include at least 1, 10, 100, 1,000, 10,000, or 100,000 predicted sequences.

The determining can comprise identifying an alignment window in the second Sanger sequencing trace, wherein the alignment window (i) comprises at least three nucleotides, (ii) is 5' of a predicted cut site in the first target sequence, and (iii) has an average Phred quality score of at least about 15, 20, 25, or 30.

The determining can comprise aligning the first Sanger sequencing trace and second Sanger sequencing trace to the alignment window. A 3' end of the alignment window can be about 5, 10, 15, 20, or 25 nucleotides 5' of the predicted cut site in the first target sequence. The alignment window can comprise at least 10, 25, 50, 100, 150, or 200 nucleotides.

The determining can comprise identifying an inference window comprising the predicted cut site in the second Sanger sequencing trace, wherein (i) a 5' end of the inference window is at about 10 to about 50 nucleotides 5' of the predicted cut site and (ii) a 3' end of the inference window at about 10 to about 200 nucleotides 3' of the predicted cut site. The 5' end of the inference window can be at 25 nucleotides 5' of the predicted cut site in the first target sequence, and the 3' end of the inference window can be at 100 nucleotides 3' of the predicted cut site in the first target sequence.

The identifying the inference window can comprise trimming the inference window based on a quality score of the second Sanger sequence trace. The inference window can comprise an average Phred quality score of at least 15, 20, 25, or 30. The inference window can be determined automatically without a human intervention. The method can further comprise performing a regression analysis between the initial set of predicted sequences and the first Sanger sequencing trace at the inference window, thereby identifying a subset of predicted sequences from the initial set, wherein the identified subset of resembles the first Sanger sequencing trace.

The first plurality of nucleic acid molecules and the second plurality of nucleic acid molecules can be from a same cell type. The method can further comprise calculating a knockout score of the nucleic acid editing tool, wherein the knockout score is a frequency of the predicted knockout sequence in the subset of the initial set. The method can further comprise reporting to the user the predicted knockout sequence and the knockout score.

In another aspect, the present disclosure provides a computer program product comprising a non-transitory computer-readable medium having computer-executable code encoded therein, the computer-executable code adapted to be executed to implement any one of the subject methods for determining a predicted knockout sequence of a single nucleic acid molecule based on a first Sanger sequencing trace and a second Sanger sequencing trace, wherein the predicted knockout sequence comprises an indel when compared to the second Sanger sequencing trace. In another aspect, the present disclosure provides a computer system comprising one or more processors to execute the computer program product.

In an aspect, the present disclosure provides a method comprising determining, by a computer system, a predicted termination sequence of a single nucleic acid molecule based on a first Sanger sequencing trace and a second Sanger sequencing trace, wherein the predicted termination sequence comprises an indel when compared to the second Sanger sequencing trace, and wherein the indel of the predicted knockout sequence yields a stop codon.

The stop codon can be a nonsense mutation. The stop codon can be a premature stop codon. A DNA sequence of the stop codon can be selected from the group consisting of: TAG, TAA, and TGA. An RNA sequence encoded by a DNA comprising the stop codon can be selected from the group consisting of: UAG, UAA, and UGA.

The first Sanger sequencing trace can be from a first plurality of nucleic acid molecules from a first sample, wherein the second Sanger sequencing trace is from a second plurality of nucleic acid molecules from a second sample, and wherein the first sample and second sample are different. The first plurality of nucleic acid molecules can comprise nucleic acid molecules contacted with a nucleic acid editing tool. The nucleic acid editing tool can comprise a nuclease. The nucleic acid editing tool may not have contacted the second plurality of nucleic acid molecules.

The determining can comprise obtaining a first target sequence, wherein the target sequence is in the second plurality of nucleic acid molecules or is in the complement of sequence of the second plurality of nucleic acid molecules.

The determining can comprise generating an initial set of predicted sequences of individual nucleic acid molecules based on the second Sanger sequencing trace, wherein the initial set comprises the predicted knockout sequence. The initial set of predicted sequences of individual nucleic acid molecules can comprise insertions or deletions relative to the first target sequence. The insertions or deletions can be adjacent to a site in the first target sequence predicted to be cut by the nucleic acid editing tool.

The determining can comprise comparing the initial set of predicted sequences of individual nucleic acid molecules to the first Sanger sequencing trace of the first plurality of nucleic acid molecules from the first sample. The comparing can comprise identifying a subset of the initial set of predicted sequences of individual nucleic acid molecules by performing a regression analysis. The regression analysis can comprise a non-negative least squares regression analysis or a regularized regression analysis (e.g., a Lasso regression analysis). The regression analysis can identify sequences of the initial set of predicted sequences of individual molecules, wherein the identified sequences in combination resemble the first Sanger sequencing trace. An R-squared value of the regression analysis can be at least 0.5, 0.55, 0.6, 0.65, 0.7, 0.75, 0.8, 0.85, 0.9, or 0.95.

The first Sanger sequencing trace can be from capillary electrophoresis. The first Sanger sequencing trace can comprise a single electropherogram.

The first target sequence can comprise a first guide RNA sequence for CRISPR/Cas, or a complement of the first guide RNA sequence for CRISPR/Cas. The determining can comprise obtaining a second target sequence, wherein the second target sequence comprises a second guide RNA sequence for CRISPR/Cas or a complement of the second guide RNA sequence for CRISPR/Cas. The determining can comprise obtaining a sequence of a donor nucleic acid for homology-directed repair.

The nucleic acid editing tool can comprise CRISPR/Cas. The nucleic acid editing tool can comprise more than one guide RNA sequence for a CRISPR/Cas. The nucleic acid editing tool can comprise a CRISPR/Cas comprising a single guide RNA. The nucleic acid editing tool can comprise a CRISPR/Cas and a donor nucleic acid for homology-directed repair.

The frequency of the predicted sequence can comprise a relative amount of the predicted sequence relative to other predicted sequences. The initial set of predicted sequences can include at least 1, 10, 100, 1,000, 10,000, or 100,000 predicted sequences.

The determining can comprise identifying an alignment window in the second Sanger sequencing trace, wherein the alignment window (i) comprises at least three nucleotides, (ii) is 5' of a predicted cut site in the first target sequence, and (iii) has an average Phred quality score of at least about 15, 20, 25, or 30. The determining can comprise aligning the first Sanger sequencing trace and second Sanger sequencing trace to the alignment window. A 3' end of the alignment window can be about 5, 10, 15, 20, or 25 nucleotides 5' of the predicted cut site in the first target sequence. The alignment window comprises at least 10, 25, 50, 100, 150, or 200 nucleotides.

The determining can comprise identifying an inference window comprising the predicted cut site in the second Sanger sequencing trace, wherein (i) a 5' end of the inference window is at about 10 to about 50 nucleotides 5' of the predicted cut site and (ii) a 3' end of the inference window at about 10 to about 200 nucleotides 3' of the predicted cut site.

The 5' end of the inference window can be at 25 nucleotides 5' of the predicted cut site in the first target sequence, and the 3' end of the inference window can be at 100 nucleotides 3' of the predicted cut site in the first target sequence.

The identifying the inference window can comprise trimming the inference window based on a quality score of the second Sanger sequence trace. The inference window can comprise an average Phred quality score of at least 15, 20, 25, or 30. The inference window can be determined automatically without a human intervention. The method can further comprise performing a regression analysis between the initial set of predicted sequences and the first Sanger sequencing trace at the inference window, thereby identifying a subset of predicted sequences from the initial set, wherein the identified subset of resembles the first Sanger sequencing trace.

The first plurality of nucleic acid molecules and the second plurality of nucleic acid molecules can be from a same cell type.

The method can further comprise calculating a termination score of the nucleic acid editing tool, wherein the termination score is a frequency of the predicted termination sequence in the subset of the initial set. The method can further comprise reporting to the user the predicted knockout sequence and the knockout score.

In another aspect, the present disclosure provides a computer program product comprising a non-transitory computer-readable medium having computer-executable code encoded therein, the computer-executable code adapted to be executed to implement any one of the subject methods for determining a predicted termination sequence of a single nucleic acid molecule based on a first Sanger sequencing trace and a second Sanger sequencing trace, wherein the predicted termination sequence comprises an indel when compared to the second Sanger sequencing trace, and wherein the indel of the predicted knockout sequence yields a stop codon. In another aspect, the present disclosure provides the computer system comprising one or more processors to execute the computer program product.

In one aspect, the present disclosure provides a method comprising, by using a computer system, (a) providing a plurality of nucleic acid sequencing data sets at once, wherein each data set comprises a first Sanger sequencing trace, a second Sanger sequencing trace, and a first target sequence of a nucleic acid editing tool, and (b) for each data set, determining a subset of predicted sequences from an initial set of predicted sequences of individual nucleic acid molecules based on the second Sanger sequencing trace, wherein the subset of predicted sequences in combination resembles the first Sanger sequencing trace.

The nucleic acid editing tool can comprise a nuclease. The first Sanger sequence can be from a first plurality of nucleic acid molecules from a first sample, the second Sanger sequence is from a second plurality of nucleic acid molecules from a second sample, and the first and second samples are different. The first plurality of nucleic acid molecules can comprise nucleic acid molecules contacted with the nucleic acid editing tool. The nucleic acid editing tool may not have contacted the second plurality of nucleic acid molecules.

The method can further comprise generating the initial set of predicted sequences of individual nucleic acid molecules based on the second Sanger sequencing trace. The first target sequence can be in the second plurality of nucleic acid molecules or can be in the complement of sequence of the second plurality of nucleic acid molecules. The initial set of predicted sequences of individual nucleic acid molecules can comprise insertions or deletions relative to the first target sequence of the nucleic acid editing tool. The insertions or deletions can be adjacent to a site in the first target sequence predicted to be cut by the nucleic acid editing tool.

The determining can comprise comparing the initial set of predicted sequences of individual nucleic acid molecules to the first Sanger sequencing trace of the first plurality of nucleic acid molecules from the first sample. The comparing can comprise identifying a subset of the initial set of predicted sequences of individual nucleic acid molecules by performing a regression analysis. The regression analysis can comprise a non-negative least squares regression analysis or a regularized regression analysis (e.g., Lasso regression analysis). The regression analysis can identify sequences of the initial set of predicted sequences of individual molecules, wherein the identified sequences in combination resemble the first Sanger sequencing trace. An R-squared value of the regression analysis is at least 0.5, 0.55, 0.6, 0.65, 0.7, 0.75, 0.8, 0.85, 0.9, or 0.95.

The method can further comprise providing a second target sequence of the gene editing tool, wherein the second target sequence is in the second plurality of nucleic acid molecules or is in the complement of sequence of the second plurality of nucleic acid molecules, and wherein the first and second target sequences are different.

The method can further comprise determining a base trace by trimming the second Sanger sequencing trace, wherein the trimming comprises subtracting a portion of the second Sanger sequencing trace disposed between a first predicted cut site of the nucleic acid editing tool in the first target sequence and a second predicted cut site of the nucleic acid editing tool in the second target sequence.

The initial set of predicted sequences can further comprise an additional set of predicted sequences of individual nucleic acid molecules based on the base trace. The additional set of predicted sequences can comprise insertions or deletions adjacent to the first and second predicted cut sites.

The method can further comprise determining a predicted knockout sequence from the subset of predicted sequences, wherein the predicted knockout sequence comprises an indel when compared to the second Sanger sequencing trace, and wherein the indel of the predicted knockout sequence is not a multiple of three nucleotides and/or longer than a threshold length. The threshold length of the indel is at least 10, 11, 12, 13, 14, 15, 16, 17, 18, 19, 20, 21, 22, 23, 24, or 25 nucleotides.

The method can further comprise determining a predicted termination sequence from the subset of predicted sequences, wherein the predicted termination sequence comprises an indel when compared to the second Sanger sequencing trace, and wherein the indel of the predicted termination sequence yields a stop codon. The stop codon can be a nonsense mutation. The stop codon can be a premature stop codon. A DNA sequence of the stop codon can be selected from the group consisting of: TAG, TAA, and TGA. An RNA sequence encoded by a DNA comprising the stop codon can be selected from the group consisting of: UAG, UAA, and UGA.

The method can further comprise calculating a termination score of the nucleic acid editing tool, wherein the termination score is a frequency of the predicted termination sequence in the subset of the initial set.

The method can further comprise reporting to a user a first and second predicted sequences from the subset, wherein the first and second predicted sequences each comprises an indel when compared to the second Sanger sequencing trace, and wherein the indels of the first and second predicted sequences have a same size and a different nucleic acid sequence. The method can further comprise reporting to the user the first predicted sequence, the second predicted sequence, a first frequency of the first predicted sequence in the subset, and a second frequency of the second predicted sequence in the subset.

The determining a subset of predicted sequences from an initial set of predicted sequences for each of the plurality of nucleic acid sequencing data sets can be executed automatically without a human intervention.

In another aspect, the present disclosure provides a computer program product comprising a non-transitory computer-readable medium having computer-executable code encoded therein, the computer-executable code adapted to be executed to implement any of the subject methods for (a) providing a plurality of nucleic acid sequencing data sets at once, wherein each data set comprises a first Sanger sequencing trace, a second Sanger sequencing trace, and a first target sequence of a nucleic acid editing tool, and (b) for each data set, determining a subset of predicted sequences from an initial set of predicted sequences of individual nucleic acid molecules based on the second Sanger sequencing trace, wherein the subset of predicted sequences in combination resembles the first Sanger sequencing trace. In another aspect, the present disclosure provides a computer system comprising one or more processors to execute the computer program product.

In an aspect, the present disclosure provides a method comprising determining, by a computer system, a first predicted sequence of a single nucleic acid molecule and a second predicted sequence of a single nucleic acid molecule, wherein the first and second predicted sequences are based on a first Sanger sequencing trace of a first plurality of nucleic acid molecules from a first sample, wherein the first and second predicted sequences each comprises an indel when compared to a second Sanger sequencing trace of a second plurality of nucleic acid molecules from a second sample, and wherein the indels of the first and second predicted sequences have a same size and a different nucleic acid sequence.

The first plurality of nucleic acid molecules can comprise nucleic acid molecules contacted with a nucleic acid editing tool. The nucleic acid editing tool can comprise a nuclease. The first sample and second sample can be different. The nucleic acid editing tool may not have contacted the second plurality of nucleic acid molecules.

The determining can comprise obtaining a first target sequence, wherein the target sequence is in the second plurality of nucleic acid molecules or is in the complement of sequence of the second plurality of nucleic acid molecules. The determining can comprise generating an initial set of predicted sequences of individual nucleic acid molecules based on the second Sanger sequencing trace. The initial set of predicted sequences of individual nucleic acid molecules can comprise insertions or deletions relative to the first target sequence. The insertions or deletions can be adjacent to a site in the first target sequence predicted to be cut by the nucleic acid editing tool.

The determining can comprise comparing the initial set of predicted sequences of individual nucleic acid molecules to the first Sanger sequencing trace of the first plurality of nucleic acid molecules from the first sample. The comparing can comprise identifying a subset of the initial set of predicted sequences of individual nucleic acid molecules by performing a regression analysis. The regression analysis can comprise a non-negative least squares regression analysis or a regularized regression analysis (e.g., a Lasso regression analysis). The regression analysis can identify sequences of the initial set of predicted sequences of individual molecules, wherein the identified sequences in combination resemble the first Sanger sequencing trace. An R-squared value of the regression analysis can be at least 0.5, 0.55, 0.6, 0.65, 0.7, 0.75, 0.8, 0.85, 0.9, or 0.95.

The method can further comprise reporting to a user the first predicted sequence, the second predicted sequence, a first frequency of the first predicted sequence in the subset of the initial set, and a second frequency of the second predicted sequence in the subset of the initial set.

The first or second Sanger sequencing trace can be from capillary electrophoresis. The first or second Sanger sequencing trace can comprise a single electropherogram.

The first target sequence can comprise a first guide RNA sequence for CRISPR/Cas, or a complement of the first guide RNA sequence for CRISPR/Cas. The determining can comprise obtaining a second target sequence, wherein the second target sequence comprises a second guide RNA sequence for CRISPR/Cas or a complement of the second guide RNA sequence for CRISPR/Cas. The determining can comprise obtaining a sequence of a donor nucleic acid for homology-directed repair.

The nucleic acid editing tool can comprise CRISPR/Cas. The nucleic acid editing tool can comprise more than one guide RNA sequence for a CRISPR/Cas. The nucleic acid editing tool can comprise a CRISPR/Cas comprising a single guide RNA. The nucleic acid editing tool can comprise a CRISPR/Cas and a donor nucleic acid for homology-directed repair.

The frequency of the predicted sequence can comprise a relative amount of the predicted sequence relative to other predicted sequences.

The initial set of predicted sequences can include at least 1, 10, 100, 1,000, 10,000, or 100,000 predicted sequences.

The determining can comprise identifying an alignment window in the second Sanger sequencing trace, wherein the alignment window (i) comprises at least three nucleotides, (ii) is 5' of a predicted cut site in the first target sequence, and (iii) has an average Phred quality score of at least about 15, 20, 25, or 30. The determining can comprise aligning the first Sanger sequencing trace and second Sanger sequencing trace to the alignment window. A 3' end of the alignment window can be about 5, 10, 15, 20, or 25 nucleotides 5' of the predicted cut site in the first target sequence. The alignment window can comprise at least 10, 25, 50, 100, 150, or 200 nucleotides.

The determining can comprise identifying an inference window comprising the predicted cut site in the second Sanger sequencing trace, wherein (i) a 5' end of the inference window is at about 10 to about 50 nucleotides 5' of the predicted cut site and (ii) a 3' end of the inference window at about 10 to about 200 nucleotides 3' of the predicted cut site. The 5' end of the inference window can be at 25 nucleotides 5' of the predicted cut site in the first target sequence, and the 3' end of the inference window can be at 100 nucleotides 3' of the predicted cut site in the first target sequence. The identifying the inference window can comprise trimming the inference window based on a quality score of the second Sanger sequence trace. The inference window can comprise an average Phred quality score of at least 15, 20, 25, or 30. The inference window can be determined automatically without a human intervention.

The method can further comprise performing a regression analysis between the initial set of predicted sequences and the first Sanger sequencing trace at the inference window, thereby identifying a subset of predicted sequences from the initial set, wherein the identified subset of predicted sequences resembles the first Sanger sequencing trace.

The first plurality of nucleic acid molecules and the second plurality of nucleic acid molecules can be from a same cell type.

In another aspect, the present disclosure provides a computer program product comprising a non-transitory computer-readable medium having computer-executable code encoded therein, the computer-executable code adapted to be executed to implement any of the subject methods for determining, by a computer system, a first predicted sequence of a single nucleic acid molecule and a second predicted sequence of a single nucleic acid molecule, wherein the first and second predicted sequences are based on a first Sanger sequencing trace of a first plurality of nucleic acid molecules from a first sample, wherein the first and second predicted sequences each comprises an indel when compared to a second Sanger sequencing trace of a second plurality of nucleic acid molecules from a second sample, and wherein the indels of the first and second predicted sequences have a same size and a different nucleic acid sequence. In another aspect, the present disclosure provides a computer system comprising one or more processors to execute the computer program product.

In one aspect, the present disclosure provides a method for deducing a mutation in a gene, comprising: (a) providing (i) a first sequencing trace of the gene without an exposure to a gene editing tool, (ii) a second sequencing trace of the gene with an exposure to the gene editing tool, (iii) a first target sequence of the gene, and (iv) a second target sequence of the gene, wherein the first and second sequencing traces each comprises a Sanger sequencing trace, and wherein the first and second target sequences are different; (b) identifying (i) a first cut site of the first target sequence in the first sequencing trace and (ii) a second cut site of the second target sequence in the first sequencing trace, wherein the first cut site is upstream of the second cut site; (c) generating a base trace by subtracting the sequencing trace between the first and second cut sites from the first sequencing trace; and (d) comparing the base trace and the second sequencing trace to thereby identify a mutation in the gene.

The method can further comprise generating an initial set comprising (i) the base trace and (ii) a plurality of predicted mutated traces of the base trace that each comprises an indel at the first or second cut site. The plurality of predicted mutated traces can include at least 1, 10, 100, 1,000, 10,000, or 100,000 predicted mutated traces.

The method can further comprise identifying a subset of the initial set by using a regression analysis, wherein a linear combination of each trace of the subset substantially resembles the second sequencing trace. The method can further comprise using a non-negative least squares regression analysis to identify the subset from the initial set. An R-squared value of the regression analysis of the subset can be at least 0.90, 0.91, 0.92, 0.93, 0.94, or 0.95.

The method can further comprise quantifying a frequency of each trace in the subset. The method can further comprise reporting to a user the sequence and the frequency of each trace in the subset, wherein the first and second sequencing traces and the first and second target sequences are provided by the user.

The method can further comprise aligning the base trace and the second sequencing trace to an alignment window of the base trace, wherein the alignment window (i) comprises at least three nucleotides, (ii) is upstream of the first cut site, and (iii) has an average Phred quality score of at least about 15, 20, 25, or 30. The method can further comprise, wherein each of the plurality of predicted mutated traces of the base trace comprises the alignment window, aligning the plurality of predicted mutated traces of the base trace and the second sequencing trace to the alignment window. The method can further comprise selecting a 3' end of the alignment window at about 5, 10, 15, 20, or 25 nucleotides upstream of the first cut site, wherein a 5' end of the alignment window is upstream of the 3' end of the alignment window. The alignment window can comprise at least about 10, 25, 50, 100, 150, or 200 nucleotides.

The method can further comprise performing the regression analysis between the initial set and the second sequencing trace at an inference window of the base trace to identify the subset, wherein the inference window comprises (i) at least three nucleotides, (ii) a 5' end upstream of the first cut site, and (iii) a 3' end downstream of the second cut site.

The method can further comprise identifying the inference window such that the inference window has an average Phred quality score of at least 15, 20, 25, or 30, wherein the identifying is performed automatically without a human intervention. The method can further comprise selecting (i) the 5' end of the inference window at about 10 to about 50 nucleotides upstream of the first cut site and (ii) the 3' end of the inference window at about 10 to about 200 nucleotides downstream of the second cut site. The method can further comprise selecting (i) the 5' end of the inference window at 25 nucleotides upstream of the first cut site and (ii) the 3' end of the inference window at 100 nucleotides downstream of the second cut site. The indel can range from about 1 to about 100 nucleotides. The indel can range from about 1 to about 50 nucleotides.

The initial set can further comprise (i) the first sequencing trace and (ii) an additional plurality of predicted mutated traces of the first sequencing trace that each comprises an indel at the first cut site or the second cut site.

The method can further comprise (i) aligning the second sequencing trace to the first sequencing trace and then (ii) performing the regression analysis between the initial set and the second sequencing trace to identify the subset.

The first sequencing trace of the gene can be from a first cell without the exposure to the gene editing tool, the second sequencing trace of the gene can be from a second cell with the exposure to the gene editing tool, and the first and second cells can be the same type of cells.

The method can further comprise using a nuclease as the gene editing tool. The nuclease can be selected from the group consisting of: CRISPR nuclease, TALEN, or ZFN. The CRISPR nuclease can be selected from the group consisting of: Cas9, C2c1, C2c3, or Cpf1. The method can further comprise further comprising using CRISPR/Cas9 with (i) a first guide RNA (gRNA), wherein a portion of the first gRNA hybridizes with a first binding sequence of the gene that is complementary to the first target sequence and (ii) a second gRNA, wherein a portion of the second gRNA hybridizes with a second binding sequence of the gene that is complementary to the second target sequence.

The first and second target sequences can be about 15 to about 25 nucleotides.

In one aspect, the present disclosure provides a computer program product comprising a non-transitory computer-readable medium having computer-executable code encoded therein, the computer-executable code adapted to be executed to implement a method for deducing a mutation in a gene, comprising (a) providing (i) a first sequencing trace of the gene without an exposure to a gene editing tool, (ii) a second sequencing trace of the gene with an exposure to the gene editing tool, (iii) a first target sequence of the gene, and (iv) a second target sequence of the gene, wherein the first and second sequencing traces each comprises a Sanger sequencing trace, and wherein the first and second target sequences are different; (b) identifying (i) a first cut site of the first target sequence in the first sequencing trace and (ii) and a second cut site of the second target sequence in the first sequencing trace, wherein the first cut site is upstream of the second cut site; (c) generating a base trace by subtracting the sequencing trace between the first and second cut sites from the first sequencing trace; and (d) comparing the base trace and the second sequencing trace to thereby identify a mutation in the gene.

In one aspect, the present disclosure provides a method for deducing a mutation in a gene, comprising: (a) providing (i) a first sequencing trace of the gene without an exposure to a gene editing tool, (ii) a second sequencing trace of the gene with an exposure to the gene editing tool, and (iii) a target sequence of the gene, wherein the first and second sequencing traces each comprises a Sanger sequencing trace; (b) generating an initial set comprising (i) the first sequencing trace and (ii) a plurality of predicted mutated traces of the first sequencing trace that each comprises an indel at a cut site of the target sequence; (c) identifying a subset of the initial set by using a regression analysis, wherein a linear combination of each trace of the subset substantially resembles the second sequencing trace; (d) identifying a knockout trace from the subset, wherein a length of the indel of the knockout trace is (i) not a multiple of three nucleotides, (ii) longer than a threshold length, or (iii) both; and (e) calculating a knockout score of the gene editing tool, wherein the knockout score is a proportion of the knockout trace in the subset.

The threshold length of the indel can be at least 10, 11, 12, 13, 14, 15, 16, 17, 18, 19, 20, 21, 22, 23, 24, or 25 nucleotides.

The first and second sequencing traces each (i) can be from capillary electrophoresis or (ii) can comprise a single electropherogram.

The plurality of predicted mutated traces can include at least 1, 10, 100, 1,000, 10,000, or 100,000 predicted mutated traces.

The method can further comprise using a non-negative least squares regression analysis to identify the subset from the initial set. An R-squared value of the regression analysis of the subset can be at least 0.90, 0.91, 0.92, 0.93, 0.94, or 0.95. The first sequencing trace, the second sequencing trace, and the target sequence can be provided by a user, and method can further comprise reporting the knockout score to the user.

The method can further comprise aligning the first and second sequencing traces to an alignment window of the first sequencing trace, wherein the alignment window (i) comprises at least three nucleotides, (ii) is upstream of the cut site, and (iii) has an average Phred quality score of at least about 15, 20, 25, or 30. Each of the plurality of predicted mutated traces of the first sequencing trace can comprise the alignment window, and the method can further comprise aligning the plurality of predicted mutated traces of the first sequencing trace and the second sequencing trace to the alignment window. The method can further comprise selecting a 3' end of the alignment window at about 5, 10, 15, 20, or 25 nucleotides upstream of the cut site, wherein a 5' end of the alignment window is upstream of the 3' end of the alignment window. The alignment window can comprise at least about 10, 25, 50, 100, 150, or 200 nucleotides.

The method can further comprise performing the regression analysis within an inference window of the first sequencing trace to identify the subset, wherein the inference window comprises (i) at least three nucleotides, (ii) a 5' end that is upstream of the cut site, and (iii) a 3' end that is downstream of the cut site.

The method can further comprise identifying the inference window such that the inference window has an average Phred quality score of at least 15, 20, 25, or 30, wherein the identifying is performed automatically without a human intervention. The method can further comprise selecting (i) the 5' end of the inference window at about 10 to about 50 nucleotides upstream of the cut site and (ii) the 3' end of the inference window at about 10 to about 200 nucleotides downstream of the cut site. The method can further comprise selecting (i) the 5' end of the inference window at 25 nucleotides upstream of the cut site and (ii) the 3' end of the inference window at 100 nucleotides downstream of the cut site.

The indel can range from about 1 to about 100 nucleotides. The indel can range from about 1 to about 50 nucleotides.

The first sequencing trace of the gene can be from a first cell without the exposure to the gene editing tool, the second sequencing trace of the gene can be from a second cell with the exposure to the gene editing tool, and the first and second cells can be the same type of cells.

The method can further comprise using a nuclease as the gene editing tool. The nuclease can be selected from the group consisting of: CRISPR nuclease, TALEN, or ZFN. The CRISPR nuclease can be selected from the group consisting of: Cas9, C2c1, C2c3, or Cpf1. The method can further comprise using CRISPR/Cas9 with a guide RNA (gRNA), wherein a portion of the gRNA hybridizes with a binding sequence of the gene that is complementary to the target sequence.

The target sequence can be about 15 to about 25 nucleotides.

In one aspect, the present disclosure provides a computer program product comprising a non-transitory computer-readable medium having computer-executable code encoded therein, the computer-executable code adapted to be executed to implement a method for deducing a mutation in a gene, comprising: (a) providing (i) a first sequencing trace of the gene without an exposure to a gene editing tool, (ii) a second sequencing trace of the gene with an exposure to the gene editing tool, and (iii) a target sequence of the gene, wherein the first and second sequencing traces each comprises a Sanger sequencing trace; (b) generating an initial set comprising (i) the first sequencing trace and (ii) a plurality of predicted mutated traces of the first sequencing trace that each comprises an indel at a cut site of the target sequence; (c) identifying a subset of the initial set by using a regression analysis, wherein a linear combination of each trace of the subset substantially resembles the second sequencing trace; (d) identifying a knockout trace from the subset, wherein a length of the indel of the knockout trace is (i) not a multiple of three nucleotides, (ii) longer than a threshold length, or (iii) both; and (e) calculating a knockout score of the gene editing tool, wherein the knockout score is a proportion of the knockout trace in the subset.

In one aspect, the present disclosure provides a method for deducing a mutation in a gene, comprising: (a) providing (i) a first sequencing trace of the gene without an exposure to a gene editing tool, (ii) a second sequencing trace of the gene with an exposure to the gene editing tool, and (iii) a target sequence of the gene, wherein the first and second sequencing traces each comprises a Sanger sequencing trace; (b) generating an initial set comprising (i) the first sequencing trace and (ii) a plurality of predicted mutated traces of the first sequencing trace that each comprises an indel at a cut site of the target sequence; (c) identifying a subset of the initial set by using a regression analysis, wherein a linear combination of each trace of the subset substantially resembles the second sequencing trace; and (d) identifying a termination trace from the subset, wherein the termination trace is one of the plurality of predicted mutated traces, and wherein the indel of the termination trace yields a stop codon.

The stop codon can be at or near the cut site. The stop codon can be a nonsense mutation and/or a premature stop codon. The DNA sequence of the stop codon can be selected from the group consisting of: TAG, TAA, and TGA. The RNA sequence encoded by a DNA comprising the stop codon can be selected from the group consisting of: UAG, UAA, and UGA.

The method can further comprise calculating a termination score of the gene editing tool, wherein the termination score is a proportion of the termination trace in the subset. The first sequencing trace, the second sequencing trace, and the target sequence can be provided by a user, and the method can further comprise reporting the termination score to the user.

The first and second sequencing traces each (i) can be from capillary electrophoresis or (ii) can comprise a single electropherogram.

The plurality of predicted mutated traces can include at least 1, 10, 100, 1,000, 10,000, or 100,000 predicted mutated traces.

The method can further comprise using a non-negative least squares regression analysis to identify the subset from the initial set. An R-squared value of the regression analysis of the subset is at least 0.90, 0.91, 0.92, 0.93, 0.94, or 0.95.

The method can further comprise aligning the first and second sequencing traces to an alignment window of the first sequencing trace, wherein the alignment window (i) comprises at least three nucleotides, (ii) is upstream of the cut site, and (iii) has an average Phred quality score of at least about 15, 20, 25, or 30. Each of the plurality of predicted mutated traces of the first sequencing trace can comprise the alignment window, and the method can further comprise aligning the plurality of predicted mutated traces of the first sequencing trace and the second sequencing trace to the alignment window. The method can further comprise selecting a 3' end of the alignment window at about 5, 10, 15, 20, or 25 nucleotides upstream of the cut site, wherein a 5' end of the alignment window is upstream of the 3' end of the alignment window. The alignment window can comprise at least about 10, 25, 50, 100, 150, or 200 nucleotides.

The method can further comprise performing the regression analysis within an inference window of the first sequencing trace to identify the subset, wherein the inference window comprises (i) at least three nucleotides, (ii) a 5' end that is upstream of the cut site, and (iii) a 3' end that is downstream of the cut site. The method can further comprise identifying the inference window such that the inference window has an average Phred quality score of at least 15, 20, 25, or 30, wherein the identifying is performed automatically without a human intervention. The method can further comprise selecting (i) the 5' end of the inference window at about 10 to about 50 nucleotides upstream of the cut site and (ii) the 3' end of the inference window at about 10 to about 200 nucleotides downstream of the cut site. The method can further comprise selecting (i) the 5' end of the inference window at 25 nucleotides upstream of the cut site and (ii) the 3' end of the inference window at 100 nucleotides downstream of the cut site.

The indel can range from about 1 to about 100 nucleotides. The indel can range from about 1 to about 50 nucleotides.

The first sequencing trace of the gene can be from a first cell without the exposure to the gene editing tool, the second sequencing trace of the gene can be from a second cell with the exposure to the gene editing tool, and the first and second cells can be the same type of cells.

The method can further comprise using a nuclease as the gene editing tool. The nuclease can be selected from the group consisting of: CRISPR nuclease, TALEN, or ZFN. The CRISPR nuclease can be selected from the group consisting of: Cas9, C2c1, C2c3, or Cpf1. The method can further comprise using CRISPR/Cas9 with a guide RNA (gRNA), wherein a portion of the gRNA hybridizes with a binding sequence of the gene that is complementary to the target sequence.

The target sequence can be about 15 to about 25 nucleotides.

In one aspect, the present disclosure provides a computer program product comprising a non-transitory computer-readable medium having computer-executable code encoded therein, the computer-executable code adapted to be executed to implement a method for deducing a mutation in a gene, comprising: (a) providing (i) a first sequencing trace of the gene without an exposure to a gene editing tool, (ii) a second sequencing trace of the gene with an exposure to the gene editing tool, and (iii) a target sequence of the gene, wherein the first and second sequencing traces each comprises a Sanger sequencing trace; (b) generating an initial set comprising (i) the first sequencing trace and (ii) a plurality of predicted mutated traces of the first sequencing trace that each comprises an indel at a cut site of the target sequence; (c) identifying a subset of the initial set by using a regression analysis, wherein a linear combination of each trace of the subset substantially resembles the second sequencing trace; and (d) identifying a termination trace from the subset, wherein the termination trace is one of the plurality of predicted mutated traces, and wherein the indel of the termination trace yields a stop codon.

In one aspect, the present disclosure provides a method for deducing a mutation in a gene, comprising: (a) providing a plurality of gene sequencing data sets at once, wherein each data set comprises: (i) a first sequencing trace of the gene without an exposure to a gene editing tool, (ii) a second sequencing trace of the gene with an exposure to the gene editing tool; and (iii) a target sequence of the gene, wherein the first and second sequencing traces each comprises a Sanger sequencing trace; and (b) for each gene sequencing data set, performing the steps comprising: (i) generating an initial set comprising (A) the first sequencing trace and (B) a plurality of predicted mutated traces of the first sequencing trace that each comprises an indel at a cut site of the target sequence; (ii) identifying a subset of the initial set by using a regression analysis, wherein a linear combination of each trace of the subset substantially resembles the second sequencing trace; and (iii) quantifying a frequency of each trace in the subset.

A first gene of a first data set of the plurality of gene sequencing data sets and a second gene of a second data set of the plurality of gene sequencing data sets can be different.

All genes of the plurality of gene sequencing data sets can be the same.

The plurality of gene sequencing data sets can be provided at once prior to the performing the step (b). The plurality of gene sequencing data sets can be received from a user, and the method can further comprise reporting to the user the sequence and the frequency of each trace in the subset.

A data set of the plurality of gene sequencing data sets can further comprise a second target sequence of the gene that is different from the target sequence. The method can further comprise generating a base trace by subtracting the sequencing trace between the cut site and a second cut site of the second target sequence from the first sequencing trace, wherein the cut site is upstream of the second cut site. Each of the plurality of predicted mutated traces of the first sequencing trace can comprise the indel at the cut site or the second cut site. The initial set can further comprise an additional plurality of predicted mutated traces of the base trace that each comprises an indel at the cut site or the second cut site.

For a data set of the plurality of gene sequencing data sets, the method can further comprise identifying a knockout trace from the subset, wherein a length of the indel of the knockout trace is not a multiple of three nucleotides and/or longer than a threshold length. The threshold length of the indel can be at least 10, 11, 12, 13, 14, 15, 16, 17, 18, 19, 20, 21, 22, 23, 24, or 25 nucleotides.

The method can further comprise calculating a knockout score of the gene editing tool, wherein the knockout score is a proportion of the knockout trace in the subset. The plurality of gene sequencing data sets can be received from a user, and the method can further comprise reporting the knockout score to the user.

For a data set of the plurality of gene sequencing data sets, the method can further comprise identifying a termination trace from the subset, wherein the termination trace is one of the plurality of predicted mutated traces, and wherein the indel of the termination trace yields a stop codon. The stop codon can be at or near the cut site. The stop codon can be a nonsense mutation and/or a premature stop codon. A DNA sequence of the stop codon can be selected from the group consisting of: TAG, TAA, and TGA. An RNA sequence of the stop codon can be selected from the group consisting of: UAG, UAA, and UGA.

The method can further comprise calculating a termination score of the gene editing tool, wherein the termination score is a proportion of the termination trace in the subset. The plurality of gene sequencing data sets can be received from a user, and the method can further comprise reporting the termination score to the user.

The first and second sequencing traces each (i) can be from capillary electrophoresis or (ii) can comprise a single electropherogram.

The plurality of predicted mutated traces can include at least 1, 10, 100, 1,000, 10,000, or 100,000 predicted mutated traces.

The method can further comprise using a non-negative least squares regression analysis to identify the subset from the initial set. An R-squared value of the regression analysis of the subset can be at least 0.90, 0.91, 0.92, 0.93, 0.94, or 0.95.

The indel can range from about 1 to about 100 nucleotides. The indel can range from about 1 to about 50 nucleotides.

The first sequencing trace of the gene can be from a first cell without the exposure to the gene editing tool, the second sequencing trace of the gene can be from a second cell with the exposure to the gene editing tool, and the first and second cells can be the same type of cells.

The method can further comprise using a nuclease as the gene editing tool. The nuclease can be selected from the group consisting of: CRISPR nuclease, TALEN, or ZFN. The CRISPR nuclease can be selected from the group consisting of: Cas9, C2c1, C2c3, or Cpf1. The method can further comprise using CRISPR/Cas9 with a guide RNA (gRNA), wherein a portion of the gRNA hybridizes with a binding sequence of the gene that is complementary to the target sequence.

The target sequence can be about 15 to about 25 nucleotides.

In one aspect, the present disclosure provides a computer program product comprising a non-transitory computer-readable medium having computer-executable code encoded therein, the computer-executable code adapted to be executed to implement a method for deducing a mutation in a gene, comprising: (a) providing a plurality of gene sequencing data sets at once, wherein each data set comprises: (i) a first sequencing trace of the gene without an exposure to a gene editing tool, (ii) a second sequencing trace of the gene with an exposure to the gene editing tool; and (iii) a target sequence of the gene, wherein the first and second sequencing traces each comprises a Sanger sequencing trace; and (b) for each gene sequencing data set, performing the steps comprising: (i) generating an initial set comprising (A) the first sequencing trace and (B) a plurality of predicted mutated traces of the first sequencing trace that each comprises an indel at a cut site of the target sequence; (ii) identifying a subset of the initial set by using a regression analysis, wherein a linear combination of each trace of the subset substantially resembles the second sequencing trace; and (iii) quantifying a frequency of each trace in the subset.

In one aspect, the present disclosure provides a method comprising determining, by a computer system, a first predicted sequence of a single nucleic acid molecule and a second predicted sequence of a single nucleic acid molecule, wherein the first and second predicted sequences are based on a first Sanger sequencing trace of a first plurality of nucleic acid molecules from a first sample, wherein the first and second predicted sequences each comprises an indel when compared to a second Sanger sequencing trace of a second plurality of nucleic acid molecules from a second sample, and wherein the indels of the first and second predicted sequences have a same size and a different nucleic acid sequence.

The first plurality of nucleic acid molecules can comprise nucleic acid molecules contacted with a nucleic acid editing tool. The nucleic acid editing tool can comprise a nuclease. The first sample and second sample can be different. In some cases, the nucleic acid editing tool did not contact the second plurality of nucleic acid molecules.

The determining can further comprise obtaining a first target sequence, wherein the target sequence is in the second plurality of nucleic acid molecules or is in the complement of sequence of the second plurality of nucleic acid molecules.

The determining can further comprise generating an initial set of predicted sequences of individual nucleic acid molecules based on the second Sanger sequencing trace. The initial set of predicted sequences of individual nucleic acid molecules can comprise insertions or deletions relative to the first target sequence. The insertions or deletions can be adjacent to a site in the first target sequence predicted to be cut by the nucleic acid editing tool.

The determining can further comprise comparing the initial set of predicted sequences of individual nucleic acid molecules to the first Sanger sequencing trace of the first plurality of nucleic acid molecules from the first sample. The comparing can comprise identifying a subset of the initial set of predicted sequences of individual nucleic acid molecules by performing a regression analysis. The regression analysis can comprise a non-negative least squares regression analysis. The non-negative least squares regression analysis can identify sequences of the initial set of predicted sequences of individual molecules, wherein the identified sequences in combination resemble the first Sanger sequencing trace. An R-squared value of the regression analysis can be at least 0.90, 0.91, 0.92, 0.93, 0.94, or 0.95.

The method can further comprise reporting to a user the first predicted sequence, the second predicted sequence, a first frequency of the first predicted sequence in the subset of the initial set, and a second frequency of the second predicted sequence in the subset of the initial set.

The first and/or second Sanger sequencing trace can be from capillary electrophoresis. The first and/or second Sanger sequencing trace can comprise a single electropherogram. The first target sequence can comprise a first guide RNA sequence for CRISPR/Cas, or a complement of the first guide RNA sequence for CRISPR/Cas.

The determining can further comprise obtaining a second target sequence, wherein the second target sequence comprises a second guide RNA sequence for CRISPR/Cas or a complement of the second guide RNA sequence for CRISPR/Cas.

The determining can further comprise obtaining a sequence of a donor nucleic acid for homology-directed repair.

The nucleic acid editing tool can comprises CRISPR/Cas. The nucleic acid editing tool can comprise more than one guide RNA sequence for a CRISPR/Cas. The nucleic acid editing tool can comprise a CRISPR/Cas comprising a single guide RNA. The nucleic acid editing tool can comprise a CRISPR/Cas and a donor nucleic acid for homology-directed repair.

The frequency of the predicted sequence can comprise a relative amount of the predicted sequence relative to other predicted sequences.

The initial set of predicted sequences can include at least 1, 10, 100, 1,000, 10,000, or 100,000 predicted sequences.

The determining can further comprise identifying an alignment window in the second Sanger sequencing trace, wherein the alignment window (i) comprises at least three nucleotides, (ii) is 5' of a predicted cut site in the first target sequence, and (iii) has an average Phred quality score of at least about 15, 20, 25, or 30.

The determining can further comprise aligning the first Sanger sequencing trace and second Sanger sequencing trace to the alignment window. A 3' end of the alignment window can be about 5, 10, 15, 20, or 25 nucleotides 5' of the predicted cut site in the first target sequence. The alignment window can comprise at least 10, 25, 50, 100, 150, or 200 nucleotides.

The determining can further comprise identifying an inference window comprising the predicted cut site in the second Sanger sequencing trace, wherein (i) a 5' end of the inference window is at about 10 to about 50 nucleotides 5' of the predicted cut site and (ii) a 3' end of the inference window at about 10 to about 200 nucleotides 3' of the predicted cut site. The 5' end of the inference window can be at 25 nucleotides 5' of the predicted cut site in the first target sequence, and the 3' end of the inference window can be at 100 nucleotides 3' of the predicted cut site in the first target sequence.

The identifying the inference window can comprise trimming the inference window based on a quality score of the second Sanger sequence trace. The inference window can comprise an average Phred quality score of at least 15, 20, 25, or 30. The inference window can be determined automatically without a human intervention.

The method can further comprise performing a regression analysis between the initial set of predicted sequences and the first Sanger sequencing trace at the inference window, thereby identifying a subset of predicted sequences from the initial set, wherein the identified subset of predicted sequences resembles the first Sanger sequencing trace.

The first plurality of nucleic acid molecules and the second plurality of nucleic acid molecules can be from a same cell type.

In one aspect, the present disclosure provides a computer program product comprising a non-transitory computer-readable medium having computer-executable code encoded therein, the computer-executable code adapted to be executed to implement a method comprising determining, by a computer system, a first predicted sequence of a single nucleic acid molecule and a second predicted sequence of a single nucleic acid molecule, wherein the first and second predicted sequences are based on a first Sanger sequencing trace of a first plurality of nucleic acid molecules from a first sample, wherein the first and second predicted sequences each comprises an indel when compared to a second Sanger sequencing trace of a second plurality of nucleic acid molecules from a second sample, and wherein the indels of the first and second predicted sequences have a same size and a different nucleic acid sequence.

In one aspect, the present disclosure provides a computer system comprising one or more processors to execute the computer program product comprising a non-transitory computer-readable medium having computer-executable code encoded therein, the computer-executable code adapted to be executed to implement a method comprising determining, by a computer system, a first predicted sequence of a single nucleic acid molecule and a second predicted sequence of a single nucleic acid molecule, wherein the first and second predicted sequences are based on a first Sanger sequencing trace of a first plurality of nucleic acid molecules from a first sample, wherein the first and second predicted sequences each comprises an indel when compared to a second Sanger sequencing trace of a second plurality of nucleic acid molecules from a second sample, and wherein the indels of the first and second predicted sequences have a same size and a different nucleic acid sequence.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A discloses SEQ ID NOS 1-2 and FIG. 1B discloses SEQ ID NOS 3 and 1, all respectively, in order of appearance;

FIG. 2A shows examples of a non-edited sequencing trace and an edited-sequencing trace used for deducing an edit in a nucleic acid. FIG. 2A discloses SEQ ID NOS 4-5, respectively, in order of appearance;

FIG. 2B shows an example of a discordance plot of a non-edited sequencing trace and an edited sequencing trace;

FIG. 2C shows an example of a distribution plot of frequencies of predicted indel sizes;

FIGS. 3E-3F show examples of sequences obtained from a prediction method and a next generation sequencing method of deducing an edit in a nucleic acid. FIG. 3E discloses SEQ ID NOS 6-7 and FIG. 3F discloses SEQ ID NOS 8-9, all respectively, in order of appearance;

FIG. 5B discloses SEQ ID NO: 10;

FIG. 6A discloses SEQ ID NOS 11-40, 40, 39, 41-46, 41, 47, 34, 33, 32, 31 and 30, FIG. 6B discloses SEQ ID NO: 11, FIG. 6C discloses SEQ ID NOS 11 and 48-49, and FIG. 6D discloses SEQ ID NOS 50-51, all respectively, in order of appearance;

FIG. 7 discloses SEQ ID NOS 52-53, respectively, in order of appearance;

FIG. 8A discloses SEQ ID NOS 52-81, FIG. 8B discloses SEQ ID NOS 52 and 82 and FIG. 8C discloses SEQ ID NOS 52-53 and 83-88, all respectively, in order of appearance;

FIG. 9 discloses SEQ ID NOS 89-90, respectively, in order of appearance;

FIG. 10A discloses SEQ ID NOS 89, 91-93, 92 and 94-115 and FIG. 10B discloses SEQ ID NOS 89 and 116-117, all respectively, in order of appearance;

FIG. 11 illustrates an example of a window of a GUI for a user to provide one or more batch files at once for a batch analysis of deducing an edit in a nucleic acid;

FIGS. 12A-12B illustrate examples of a window of a GUI for a user to provide one or more files for a batch analysis of deducing an edit in a nucleic acid. FIG. 12B discloses SEQ ID NOS 118-119, 10, 120, 52-53, 121, 89 and 122, respectively, in order of appearance;

FIG. 13 discloses SEQ ID NOS 123-125, 53, 52, 11 and 89, respectively, in order of appearance.

DETAILED DESCRIPTION

Overview

Figure 1A:
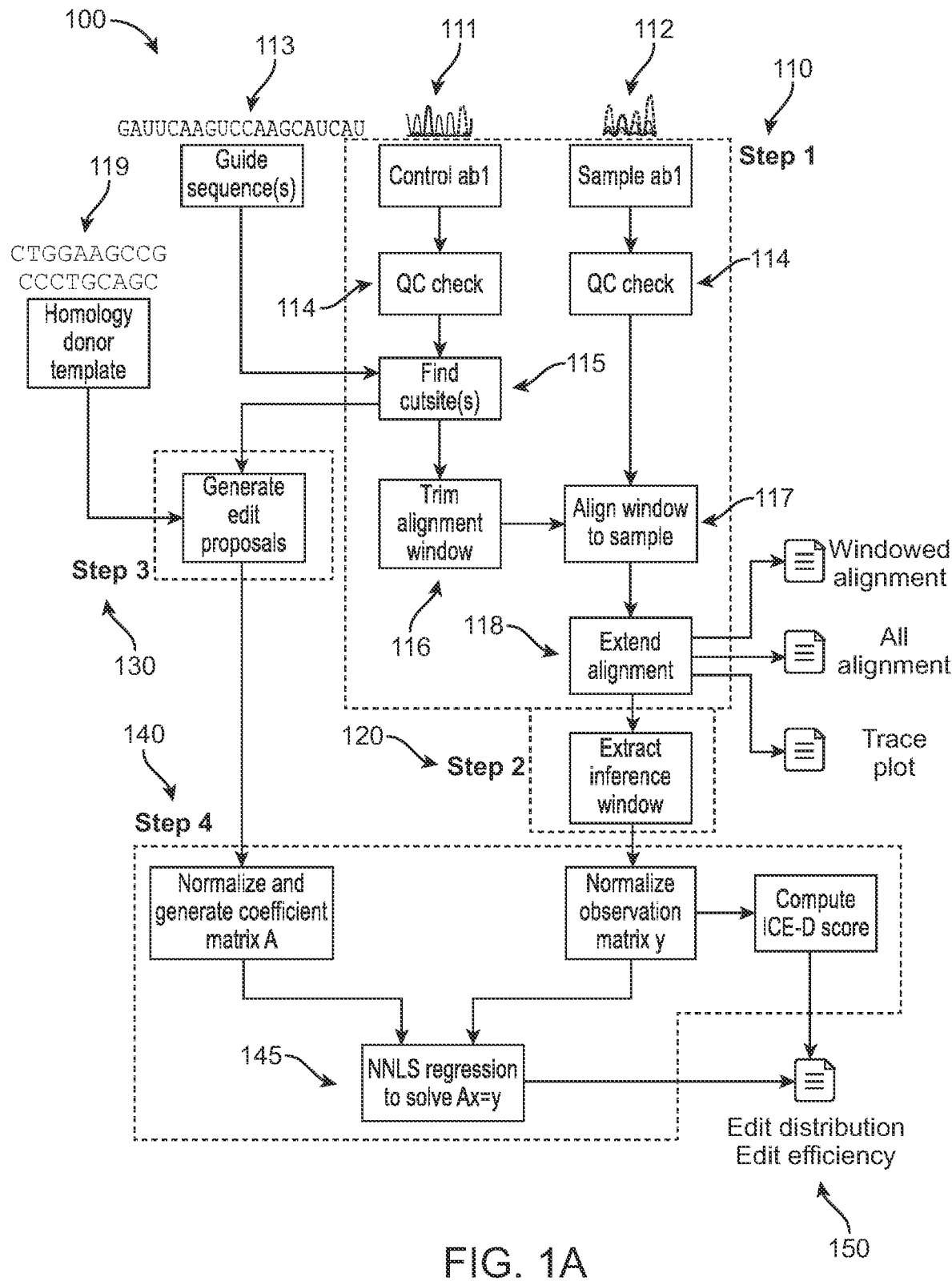
FIGS. 1A-1B show examples of a flow chart of a method of deducing a mutation in a nucleic acid.

In one aspect, the present disclosure provides a method comprising determining, by a computer system, a frequency of a predicted sequence of a single nucleic acid molecule based on a first Sanger sequencing trace of a first plurality of nucleic acid molecules from a first sample.

In another aspect, the present disclosure provides a method comprising determining, by a computer system, a first predicted sequence of a single nucleic acid molecule and a second predicted sequence of a single nucleic acid molecule. The first and second predicted sequences can be based on a first Sanger sequencing trace of a first plurality of nucleic acid molecules from a first sample. The first and second predicted sequences can each comprise an indel when compared to a second Sanger sequencing trace of a second plurality of nucleic acid molecules from a second sample. The indels of the first and second predicted sequences can have a same size and a different nucleic acid sequence.

In another aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool (e.g., a gene editing tool) (ii) a second sequencing trace of the nucleic acid with an exposure to the nucleic acid editing tool, and (iii) a target sequence of the nucleic acid (e.g., a target sequence of the gene editing tool in the gene). The first and second sequencing traces can each comprise a Sanger sequencing trace. The method can further comprise generating an initial set comprising (i) the first sequencing trace and (ii) a plurality of predicted mutated traces of the first sequencing trace that each comprises a change (e.g., an indel) at a cut site of the target sequence. The method can further comprise identifying a subset of the initial set by using a regression analysis. A linear combination of each trace of the subset can substantially resemble the second sequencing trace. The method can further comprise quantifying a frequency of each trace in the subset. In some cases, such a method can be implemented for determining an indel frequency in the nucleic acid (e.g., after exposure to the gene editing tool). In some cases, the frequency of each trace in the subset can refer to an abundance of each trace in the subset.

In one aspect, the present disclosure provides a method comprising determining, by a computer system, a plurality of predicted sequences of individual nucleic acid molecules in a first sample contacted by at least two different nucleic acid editing tools based on (i) a first Sanger sequencing trace of a first plurality of nucleic acid molecules from the first sample contacted by the at least two different nucleic acid editing tools and (ii) a second Sanger sequencing trace of a second plurality of nucleic acid molecules from a second sample not contacted by a nucleic acid editing tool.

In one aspect, the present disclosure provides a method comprising determining, by a computer system, a plurality of predicted sequences of individual nucleic acid molecules in a sample contacted by at least two different nucleic acid editing tools based on a Sanger sequencing trace of a plurality of nucleic acid molecules from the sample contacted by the at least two different nucleic acid editing tools.

In one aspect, the present disclosure provides a method comprising determining, by a computer system, a plurality of predicted sequences of individual nucleic acid molecules in a sample contacted by at least two different CRISPR/Cas complexes based on (i) at least two different guide sequences of the at least two different CRISPR/Cas complexes and (ii) a control Sanger sequencing trace of a plurality of nucleic acid molecules from a control sample not contacted by a CRISPR/Cas complex.

In one aspect, the present disclosure provides a method comprising determining, by a computer system, a base trace by trimming a Sanger sequencing trace of a plurality of nucleic acid molecules from a sample based on a first target sequence and a second target sequence. Each of the first and second target sequences can be in the plurality of nucleic acid molecules or can be in the complement of sequence of the plurality of nucleic acid molecules.

In another aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool, (ii) a second sequencing trace of the nucleic acid with an exposure to the nucleic acid editing tool, (iii) a first target sequence of the nucleic acid, and (iv) a second target sequence of the nucleic acid. The first and second sequencing traces can each comprise a Sanger sequencing trace. The first and second target sequences can be different. The method can further comprise identifying (i) a first cut site of the first target sequence in the first sequencing trace and (ii) and a second cut site of the second target sequence in the first sequencing trace. The first cut site can be upstream of the second cut site. The method can further comprise generating a base trace by subtracting the sequencing trace between the first and second cut sites from the first sequencing trace. The method can further comprise comparing the base trace and the second sequencing trace to thereby identify the change in the nucleic acid.

In one aspect, the present disclosure provides a method comprising determining, by a computer system, a predicted knockout sequence of a single nucleic acid molecule based on a first Sanger sequencing trace and a second Sanger sequencing trace. The predicted knockout sequence can comprise an indel when compared to the second Sanger sequencing trace. The indel of the predicted knockout sequence cannot be a multiple of three nucleotides and/or longer than a predetermined threshold length.

In another aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool, (ii) a second sequencing trace of the nucleic acid with an exposure to the nucleic acid editing tool, and (iii) a target sequence of the nucleic acid. The first and second sequencing traces can each comprise a Sanger sequencing trace. The method can further comprise generating an initial set comprising (i) the first sequencing trace and (ii) a plurality of predicted traces (e.g., predicted mutation traces) of the first sequencing trace that each comprises a change (e.g., an indel) at a cut site of the target sequence (e.g., a cut of the nucleic acid editing tool in the target sequence or in a strand opposite of the target sequence). The method can further comprise identifying a subset of the initial set by using a regression analysis. A linear combination of each trace of the subset can substantially resemble the second sequencing trace. The method can further comprise identifying a knockout trace from the subset. A length of the change in knockout trace (e.g., a length of the indel of the knockout trace) can (i) not be a multiple of three nucleotides, (ii) be longer than a threshold length, or (iii) both. The method can further comprise) calculating a knockout score of the nucleic acid editing tool. The knockout score can be a proportion of the knockout trace in the subset.

In one aspect, the present disclosure provides a method comprising determining, by a computer system, a predicted termination sequence of a single nucleic acid molecule based on a first Sanger sequencing trace and a second Sanger sequencing trace. The predicted termination sequence can comprise an indel when compared to the second Sanger sequencing trace. The indel of the predicted knockout sequence can yield a stop codon.

In another aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool, (ii) a second sequencing trace of the nucleic acid with an exposure to the nucleic acid editing tool, and (iii) a target sequence of the nucleic acid. The first and second sequencing traces can each comprise a Sanger sequencing trace. The method can further comprise generating an initial set comprising (i) the first sequencing trace and (ii) a plurality of predicted traces (e.g., a plurality of predicted mutated traces) of the first sequencing trace that each comprises a change (e.g., an indel) at a cut site of the target sequence. The method can further comprise identifying a subset of the initial set by using a regression analysis. A linear combination of each trace of the subset can substantially resemble the second sequencing trace. The method can further comprise identifying a termination trace from the subset. The termination trace can be from the plurality of predicted traces. The change (e.g., indel) in the termination trace can yield a stop codon.

In one aspect, the present disclosure provides a method comprising, by using a computer system, providing a plurality of nucleic acid sequencing data sets at once. Each data set can comprise a first Sanger sequencing trace, a second Sanger sequencing trace, and a first target sequence of a nucleic acid editing tool. The method can further comprise, for each data set, determining a subset of predicted sequences from an initial set of predicted sequences of individual nucleic acid molecules based on the second Sanger sequencing trace. The subset of predicted sequences in combination can resemble the first Sanger sequencing trace.

In another aspect, the present disclosure provides a method for determining (e.g., deducing) a change (e.g., edit, mutation) in a nucleic acid (e.g., gene), comprising providing a plurality of nucleic acid sequencing data sets at once. Each data set can comprises (i) a first sequencing trace of the nucleic acid without an exposure to a nucleic acid editing tool; (ii) a second sequencing trace of the nucleic acid with an exposure to the nucleic acid editing tool; and (iii) a target sequence of the nucleic acid (e.g., a target sequence of the nucleic acid editing tool). The first and second sequencing traces can each comprise a Sanger sequencing trace. The method can further comprise, for each nucleic acid sequencing data set, performing the steps comprising generating an initial set comprising (A) the first sequencing trace and (B) a plurality of predicted traces (e.g., a plurality of predicted mutated traces) of the first sequencing trace that each comprises a change (e.g., an indel) at a cut site of the target sequence. The performing the steps can further comprise identifying a subset of the initial set by using a regression analysis. A linear combination of each trace of the subset substantially can resemble the second sequencing trace. The performing the steps can further comprise quantifying a frequency of each trace in the subset.

In an aspect, the present disclosure provides a method of deducing a change (e.g., edit, mutation) in a nucleic acid (e.g., gene). In some embodiments, the method can comprise providing (i) a first sequencing trace of the nucleic acid without an exposure to a nucleic acid editing tool (i.e., a control file comprising the first sequencing trace), (ii) a second sequencing trace of the nucleic acid with an exposure to the nucleic acid editing tool (i.e., a sample file comprising the second sequencing trace), and (iii) at least one target sequence of the nucleic acid (i.e., guide sequence(s)). In some cases, the method can comprise providing a homology directed repair (HDR) template sequence. The first and second sequencing traces can be a Sanger sequencing trace. In some cases, two or more guide sequence(s) can be provided to analyze multiplex editing. The guide sequence(s) can be provided as nucleotide sequences (DNA or RNA). At least a portion of the sequencing trace in each of the control file and the sample file can be checked for quality control (QC). In some cases, an average Phred quality score of at least a portion of the first sequencing trace in the control file and/or at least a portion of the second sequencing trace in the sample file can be assessed. In an example, such an assessment can identify one or more regions in each of the first and/or second sequencing trace that has an average Phred quality score of at least about 15, 20, 25, or 30. Additionally, the guide sequence(s) can be used to identify at least one cut site in the first sequencing trace of the control file. The cut site can be a cut site of the nucleic acid editing tool.

The method can further comprise identifying an alignment window in the first sequencing trace in the control file. Identifying the alignment window can include trimming an end portion of the first sequencing trace of the control file to terminate upstream of the cut site (e.g., at 15 nucleotides upstream of the cut site). The alignment window can have an average Phred quality score of at least about 15, 20, 25, or 30, according to the QC check. The alignment window can be trimmed (shortened) such that the average Phred quality score is at least about 15, 20, 25, or 30. The alignment window can be upstream of the cut site. The second sequencing trace of the sample file can be aligned to the alignment window of the first sequencing trace of the control file. Ignoring poor quality nucleotides that are found at a beginning of a sequencing trace can improve reliability of the alignment method. Upon determining the alignment window, the first sequencing trace in the control file and the second sequencing trace of the sample file can be aligned by the alignment window. These two globally aligned sequences can be used for generating visualizations and performing interference and/or prediction calculations.

The method can further comprise identifying an inference window. The inference window can be a portion of the first sequencing trace. The inference window can be a portion of the second sequencing trace. The inference window can be a segment of the first and/or second sequencing trace to be used to deduce one or more indels by the gene editing tool. In an example, the inference window can start upstream (e.g., 25 nucleotides upstream) of the cut site and extend up to one or more nucleotides downstream (e.g., 100 nucleotides downstream) of the cut site. Additionally, a quality check of the inference window can be checked for QC. In some cases, the inference window can have an average Phred quality score of at least about 15, 20, 25, or 30, according to the QC check.

The method can further comprise generating an initial set comprising (i) the first sequencing trace of the control file and (ii) a plurality of predicted mutated traces of the first sequencing trace of the control file that each comprises an indel at the cut site of the target sequence. In some cases, the initial set can further comprise a sequencing trace that uses a portion of the HDR template sequence as an indel. In some cases, the initial set can be referred to as one or more edit proposals. The method can further comprise comparing one or more traces of the initial set and the second sequencing trace of the sample file at the inference window to predict a subset comprising one or more gene editing outcomes of the gene editing tool in the second sequencing trace of the sample file. In some cases, a regression analysis (e.g., non-negative least squares regression analysis or least absolute shrinkage and selection operator regression analysis) can be performed to compare the trace(s) of the initial set and the second sequencing trace of the sample file at the inference window. The regression analysis can identify the subset of the initial set, wherein a linear combination of each trace of the subset can substantially resemble the second sequencing trace of the sample file at the inference window.

The method can further comprise assessing a discordance signal. The discordance signal can show a level of disagreement between the non-edited, first sequencing trace of the control file and the edited, second sequencing trace of the sample file. In some cases, the discordance signal can show, base-by-base, an amount of signal that disagrees with a reference sequence derived from the non-edited, first sequencing trace. In some cases, the discordance signal can be a measure of a presence of multiple (e.g., 2, 3, or 4), overlapping peaks at a nucleobase. In some cases, a large and/or unexpected genomic edit may not be a part of the plurality of predicted mutated traces of the non-edited, first sequencing trace. In some cases, the discordance signal can range between 0 and 1, indicating a range between a low discordance to a high discordance. In an example, a reference polynucleotide sequence can be determined from the non-edited, first sequencing trace. The first and second sequencing traces can be compared against the reference polynucleotide sequence, base-by-base, in order to detect the amount of signal from each nucleobase of the first and second sequencing traces that disagrees with the control polynucleotide sequence. In some cases, the method can further comprise determining an average discordance signal between the control polynucleotide sequence and the edited, second sequencing trace within the inference window. In some cases, the discordance signal and/or the average discordance signal can be reported to the user.

The method can further comprise calculating a frequency of a plurality of indel sizes (e.g., −5, −4, −3, −2, −1, 0, +1, +2, +3, +4, +5 indels) of the subset of the initial set. In some cases, the method can further comprise generating a distribution of the plurality of indel sizes (e.g., a plot) of the subset. In some cases, the plot can be a bar graph. In some cases, the method can further comprise quantifying a frequency of each trace of each indel size of the plurality of indel sizes of the subset. In some cases, different traces comprising a same indel size can be grouped into one overall indel size. In some cases, different traces comprising a same indel size can be separated into different groups.

Definitions

The term "Sanger sequencing," as used here, can refer to a method of DNA sequencing based on selective incorporation of labeled chain-terminating dideoxynucleotides (ddNTPs) during in vitro DNA replication. Sequence information can be obtained using cycles of template denaturation, primer annealing and primer extension. Each round of primer extension can be stochastically terminated by incorporation of labeled ddNTPs. In the resulting mixture of end-labeled extension products, the label on the terminating ddNTP of any given fragment can correspond to the nucleotide identity of its terminal position. Sequence can be determined by high-resolution electrophoretic separation of the single-stranded, end-labeled extension products in a capillary-based polymer gel (e.g., capillary electrophoresis). Laser excitation of fluorescent labels as fragments of discrete lengths exit the capillary, coupled to four-color detection of emission spectra, can provide the readout that is represented in a Sanger sequencing "trace." Software can translate these traces into DNA sequences, while also generating error probabilities for one or more base-calls (e.g., one or more nucleobase calls). In some cases, Sanger sequencing can sequence a single DNA fragment; thus, the Sanger sequencing trace can have a single DNA fragment trace.

The Sanger sequencing trace can be an electropherogram. In some cases, the Sanger sequencing trace can include a single electropherogram, in the absence of any additional sequencing traces. The Sanger sequencing trace cannot be obtained from a massive parallel sequencing technique. The Sanger sequencing trace cannot be obtained from a NGS technique. The Sanger sequencing trace can include data sufficient to generate a Phred quality score (i.e., Q score) to the base-call(s).

The term "nucleic acid editing tool," "gene editing tool," or "genome editing tool," as used interchangeably herein, can refer to a nuclease or nuclease system that can induce a cleavage (e.g., a targeted cleavage, targeted break, or targeted cut) in a nucleic acid, e.g., a gene. The nuclease or nuclease system can comprise a polypeptide (e.g., an enzyme) and/or a ribozyme. Thus, the nucleic acid editing tool can generate a cleavage site, break site, or cut site in the nucleic acid, e.g., gene. In an example, the cleavage can be a targeted single strand break (SSB). In another example, the cleavage can be a targeted double-strand break (DSB). The nucleic acid editing tool can be, e.g., an endonuclease. Examples of the nucleic acid editing tool include meganucleases (MN), zinc finger nucleases (ZFN), transcription activator-like effector nucleases (TALEN), clustered regularly interspaced short palindromic repeat (CRISPR)-associated nucleases (e.g., CRISPR/Cas), one or more components of a RNA-induced silencing complex (RISC) (e.g., Argonaute), homologues thereof, and modified versions thereof.

In some cases, the CRISPR-associated nucleases can be a part of a fusion polypeptide. The fusion polypeptide can confer one or more additional activities selected from the group consisting of: methyltransferase activity, demethylase activity, dismutase activity, alkylation activity, depurination activity, oxidation activity, pyrimidine dimer forming activity, integrase activity, transposase activity, recombinase activity, polymerase activity (e.g., RNA reverse transcriptase activity), ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity (e.g., cytidine deaminase activity), lyase activity, isomerase activity, synthase activity, synthetase activity, or demyristoylation activity.

The nucleic acid editing tool can be useful in any in vitro or in vivo application in which it is desirable to modify a nucleic acid (e.g., DNA) in a site-specific (targeted) way, for example gene knock-out (KO), gene knock-in (KI), gene editing, gene tagging, etc., as used in, for example, gene therapy. Examples of uses of nucleic acid editing include gene therapies for antiviral, antipathogenic, and anticancer therapeutic; the production of genetically modified organisms in agriculture; the production (e.g., large scale production) of proteins by cells for therapeutic, diagnostic, or research purposes; the induction of induced pluripotent stem cells (iPS cells or iPSCs); and the targeting of genes of pathogens for deletion or replacement.

In some cases, two or more different nucleic acid editing tools may be two or more identical CRISPR-associated nucleases with two or more different guide RNAs.

The term "gene," as used herein, can refer to a nucleotide sequence that acts as a physical or functional unit of heredity. In some cases, a gene encodes fora polypeptide (e.g., protein). In some cases, a gene does not encode for a polypeptide. The gene can comprise DNA, RNA, or other nucleotides. A gene can comprise from about 100 to about 2 million bases.

The term "polynucleotide" or "nucleic acid," as used interchangeably herein, can refer to a polymeric form of nucleotides (e.g., ribonucleotides or deoxyribonucleotides) of any length. Thus, this term includes single-, double-, or multi-stranded DNA or RNA, genomic DNA, complementary DNA (cDNA), guide RNA (gRNA), messenger RNA (mRNA), DNA-RNA hybrids, or a polymer comprising purine and pyrimidine bases or other natural, chemically or biochemically modified, non-natural, or derivatized nucleotide bases. The term "oligonucleotide," as used herein, can refer to a polynucleotide of between about 5 and about 100 nucleotides of single- or double-stranded DNA or RNA. However, for the purposes of this disclosure, there can be no upper limit to the length of an oligonucleotide. In some cases, oligonucleotides can be known as "oligomers" or "oligos" and can be isolated from genes, or chemically synthesized by methods known in the art. The terms "polynucleotide" and "nucleic acid" should be understood to include single-stranded (such as sense or antisense) and double-stranded polynucleotides. Examples of nucleotides for DNA include cytosine (C), guanine (G), adenine (A), thymine (T), or modifications thereof. Examples of nucleotides for RNA include C, G, A, uracil (U), or modifications thereof.

The term "hybridization" or "hybridizing," as used herein, can refer to a process where completely or partially complementary polynucleotide strands come together under suitable hybridization conditions to form a double-stranded structure or region in which the two constituent strands are joined by hydrogen bonds. The term "partial hybridization," as used herein, can refer to a double-stranded structure or region containing one or more bulges or mismatches.

The term "cleavage" or "cleaving," as used herein, can refer to breaking of a covalent phosphodiester linkage in the ribosyl phosphodiester backbone of a polynucleotide. The term "cleavage" or "cleaving" can encompass both single-stranded breaks and double-stranded breaks. In some cases, a cleavage can result in the production of either blunt ends or staggered (or sticky) ends.

The term "CRISPR/Cas" or "CRISPR/Cas complex," as used herein, can refer to a ribonucleoprotein complex, e.g., a two component ribonucleoprotein complex, with guide RNA (gRNA) and a CRISPR-associated (Cas) endonuclease. In some cases, CRISPR/Cas comprises more than two components. The term "CRISPR" refers to the Clustered Regularly Interspaced Short Palindromic Repeats and the related system thereof. CRISPR can be used as an adaptive defense system that enables bacteria and archaea to detect and silence foreign nucleic acids (e.g., from viruses or plasmids). CRISPR can be adapted for use in a variety of cell types to allow for polynucleotide editing in a sequence-specific manner. In some cases, one or more elements of a CRISPR system can be derived from a type I, type II, or type III CRISPR system. In the CRISPR type II system, the guide RNA can interact with Cas and direct the nuclease activity of the Cas enzyme to a target region. The target region can comprise a "protospacer" and a "protospacer adjacent motif" (PAM), and both domains can be used for a Cas enzyme mediated activity (e.g., cleavage). The protospacer can be referred to as a target site (or a genomic target site). The gRNA can pair with (or hybridize) the opposite strand of the protospacer (binding site) to direct the Cas enzyme to the target region. The PAM site can refer to a short sequence recognized by the Cas enzyme and, in some cases, required for the Cas enzyme activity. The sequence and number of nucleotides for the PAM site can differ depending on the type of the Cas enzyme.

The term "Cas," as used herein, generally refers to a wild type Cas protein, a fragment thereof, or a mutant or variant thereof. The term "Cas," "enzyme Cas," "enzyme CRISPR," "protein CRISPR," or "protein Cas" can be used interchangeably throughout the present disclosure.

A Cas protein can comprise a protein of or derived from a CRISPR/Cas type I, type II, or type III system, which has an RNA-guided polynucleotide-binding or nuclease activity. Examples of suitable Cas proteins include Cas3, Cas4, Cas5, Cas5e (or CasD), Cash, Cas6e, Cas6f, Cas7, Cas8a1, Cas8a2, Cas8b, Cas8c, Cas9 (also known as Csn1 and Csx12), Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cu1966, homologues thereof, and modified versions thereof. In some cases, a Cas protein can comprise a protein of or derived from a CRISPR/Cas type V or type VI system, such as Cpf1l, C2c1, C2c2, homologues thereof, and modified versions thereof. In some cases, a Cas protein can be a catalytically dead or inactive Cas (dCas). In some cases, a Cas protein can have reduced or minimal nuclease activity (i.e., deactivated Cas, or dCas). In some cases, a Cas protein can be operatively coupled to one or more additional proteins, such as a nucleic acid polymerase. In an example, a Cas protein can be a dCas that is fused to a reverse transcriptase.

The term "guide RNA" or "gRNA," as used herein, can refer to an RNA molecule (or a group of RNA molecules collectively) that can bind to a Cas protein and aid in targeting the Cas protein to a specific location within a target polynucleotide (e.g., a DNA). A guide RNA can comprise a CRISPR RNA (crRNA) segment and a trans-activating crRNA (tracrRNA) segment. The term "crRNA" or "crRNA segment," as used herein, can refer to an RNA molecule or portion thereof that includes a polynucleotide-targeting guide sequence, a stem sequence, and, optionally, a 5'-overhang sequence. The term "tracrRNA" or "tracrRNA segment," can refer to an RNA molecule or portion thereof that includes a protein-binding segment (e.g., the protein-binding segment can be capable of interacting with a CRISPR-associated protein, such as a Cas9). The term "guide RNA" encompasses a single guide RNA (sgRNA), where the crRNA segment and the tracrRNA segment are located in the same RNA molecule. The term "guide RNA" also encompasses, collectively, a group of two or more RNA molecules, where the crRNA segment and the tracrRNA segment are located in separate RNA molecules. In some cases, the gRNA comprises nucleotides other than ribonucleotides.

The term "codon," as used herein, can refer to any group of three consecutive nucleotide bases in a given messenger RNA molecule, or coding strand of DNA that specifies a particular amino-acid. In some cases, the codon can be a starting or stopping signal for translation. The term codon also can refer to base triplets in a DNA strand.

The term "premature stop codon," as used herein, can refer to a codon generated by a mutation in a gene that results in a truncated, incomplete, and/or nonfunctional polypeptide product. In some cases, the premature stop codon can be a nonsense mutation. The term "nonsense mutation," as used herein, can refer to a point mutation that changes a codon corresponding to an amino acid to a stop codon. In some cases, the premature stop codon cannot be a nonsense mutation, but rather a new codon that is within an insertion mutation.

The term "regression analysis," as used herein, can refer to a method of using one or more mathematical/statistical analyses to model a relationship between a dependent variable and one or more independent variables, in which the dependent variable is dependent on the one or more independent variants. A regression analysis cancan utilize a linear model or a non-linear model. Examples of a regression analysis include, but are not limited to, linear regression, polynomial regression, logistic regression, quantile regression, ridge regression, least absolute shrinkage and selection operator (Lasso) regression, elastic net regression, principal components regression, partial least squares (PLS) regression, support vector regression, ordinal regression, Poisson regression, negative binomial regression, quasi Poisson regression, Cox regression, and Tobit regression. Other examples of a regression analysis cancan include Bayesian methods, percentage regression, least absolute deviations, nonparametric regression, and distance metric learning. In some cases, the regression analysis cancan utilize regularization, which generally refers to a process to solve overfitting problem of the statistical model by constraining one or more model parameters. Examples of the regularization-based regression analysis include ridge regression and Lasso regression.

In some cases, an acceptable R-squared value (i.e., a threshold R-squares value) of the regression analysis of the subset can be at least 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or more. In some cases, the acceptable R-squared value of the regression analysis of the subset can be at most 1, 0.99, 0.98, 0.97, 0.96, 0.95, 0.94, 0.93, 0.92, 0.91, 0.90, 0.89, 0.88, 0.87, 0.86, 0.85, 0.84, 0.83, 0.82, 0.81, 0.80, 0.79, 0.78, 0.77, 0.76, 0.75, 0.74, 0.73, 0.72, 0.71, 0.70, 0.69, 0.68, 0.67, 0.66, 0.65, 0.64, 0.63, 0.62, 0.61, 0.60, 0.59, 0.58, 0.57, 0.56, 0.55, 0.54, 0.53, 0.52, 0.51, 0.50, or less.

Methods for Determining an Indel Frequency

In an aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool (e.g., a gene editing tool) (ii) a second sequencing trace of the nucleic acid with an exposure to the nucleic acid editing tool, and (iii) a target sequence of the nucleic acid (e.g., a target sequence of the gene editing tool in the gene). The first and second sequencing traces can each comprise a Sanger sequencing trace. The method can further comprise generating an initial set comprising (i) the first sequencing trace and (ii) a plurality of predicted mutated traces of the first sequencing trace that each comprises a change (e.g., an indel) at a cut site of the target sequence. The method can further comprise identifying a subset of the initial set by using a regression analysis. A linear combination of each trace of the subset can substantially resemble the second sequencing trace. The method can further comprise quantifying a frequency of each trace in the subset. In some cases, such a method can be implemented for determining an indel frequency in the nucleic acid (e.g., after exposure to the gene editing tool).

The first sequencing trace, the second sequencing trace, and/or the target sequence can be provided by a user. The user can upload the first sequencing trace, the second sequencing trace, and/or the target sequence via a user interface on an electronic device (e.g., a personal computer, a mobile device, etc.). The user can send (e.g., via e-mail) such data to a centralized location (e.g., a centralized database). The method can further comprise reporting to the user the sequence and the frequency of each trace in the subset. The sequence and the frequency of each trace in the subset can be provided in a text format. Alternatively, or in addition to, the sequence and the frequency of each trace in the subset can be provided in a graph format (e.g., bar, line, dot, pie, histogram, etc.).

The first and second sequencing traces can be from capillary electrophoresis. Each of the first and second sequencing traces can comprise a single electropherogram. The first and second sequencing traces may not be obtained from a NGS method (e.g., amplicon sequencing or Amp-Seq, Solexa sequencing, Roche sequencing, Ion semiconductor sequencing, SOLiD sequencing, etc.). In some cases, each of the first and second sequencing traces may not be provided only in a text-based format that reads either nucleotide sequences or peptide sequences. In some cases, each of the first and second sequencing traces can be provided in a "AB1" (e.g., ABI, AB, AB!, AB1) or "SCF" data format. In some cases, each of the first and second sequencing traces may not be provided in a "FASTA" or "FASTQ" data format.

In some embodiments, the target sequence of the nucleic acid (e.g., gene) can be a target site of the nucleic acid editing tool, e.g., gene editing tool. In some cases, the nucleic acid editing tool, e.g., gene editing tool or a functional complex comprising the nucleic acid editing tool, can bind the target sequence of the nucleic acid. In some cases, the nucleic acid editing tool can bind a strand opposite of the target sequence in the nucleic acid (e.g., gene). The target sequence can be about 15 to about 25 nucleotides. In some cases, the target sequence can be at least about 15, 16, 17, 18, 19, 20, 21, 22, 23, 24, 25, or more nucleotides. In some cases, the target sequence can be at most about 25, 24, 23, 22, 21, 20, 19, 18, 17, 16, 15, or less nucleotides.

The plurality of predicted traces (e.g., predicted mutated traces) can include at least about 1, 10, 100, 1,000, 10,000, or 100,000 predicted traces. The plurality of predicted traces can include at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, or more predicted traces. The plurality of predicted traces can include at most about 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or less predicted traces.

In some embodiments, the method can use a mathematical and/or statistical optimization method to identify the subset from the initial set. In some cases, the method can use a regression analysis. Examples of the regression analysis can include Bayesian methods, percentage regression, least absolute deviations, nonparametric regression, distance metric learning, and non-negative least squares (NNLS) regression analysis.

In some cases, the method can use the NNLS regression analysis to identify the subset from the initial set. Alternatively, regularized least squares (RLS) regression analysis (e.g., Lasso regression or Ridge regression) can be used in place of non-negative least squares regression. For example, in Lasso regression, x can be solved for in the equation $Ax=y$, where A is a matrix composed of predicted sequencing traces (i.e., simulated traces) and y is an edited sequencing trace of an edited sample. Lasso regression can find a linear combination of the one or more of the simulated traces that best explains the edited sequencing trace of the edited sample. In comparison to NNLS regression that can overfit to the noise in sequencing data (e.g., Sanger sequencing data), Lasso regression can mitigate overfitting to the noise in Sanger sequencing data via regularization, e.g., L1 regularization. Lasso regression thus can produce more accurate results compared to alternative regression algorithms, such as NNLS. In Lasso regression, the relative prevalence of each edit proposal can be extracted from the vector of weights of the regression (x). In some cases, percentages of individual edits can be rounded to the nearest whole percentage point to reflect the model's underlying confidence about the accuracy of contribution estimations. The correlation between the regression derived and the observed edited sequencing trace ($r^2$) can measure the extent to which the edit proposals can explain the edited sequencing trace.

In some embodiments, the R-squared value of the regression analysis of the subset of the initial set can range between about 0.91 to about 0.99. In some cases, the R-squared value of the regression analysis of the subset can be at least 0.91, 0.92, 0.93, 0.94, 0.95, 0.96, 0.97, 0.98, 0.99, or more. In some cases, the R-squared value of the regression analysis of the subset can be at most 0.99, 0.98, 0.97, 0.96, 0.95, 0.94, 0.93, 0.92, 0.91, or less. In some cases, a plurality of subsets of the initial set can be generated. In such a case, a subset of the plurality of subsets with the highest R-squared value of the regression analysis can be selected. Alternatively, or in addition to, a subset of the plurality of subsets with the second, third, fourth, and/or fifth highest R-squared value of the regression analysis can be selected.

The subset of the initial set can include at least about 1, 10, 30, 50, or 100 predicted traces. The subset of the initial set can include at least about 1, 2, 3, 4, 5, 6, 7, 8, 9, 10, 20, 30, 40, 50, 60, 70, 80, 90, 100, 200, or more predicted traces.

The subset of the initial set can include at most about 200, 100, 90, 80, 70, 60, 50, 40, 30, 20, 10, 9, 8, 7, 6, 5, 4, 3, 2, or less predicted traces.

In some embodiments, the method can further comprise aligning the first and second sequencing traces to an alignment window of the first sequencing trace. The first and second sequencing traces can be aligned to the alignment window in order to identify the subset of the initial set. Aligning the first and second sequencing traces can help deduce one or more changes (e.g., edits, mutations) in the nucleic acid (e.g., gene) by the nucleic acid editing tool. The alignment window can be present in both the first and second sequencing traces. In some cases, a portion of the alignment window can be present in both the first and second sequencing traces. The alignment window can help determine a relative position of the second sequencing trace with respect to the first sequencing trace, thereby to deduce the change(s) (e.g., mutation(s)) in the nucleic acid by the nucleic acid editing tool. The sequencing trace in the alignment window can be at least a portion of the first and second sequencing traces that have not been changed (e.g., altered, modified, edited, mutated, etc.) by the nucleic acid editing tool. The alignment window can comprise at least about three nucleotides. In some cases, the alignment window can comprise at least about 3, 4, 5, 10, 15, 20, 25, 30, 35, 40, 45, 50 or more nucleotides. In some cases, the alignment window can comprise at most about 50, 45, 40, 35, 30, 25, 20, 15, 10, 5, 4, or less nucleotides. The alignment window can be upstream of the cut site of the nucleic acid editing tool in the first sequencing trace.

In some embodiments, the alignment window of the first sequencing trace can have an average Phred quality score of about 15, 20, 25, or 30. The Phred quality score can be a measure of the quality of the identification of the nucleotides generated by automated nucleic acid (e.g., DNA) sequencing (e.g., Sanger sequencing). The average Phred quality score can be an average of the Phred quality score of each nucleotide in the alignment window. In some cases, the alignment window can have an average Phred quality score of at least 15, 20, 25, 30, or more. In some cases, the alignment window can have an average Phred quality score of at most 30, 25, 20, 15, or less. At least one nucleotide in the alignment window can have a Phred quality score of about 15, 20, 25, or 30. In some cases, at least one nucleotide in the alignment window can have a Phred quality of at least 15, 20, 25, 30, or more. In some cases, at least one nucleotide in the alignment window can have a Phred quality of at most 30, 25, 20, 15, or less.

In some embodiments, the method can further comprise selecting a 3' end of the alignment window at about 5, 10, 15, 20, or 25 nucleotides upstream of the cut site, wherein a 5' end of the alignment window is upstream of the 3' end of the alignment window. In some cases, the 3' end of the alignment window can be at least about 5, 10, 15, 20, 25, 30, or more nucleotides upstream of the cut site. In some cases, the 3' end of the alignment window can be at most about 30, 25, 20, 15, 10, 5, or less nucleotides upstream of the cut site In some embodiments, in some cases, the alignment window can comprise at least about 10, 25, 50, 100, 150, or 200 nucleotides. In some cases, the alignment window can comprise at least about 10, 25, 50, 100, 150, 200, or more nucleotides. In some cases, the alignment window can comprise at most about 200, 150, 100, 50, 25, 10, or less nucleotides.

In some embodiments, the method can further comprise aligning the plurality of mutated traces of the first sequencing trace and the second sequencing trace to the alignment window. Each of the plurality of predicted traces (e.g., predicted mutated traces) of the first sequencing trace can comprise the alignment window. The plurality of predicted traces of the first sequencing trace and the second sequencing trace can be aligned to the alignment window in order to identify the subset of the initial set.

In some embodiments, the method can further comprise, performing the regression analysis between the initial set and the second sequencing trace at an inference window of the first sequencing trace to identify the subset. Comparison of the initial set to the second sequencing trace can help deduce the change(s) (e.g., mutation(s)) in the nucleic acid (e.g., gene) by the nucleic acid editing tool that can result in the second sequencing trace of the nucleic acid. The inference window can comprise at least three nucleotides. In some cases, the inference window can comprise at least about 3, 4, 5, 10, 15, 20, 25, 30, 35, 40, 45, 50 or more nucleotides. In some cases, the inference window can comprise at most about 50, 45, 40, 35, 30, 25, 20, 15, 10, 5, 4, or less nucleotides. The inference window can comprise a 5' end that is upstream of the cut site of the nucleic acid editing tool in the gene. The inference window can comprise a 3' end that is downstream of the cut site of the nucleic acid editing tool in the gene. The cut site can be disposed between the 5' end and the 3' end of the inference window.

In some embodiments, in some cases, the method can further comprise selecting (i) the 5' end of the inference window at about 10 to about 50 nucleotides upstream of the cut site and (ii) the 3' end of the inference window at about 10 to about 200 nucleotides downstream of the cut site. In some cases, the 5' end of the inference window can be at least about 10, 15, 20, 25, 30, 35, 40, 45, 50 or more nucleotides upstream of the cut site. In some cases, the 5' end of the inference window can be at most about 50, 45, 40, 35, 30, 25, 20, 15, 10, or less nucleotides upstream of the cut site. In some cases, the 5' end of the inference window can be at 25 nucleotides upstream of the cut site. In some cases, the 3' end of the inference window can be at least about 10, 20, 40, 60, 80, 100, 150, 200, or more nucleotides downstream of the cut site. In some cases, the 3' end of the inference window can be at most about 200, 150, 100, 80, 60, 40, 20, 10, or less nucleotides downstream of the cut site. In some cases, the 3' end of the inference window can be at 100 nucleotides downstream of the cut site.

In some embodiments, the method can further comprise identifying the inference window such that the inference window has an average Phred quality score of at least 15, 20, 25, or 30. The method can comprise identifying the inference window of one or more of traces in the initial set and/or the second sequencing trace such that the inference window has an average Phred quality score of at least 15, 20, 25, or 30. In some cases, the inference window can have an average Phred quality score of at least 15, 20, 25, 30, or more. In some cases, the inference window can have an average Phred quality score of at most 30, 25, 20, 15, or less. At least one nucleotide in the inference window can have a Phred quality score of about 15, 20, 25, or 30. In some cases, at least one nucleotide in the inference window can have a Phred quality of at least 15, 20, 25, 30, or more. In some cases, at least one nucleotide in the inference window can have a Phred quality of at most 30, 25, 20, 15, or less.

In some embodiments, each of the plurality of predicted traces (e.g., predicted mutated traces) of the first sequencing trace can comprise a change (e.g., an indel). The indel can be an insertion and/or a deletion of one or more nucleotides in the nucleic acid. The indel can be disposed at or adjacent to the cut site of the nucleic acid editing tool in the first sequencing trace. The indel can be disposed at or adjacent to the 5' end and/or the 3' end of the cut site. The indel can occur via number of pathways. Examples of such pathways include non-homologous end joining (NHEJ) and homology-directed repair (HDR). In some cases, the indel can range from about 1 to about 100 nucleotides. In some cases, the indel can range from about 1 to about 50 nucleotides. In some cases, the indel can be at least about 1, 2, 3, 4, 5, 6, 7, 8, 9, 10, 15, 20, 25, 30, 35, 40, 50, 60, 70, 80, 90, 100, or more nucleotides. In some cases, the indel can be at most about 100, 90, 80, 70, 60, 50, 40, 35, 30, 25, 20, 15, 10, 9, 8, 7, 6, 5, 4, 3, 2, or less nucleotide(s).

In some embodiments, the alignment window and/or the inference window can be identified automatically (e.g., by a computer system). In some cases, the identifying of the inference window can be performed automatically in the absence of a human intervention (e.g., a manual input or selection by the user who provides the first sequencing data and the second sequencing data). Examples of such human intervention includes selecting (i) the 5' and/or the 3' end of the alignment window, (ii) a length of the inference window, (iii) a number of nucleotides between the cut site and the 5' or the 3' end of the inference window, and (iv) a range of the indel size.

In some embodiments, the first sequencing trace of the nucleic acid (e.g., gene) can be from a first cell without the exposure to the nucleic acid editing tool, and the second sequencing trace of the nucleic acid (e.g., gene) is from a second cell with the exposure to the nucleic acid editing tool, wherein the first and second cells are the same type of cells. In some cases, such cells may not have been genetically modified prior to the exposure to the nucleic acid editing tool. In some cases, such cells can have been genetically modified prior to the exposure to the nucleic acid editing tool.

The first and/or second cell can be ex vivo (e.g., in vitro) when exposed (e.g., contacted) by the nucleic acid editing tool. The first and/or second cell can be in vivo when exposed (e.g., contacted) by the nucleic acid editing tool.

In some embodiments, the nucleic acid editing tool can be a nuclease. In some cases, the nuclease can be selected from the group consisting of CRISPR nuclease, TALEN, ZFN, MN, and Argonaute. In some cases, the CRISPR nuclease can be selected from the group consisting of Cas9, C2c1, C2c3, and Cpf1. In an example, the method can comprise using CRISPR/Cas9 with a gRNA, and a portion of the gRNA can hybridize with a binding sequence of the gene that is complementary to the target sequence of the CRISPR/Cas9 gene editing tool. In such a case, the target sequence can be substantially the same as a portion (e.g., a CRISPR RNA or crRNA) of the gRNA of the CRISPR/Cas system that is responsible for the hybridization to the gene. In such a case, the method can provide inference of CRISPR edits from Sanger sequencing trace data.

In some embodiments, the method can further comprise calculating an edit efficiency of the nucleic acid editing tool. In some cases, the edit efficiency can be a portion of traces in the subset comprising a change (e.g., a non-wild type nucleic acid sequence that comprises an indel). In some cases, the edit efficiency can range between 0 to 1. In some cases, an edit efficiency of 0 from the range between 0 to 1 can indicate that there is no change (e.g., edit mutation) of the nucleic acid by the nucleic acid editing tool. In some cases, an edit efficiency of 1 from the range between 0 to 1 can indicate that each trace in the subset comprises an indel. In some cases, the edit efficiency can be at least about 0.01, 0.05, 0.1, 0.2, 0.3, 0.4, 0.5, 0.6, 0.7, 0.8, 0.9, or more. In some cases, the edit efficiency can be at most about 0.9, 0.8, 0.7, 0.6, 0.5, 0.4, 0.3, 0.2, 0.1, 0.05, 0.01 or less. In some embodiments, the edit efficiency can range between 0 percent (%) to 100%. In some cases, an edit efficiency of 0% from the range between 0% to 100% can indicate that there is no change of the nucleic acid by the nucleic acid editing tool. In some cases, an edit efficiency of 100% from the range between 0% to 100% can indicate that each trace in the subset comprises a change (e.g., an indel). In some cases, the edit efficiency can be at least about 0.1%, 0.5%, 1%, 5%, 10%, 20%, 30%, 40%, 50%, 60%, 70%, 80%, 90%, or more. In some cases, the edit efficiency can be at most about 90%, 80%, 70%, 60%, 50%, 40%, 30%, 20%, 10%, 5%, 1%, 0.5%, 0.1% or less. In some cases, the edit efficiency can be reported to the user.

In some embodiments, the method can further comprise providing a HDR template sequence. In some cases, the HDR template sequence can be provided by the user. In some cases, the HDR template sequence can be a donor sequence. In some cases, the HDR template can comprise two homology arms and a nucleic acid template that is disposed between the two homology arms. In some cases, the homology arm can be at least 10, 20, 30, 40, 50, 60, 80, 100, or more nucleotides in length. In some cases, the homology arm can be at most 100, 80, 60, 50, 40, 30, 20, 10, or less nucleotides in length. In some cases, the nucleic acid template can be at least 1, 2, 3, 4, 5, 10, 20, 30, 40, 50, 60, 80, 100, or more nucleotides in length. In some cases, the nucleic acid template can be at most 100, 80, 60, 50, 40, 30, 20, 10, 5, 4, 3, 2, or less nucleotides in length.

In some embodiments, the method can further comprise identifying a HDR trace in the subset, wherein the HDR trace comprises the nucleic acid template of the HDR template sequence as a change (e.g., an indel). In some embodiments, the method can further comprise calculating a HDR score. The HDR score can be a proportion of the HDR trace in the subset. In some cases, the method can further comprise reporting the HDR score to the user. In some cases, the HDR score can be referred to as a knockin score.

Computer System for Determining an Indel Frequency

Another aspect of the present disclosure provides a computer system for deducing a change (e.g., edit, mutation) in a nucleic acid. The computer system can include a computer program product comprising a non-transitory computer-readable medium having computer-executable code encoded therein, the computer-executable code adapted to be executed to implement a method for deducing the change in the nucleic acid. The computer-executable code can be adapted to be executed to implement one or more methods provided herein, such as, for example, the method for determining an indel frequency.

Methods for Analyzing Multiplex Editing

In an aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool, (ii) a second sequencing trace of the nucleic acid with an exposure to the nucleic acid editing tool, (iii) a first target sequence of the nucleic acid, and (iv) a second target sequence of the nucleic acid. The first and second sequencing traces can each comprise a Sanger sequencing trace. The first and second target sequences can be different. The method can further comprise identifying (i) a first cut site of the first target sequence in the first sequencing trace and (ii) and a second cut site of the second target sequence in the first sequencing trace. The first cut site can be upstream of the second cut site. The method can further comprise generating a base trace by subtracting the sequencing trace between the first and second cut sites from the first sequencing trace. The method can further comprise comparing the base trace and the second sequencing trace to thereby identify the change in the nucleic acid.

The method disclosed herein can be implemented for analyzing multiplex editing, wherein two or more polynucleotide sequences are utilized to bring two or more nucleic acid editing tools (e.g., gene editing tools) of a same type or different types to two or more different target sites of the nucleic acid (e.g., gene). Such a method for analyzing multiplex editing can implement one or more methods provided herein, such as, for example, the method for determining an indel frequency.

In some embodiments, a 3' end of the first cut site of the first target sequence of the nucleic acid (e.g., gene) can be upstream of a 5' end of the second cut site of the second target sequence of the nucleic acid. In some embodiments, the control sequence can be a continuous sequencing trace in the absence of the trace between the first and second cut sites from the first sequencing trace. Thus, in the base trace, the first cut site can be adjacent to the second cut site.

In some embodiments, the method can further comprise generating an initial set comprising (i) the base trace and (ii) a plurality of predicted traces (e.g., predicted mutated traces) of the base trace that each comprises a change (e.g., an indel) at the first or second cut site. The plurality of predicted traces (e.g., predicted mutated traces) can include at least about 1, 10, 100, 1,000, 10,000, or 100,000 predicted traces. The plurality of predicted traces can include at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, or more predicted traces. The plurality of predicted traces can include at most about 100,000, 90,000, 80,000, 70,000, 60,000, 50,000, 40,000, 30,000, 20,000, 10,000, 9,000, 8,000, 7,000, 6,000, 5,000, 4,000, 3,000, 2,000, 1,000, 900, 800, 700, 600, 500, 400, 300, 200, 100, 90, 80, 70, 60, 50, 40, 30, 20, 10, 9, 8, 7, 6, 5, 4, 3, 2, or less predicted traces.

In some embodiments, the method can further comprise identifying a subset of the initial set by using a regression analysis, wherein a linear combination of each trace of the subset substantially resembles the second sequencing trace. The method can implement one or more methods of the regression analysis provided herein, such as, for example, the NNLS regression analysis or the Lasso regression analysis for determining an indel frequency in the nucleic acid. In some cases, an R-squared value of the regression analysis of the subset is at least 0.90, 0.91, 0.92, 0.93, 0.94, or 0.95.

The subset of the initial set can include at least about 1, 10, 30, 50, or 100 predicted traces. The subset of the initial set can include at least about 1, 2, 3, 4, 5, 6, 7, 8, 9, 10, 20, 30, 40, 50, 60, 70, 80, 90, 100, 200, or more predicted traces. The subset of the initial set can include at most about 200, 100, 90, 80, 70, 60, 50, 40, 30, 20, 10, 9, 8, 7, 6, 5, 4, 3, 2, or less predicted traces.

In some embodiments, the method can further comprise quantifying a frequency of each trace in the subset of the initial set. In some cases, when the first and second sequencing traces and the first and second target sequences are provided by a user, the method can further comprise reporting to the user the sequence and the frequency of each trace in the subset.

In some embodiments, the method can further comprise aligning the base trace and the second sequencing trace to an alignment window of the base trace. The base trace and the second sequencing trace can be aligned to the alignment window in order to identify the subset of the initial set. Aligning the base trace and the second sequencing trace can help deduce one or more mutations in the nucleic acid (e.g., gene) by the nucleic acid editing tool in the multiplex editing. The alignment window can be present in both the base trace and the second sequencing trace. In some cases, a portion of the alignment window can be present in both the base trace and the second sequencing trace. The alignment window can help determine a relative position of the second sequencing trace with respect to the base trace, thereby to deduce the mutation(s) in the nucleic acid by the nucleic acid editing tool in the multiplex editing. The sequencing trace in the alignment window can be at least a portion of the base trace and the second sequencing trace that have not been changed (e.g., altered, modified, edited, mutated, etc.) by the multiplex editing. The alignment window can comprise at least about three nucleotides. In some cases, the alignment window can comprise at least about 3, 4, 5, 10, 15, 20, 25, 30, 35, 40, 45, 50 or more nucleotides. In some cases, the alignment window can comprise at most about 50, 45, 40, 35, 30, 25, 20, 15, 10, 5, 4, or less nucleotides. The alignment window can be upstream of the first cut site of the nucleic acid editing tool in the base trace, thus also in the first sequencing trace.

In some embodiments, the alignment window of the base trace can have an average Phred quality score of about 15, 20, 25, or 30. In some cases, the alignment window can have an average Phred quality score of at least 15, 20, 25, 30, or more. In some cases, the alignment window can have an average Phred quality score of at most 30, 25, 20, 15, or less. At least one nucleotide in the alignment window can have a Phred quality score of about 15, 20, 25, or 30. In some cases, at least one nucleotide in the alignment window can have a Phred quality of at least 15, 20, 25, 30, or more. In some cases, at least one nucleotide in the alignment window can have a Phred quality of at most 30, 25, 20, 15, or less.

In some embodiments, the method can further comprise aligning the plurality of predicted traces (e.g., predicted mutated traces) of the base trace and the second sequencing trace to the alignment window. Each of the plurality of predicted traces of the base trace can comprise the alignment window. The plurality of predicted traces of the base trace and the second sequencing trace can be aligned to the alignment window in order to identify the subset of the initial set.

In some embodiments, the method can further comprise selecting a 3' end of the alignment window at about 5, 10, 15, 20, or 25 nucleotides upstream of the cut first site, wherein a 5' end of the alignment window is upstream of the 3' end of the alignment window. In some cases, the 3' end of the alignment window can be at least about 5, 10, 15, 20, 25, 30, or more nucleotides upstream of the first cut site. In some cases, the 3' end of the alignment window can be at most about 30, 25, 20, 15, 10, 5, or less nucleotides upstream of the first cut site In some embodiments, in some cases, the alignment window can comprise at least about 10, 25, 50, 100, 150, or 200 nucleotides. In some cases, the alignment window can comprise at least about 10, 25, 50, 100, 150, 200, or more nucleotides. In some cases, the alignment window can comprise at most about 200, 150, 100, 50, 25, 10, or less nucleotides.

In some embodiments, the method can further comprise, performing the regression analysis between the initial set and the second sequencing trace at an inference window of the base trace to identify the subset. Comparison of the initial set to the second sequencing trace can help deduce the change(s) (e.g., mutation(s)) in the nucleic acid (e.g., gene) by the nucleic acid editing tool that can result in the second sequencing trace of the nucleic acid. The inference window can comprise at least three nucleotides. In some cases, the inference window can comprise at least about 3, 4, 5, 10, 15, 20, 25, 30, 35, 40, 45, 50 or more nucleotides. In some cases, the inference window can comprise at most about 50, 45, 40, 35, 30, 25, 20, 15, 10, 5, 4, or less nucleotides. The inference window can comprise a 5' end that is upstream of the first cut site of the nucleic acid editing tool in the gene. The inference window can comprise a 3' end that is downstream of the second cut site of the nucleic acid editing tool in the gene. The first cut site and the second cut site can be disposed between the 5' end and the 3' end of the inference window of the base trace.

In some embodiments, in some cases, the method can further comprise selecting (i) the 5' end of the inference window at about 10 to about 50 nucleotides upstream of the first cut site and (ii) the 3' end of the inference window at about 10 to about 200 nucleotides downstream of the second cut site. In some cases, the 5' end of the inference window can be at least about 10, 15, 20, 25, 30, 35, 40, 45, 50 or more nucleotides upstream of the first cut site. In some cases, the 5' end of the inference window can be at most about 50, 45, 40, 35, 30, 25, 20, 15, 10, or less nucleotides upstream of the first cut site. In some cases, the 5' end of the inference window can be at 25 nucleotides upstream of the first cut site. In some cases, the 3' end of the inference window can be at least about 10, 20, 40, 60, 80, 100, 150, 200, or more nucleotides downstream of the second cut site. In some cases, the 3' end of the inference window can be at most about 200, 150, 100, 80, 60, 40, 20, 10, or less nucleotides downstream of the second cut site. In some cases, the 3' end of the inference window can be at 100 nucleotides downstream of the second cut site.

In some embodiments, the method can further comprise identifying the inference window such that the inference window has an average Phred quality score of at least 15, 20, 25, or 30. The method can comprise identifying the inference window of one or more of traces in the initial set and/or the second sequencing trace such that the inference window has an average Phred quality score of at least 15, 20, 25, or 30. In some cases, the inference window can have an average Phred quality score of at least 15, 20, 25, 30, or more. In some cases, the inference window can have an average Phred quality score of at most 30, 25, 20, 15, or less. At least one nucleotide in the inference window can have a Phred quality score of about 15, 20, 25, or 30. In some cases, at least one nucleotide in the inference window can have a Phred quality of at least 15, 20, 25, 30, or more. In some cases, at least one nucleotide in the inference window can have a Phred quality of at most 30, 25, 20, 15, or less.

In some embodiments, each of the plurality of predicted traces (predicted mutated traces) of the base trace can comprise a change (e.g., an indel). In some cases, the indel can be an insertion and/or a deletion of one or more nucleotides in the nucleic acid. The indel can be disposed at or adjacent to the first cut site or the second cut site in the base trace. The indel can be disposed at or adjacent to the 5' end and/or the 3' end of the first cut site or the second cut site in the base trace. In some cases, the indel can range from about 1 to about 100 nucleotides. In some cases, the indel can range from about 1 to about 50 nucleotides. In some cases, the indel can be at least about 1, 2, 3, 4, 5, 6, 7, 8, 9, 10, 15, 20, 25, 30, 35, 40, 50, 60, 70, 80, 90, 100, or more nucleotides. In some cases, the indel can be at most about 100, 90, 80, 70, 60, 50, 40, 35, 30, 25, 20, 15, 10, 9, 8, 7, 6, 5, 4, 3, 2 or less nucleotide(s).

In some embodiments, the initial set can further comprise (i) the first sequencing trace and (ii) an additional plurality of predicted traces (e.g., predicted mutated traces) of the first sequencing trace that each comprises a change (e.g., an indel) at the first cut site or the second cut site. Such additional plurality of predicted traces of the first sequencing trace may not have both an indel at the first cut site and a different indel at the second cut site. In some cases, the method can further comprise (i) aligning the second sequencing trace to the first sequencing trace (and to the plurality of predicted traces of the first sequencing trace), and then (ii) performing the regression analysis between the initial set and the second sequencing trace to identify the subset.

Computer System for Analyzing Multiplex Editing

Another aspect of the present disclosure provides a different computer system for deducing a change (e.g., edit, mutation) in a nucleic acid (e.g., gene). The computer system can include a computer program product comprising a non-transitory computer-readable medium having computer-executable code encoded therein, the computer-executable code adapted to be executed to implement a method for deducing the change in a nucleic acid. The computer-executable code can be adapted to be executed to implement the methods provided herein, such as, for example, the method for analyzing multiplex editing. Additionally, the computer-executable code can be adapted to be executed to implement the methods provided herein, such as, for example, the method for determining an indel frequency.

Methods for Determining a Knockout Score

In an aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool, (ii) a second sequencing trace of the nucleic acid with an exposure to the nucleic acid editing tool, and (iii) a target sequence of the nucleic acid. The first and second sequencing traces can each comprise a Sanger sequencing trace. The method can further comprise generating an initial set comprising (i) the first sequencing trace and (ii) a plurality of predicted traces (e.g., predicted mutation traces) of the first sequencing trace that each comprises a change (e.g., an indel) at a cut site of the target sequence (e.g., a cut of the nucleic acid editing tool in the target sequence or in a strand opposite of the target sequence). The method can further comprise identifying a subset of the initial set by using a regression analysis. A linear combination of each trace of the subset can substantially resemble the second sequencing trace. The method can further comprise identifying a knockout trace from the subset. A length of the change in knockout trace (e.g., a length of the indel of the knockout trace) can (i) not be a multiple of three nucleotides, (ii) be longer than a threshold length, or (iii) both. The method can further comprise) calculating a knockout score of the nucleic acid editing tool. The knockout score can be a proportion of the knockout trace in the subset.

In some embodiments, the threshold length of the change (e.g., indel) can be at least about 10, 11, 12, 13, 14, 15, 16, 17, 18, 19, 20, 21, 22, 23, 24, or 25 nucleotides. In some embodiments, the threshold length of the change can be at most about 25, 24, 23, 22, 21, 20, 19, 18, 17, 16, 15, 14, 13, 12, 11, or less nucleotides.

In some embodiments, the knockout score can range between 0 to 1. In some cases, a knockout score of 0 from the range between 0 to 1 can indicate that there is no knockout trace in the subset. In some cases, a knockout score of 1 from the range between 0 to 1 can indicate that each trace in the subset is a knockout trace. In some cases, the knockout score can be at least about 0.01, 0.05, 0.1, 0.2, 0.3, 0.4, 0.5, 0.6, 0.7, 0.8, 0.9, or more. In some cases, the knockout score can be at most about 0.9, 0.8, 0.7, 0.6, 0.5, 0.4, 0.3, 0.2, 0.1, 0.05, 0.01 or less. In some embodiments, the knockout score can range between 0% to 100%. In some cases, a knockout score of 0% from the range between 0% to 100% can indicate that there is no knockout trace in the subset. In some cases, a knockout score of 100% from the range between 0% to 100% can indicate that each trace in the subset is a knockout trace. In some cases, the knockout score can be at least about 0.1%, 0.5%, 1%, 5%, 10%, 20%, 30%, 40%, 50%, 60%, 70%, 80%, 90%, or more. In some cases, the knockout score can be at most about 90%, 80%, 70%, 60%, 50%, 40%, 30%, 20%, 10%, 5%, 1%, 0.5%, 0.1% or less.

In some cases, when the first and second sequencing traces and the target sequences are provided by a user, the method can further comprise reporting to the user the knockout score of the gene editing tool.

In some embodiments, the method can be implemented for determining a knockout score of a nucleic acid editing tool, wherein one or more genes of interest have been made inoperative (or ablated) by the gene editing tool. Such a method for determining the knockout score can implement one or more methods provided herein, such as, for example, the method for determining an indel frequency and/or the method for analyzing multiplex editing.

Computer System for Determining a Knockout Score

Another aspect of the present disclosure provides a different computer system for deducing a change (e.g., edit, mutation) in a nucleic acid (e.g., gene). The computer system can include a computer program product comprising a non-transitory computer-readable medium having computer-executable code encoded therein, the computer-executable code adapted to be executed to implement a method for deducing the change in a nucleic acid. The computer-executable code can be adapted to be executed to implement the methods provided herein, such as, for example, the method for determining a knockout score. Additionally, the computer-executable code can be adapted to be executed to implement the methods provided herein, such as, for example, the method for determining an indel frequency and/or the method for analyzing multiplex editing.

Methods for Identifying a Stop Codon

In an aspect, the present disclosure provides a method for determining (e.g., deducing) a change (e.g., edit, mutation) in a nucleic acid (e.g., gene), comprising providing (i) a first sequencing trace of the nucleic acid without an exposure to a nucleic acid editing tool, (ii) a second sequencing trace of the nucleic acid with an exposure to the nucleic acid editing tool, and (iii) a target sequence of the nucleic acid. The first and second sequencing traces can each comprise a Sanger sequencing trace. The method can further comprise generating an initial set comprising (i) the first sequencing trace and (ii) a plurality of predicted traces (e.g., a plurality of predicted mutated traces) of the first sequencing trace that each comprises a change (e.g., an indel) at a cut site of the target sequence. The method can further comprise identifying a subset of the initial set by using a regression analysis. A linear combination of each trace of the subset can substantially resemble the second sequencing trace. The method can further comprise identifying a termination trace from the subset. The termination trace can be from the plurality of predicted traces. The change (e.g., indel) in the termination trace can yield a stop codon.

The stop codon can be at or near the cut site. In some cases, the stop codon can be a result of (i) an insertion of one or more nucleotides, (ii) a deletion of one or more nucleotides, (iii) or both. In some cases, the stop codon can be a result of a frame shift mutation. In some cases, the stop codon may not be a result of a frame shift mutation.

In some embodiments, the stop codon can be a nonsense mutation and/or a premature stop codon. In some cases, the stop codon can be a mutation that changes a sense codon (e.g., one or more of twenty amino acids specified by the genetic code) to a stop (chain terminate) codon. In some cases, the premature stop codon can result in a truncated, incomplete, and/or nonfunctional polypeptide (e.g., a protein). In some cases, the stop codon can be in a coding region (e.g., exon) of the nucleic acid (e.g., gene). In some cases, the stop codon can be in a noncoding region (e.g., intron, promotor, etc.) of the nucleic acid. In some cases, a DNA sequence of the stop codon can be selected from the group consisting of: TAG, TAA, and TGA. In some cases, a RNA sequence encoded by a DNA comprising the stop codon is selected from the group consisting of: UAG, UAA, and UGA.

In some embodiments, the method can further comprise calculating a termination score of the nucleic acid editing tool. In some cases, the termination score can be a proportion of the termination trace in the subset. In some embodiments, the termination score can range between 0 to 1. In some cases, a termination score of 0 from the range between 0 to 1 can indicate that there is no trace comprising a stop codon in the subset. In some cases, a termination score of 1 from the range between 0 to 1 can indicate each trace in the subset comprises a stop codon. In some cases, the termination score can be at least about 0.01, 0.05, 0.1, 0.2, 0.3, 0.4, 0.5, 0.6, 0.7, 0.8, 0.9, or more. In some cases, the termination score can be at most about 0.9, 0.8, 0.7, 0.6, 0.5, 0.4, 0.3, 0.2, 0.1, 0.05, 0.01, or less. In some embodiments, the termination score can range between 0% to 100%. In some cases, a termination score of 0% from the range between 0% to 100% can indicate that there is no trace comprising a stop codon in the subset. In some cases, a termination score of 100% from the range between 0% to 100% can indicate each trace in the subset comprises a stop codon. In some cases, the termination score can be at least about 0.1%, 0.5%, 1%, 5%, 10%, 20%, 30%, 40%, 50%, 60%, 70%, 80%, 90%, or more. In some cases, the termination score can be at most about 90%, 80%, 70%, 60%, 50%, 40%, 30%, 20%, 10%, 5%, 1%, 0.5%, 0.1%, or less.

In some cases, when the first and second sequencing traces and the target sequences are provided by a user, the method can further comprise reporting to the user the termination score of the nucleic acid editing tool.

In some embodiments, the method can further comprise identifying a hidden stop trace from the subset, wherein the hidden stop trace is one of the plurality of predicted mutated traces, and wherein the indel of the termination trace yields a hidden stop codon. In some cases, the hidden stop codon can be a codon that would be read as a stop codon subsequent to a frame shift of +1 or −1.

In some cases, the method can further comprise calculating a hidden stop score of the nucleic acid editing tool. In some cases, the hidden stop score can be a proportion of the hidden stop trace in the subset. In some embodiments, the hidden stop score can range between 0 to 1. In some cases, a hidden stop score of 0 from the range between 0 to 1 can indicate that there is no trace comprising a hidden stop codon in the subset. In some cases, a hidden stop score of 1 from the range between 0 to 1 can indicate that each trace in the subset comprises a hidden stop codon. In some cases, the hidden stop score can be at least about 0.01, 0.05, 0.1, 0.2, 0.3, 0.4, 0.5, 0.6, 0.7, 0.8, 0.9, or more. In some cases, the hidden stop score can be at most about 0.9, 0.8, 0.7, 0.6, 0.5, 0.4, 0.3, 0.2, 0.1, 0.05, 0.01, or less. In some embodiments, the hidden stop score can range between 0% to 100%. In some cases, a hidden stop score of 0% from the range between 0% to 100% can indicate that there is no trace comprising a hidden stop codon in the subset. In some cases, a termination score of 100% from the range between 0% to 100% can indicate that each trace in the subset comprises a hidden stop codon. In some cases, the hidden stop score can be at least about 0.1%, 0.5%, 1%, 5%, 10%, 20%, 30%, 40%, 50%, 60%, 70%, 80%, 90%, or more. In some cases, the hidden stop score can be at most about 90%, 80%, 70%, 60%, 50%, 40%, 30%, 20%, 10%, 5%, 1%, 0.5%, 0.1%, or less.

In some cases, when the first and second sequencing traces and the target sequences are provided by the user, the method can further comprise reporting to the user the hidden stop score of the nucleic acid editing tool.

In some embodiments, the method can be implemented for identifying a stop codon. Such a method for determining the stop codon can implement one or more methods provided herein, such as, for example, the method for determining an indel frequency, the method for analyzing multiplex editing, and/or the method for determining a knockout score.

Computer System for Identifying a Stop Codon

Another aspect of the present disclosure provides a different computer system for deducing a change (e.g., edit, mutation) in a nucleic acid (e.g., gene). The computer system can include a computer program product comprising a non-transitory computer-readable medium having computer-executable code encoded therein, the computer-executable code adapted to be executed to implement a method for deducing the change in a nucleic acid. The computer-executable code can be adapted to be executed to implement the methods provided herein, such as, for example, the method for identifying a stop codon. Additionally, the computer-executable code can be adapted to be executed to implement the methods provided herein, such as, for example, the method for determining an indel frequency, the method for analyzing multiplex editing, and/or the method for determining a knockout score.

Methods for a Batch Analysis

In an aspect, the present disclosure provides a method for determining (e.g., deducing) a change (e.g., edit, mutation) in a nucleic acid (e.g., gene), comprising providing a plurality of nucleic acid sequencing data sets at once. Each data set can comprise (i) a first sequencing trace of the nucleic acid without an exposure to a nucleic acid editing tool; (ii) a second sequencing trace of the nucleic acid with an exposure to the nucleic acid editing tool; and (iii) a target sequence of the nucleic acid (e.g., a target sequence of the nucleic acid editing tool). The first and second sequencing traces can each comprise a Sanger sequencing trace. The method can further comprise, for each nucleic acid sequencing data set, performing the steps comprising generating an initial set comprising (A) the first sequencing trace and (B) a plurality of predicted traces (e.g., a plurality of predicted mutated traces) of the first sequencing trace that each comprises a change (e.g., an indel) at a cut site of the target sequence. The performing the steps can further comprise identifying a subset of the initial set by using a regression analysis. A linear combination of each trace of the subset substantially can resemble the second sequencing trace. The performing the steps can further comprise quantifying a frequency of each trace in the subset.

In some embodiments, (i) a first gene of a first data set of the plurality of gene sequencing data sets and (ii) a second gene of a second data set of the plurality of gene sequencing data sets can be different. In some embodiments, all nucleic acids of the plurality of nucleic acid sequencing data sets can be the same.

In some embodiments, the plurality of nucleic acid sequencing data sets can be provided at once prior to the performing the step (b). In some embodiments, the plurality of nucleic acid sequencing data sets can be provided one nucleic acid sequencing data set at a time. In an example, once a first nucleic acid sequencing data set is provided, a second nucleic acid sequencing data set can be subsequently provided. In any case, analysis of any one of the plurality of nucleic acid sequencing data sets (e.g., an analysis for deducing a mutation in a gene) may not begin until the plurality of nucleic acid sequencing data sets have been provided.

In some cases, the plurality of nucleic acid sequencing data sets can comprise at least 2, 3, 4, 5, 6, 7, 8, 9, 10, 15, 20, 25, 30, or more nucleic acid sequencing data sets. In some cases, the plurality of nucleic acid sequencing data sets can comprise at most 30, 25, 20, 15, 10, 9, 8, 7, 6, 5, 4, 3, or less nucleic acid sequencing data sets.

In some embodiments, the plurality of nucleic acid sequencing data sets can be received from a user (provided by the user), and the method can further comprise reporting to the user the sequence and the frequency of each trace in the subset.

In some embodiments, at least one data set of the plurality of nucleic acid sequencing data sets can further comprise a second target sequence of the nucleic acid that is different from the target sequence. In some embodiments, for each data set comprising the second target sequence of the nucleic acid, the method can further comprise generating a base trace by subtracting the sequencing trace between the cut site of the target sequence and a second cut site of the second target sequence from the first sequencing trace, wherein the cut site is upstream of the second cut site. In some embodiments, each of the plurality of predicted traces (e.g., predicted mutated traces) of the first sequencing trace can comprise a change (e.g., indel) at the cut site or the second cut site. In some embodiments, the initial set can further comprise an additional plurality of predicted traces of the base trace that each comprises a change (e.g., indel) at the cut site or the second cut site.

In some embodiments, the method can be implemented for performing a batch analysis. Such a method for performing a batch analysis can implement one or more methods provided herein, such as, for example, the method for determining an indel frequency, the method for analyzing multiplex editing, the method for determining a knockout score, and/or the method for identifying a stop codon.

Computer System for a Batch Analysis

Another aspect of the present disclosure provides a different computer system for deducing a change (e.g., edit, mutation) in a nucleic acid (e.g., gene). The computer system can include a computer program product comprising a non-transitory computer-readable medium having computer-executable code encoded therein, the computer-executable code adapted to be executed to implement a method for deducing the change in a nucleic acid. The computer-executable code can be adapted to be executed to implement the methods provided herein, such as, for example, the method for a batch analysis. Additionally, the computer-executable code can be adapted to be executed to implement the methods provided herein, such as, for example, the method for determining an indel frequency, the method for analyzing multiplex editing, the method for determining a knockout score, and/or the method for identifying a stop codon.

Computer Systems

Figure 14:
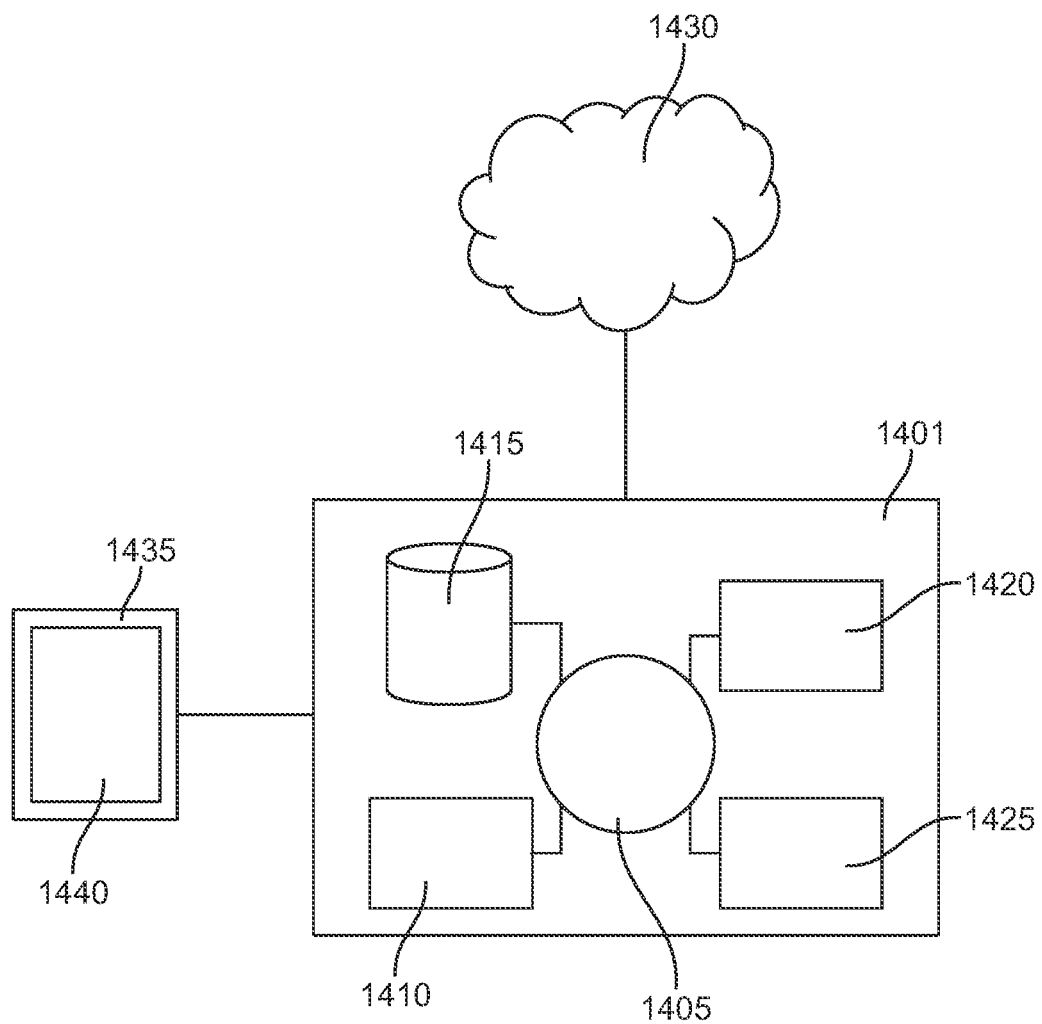
FIG. 14 shows a computer system that is programmed or otherwise configured to implement methods provided herein.

The present disclosure provides computer systems that are programmed to implement methods of the disclosure. FIG. 14 shows a computer system 1401 that is programmed or otherwise configured to deduce a mutation in a gene. The computer system 1401 can regulate various aspects of algorithms for characterizing genome edit of the present disclosure, such as, for example, an algorithm for determining an indel frequency, an algorithm for analyzing multiple editing, an algorithm for determining a knockout score, an algorithm for identifying a stop codon, and an algorithm for a batch analysis. The computer system 1401 can be an electronic device or a computer system that is remotely located with respect to the user that is providing sequencing data necessary for characterizing genome edit.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which can enable devices coupled to the computer system 1401 to behave as a client or a server.

The CPU 1405 can execute a sequence of machine-readable instructions, which can be embodied in a program or software. The instructions can be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user (e.g., a personal computer or Sanger sequencing instrument/analyzer). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, can take many forms, including but not limited to, a tangible storage medium, a carrier wave medium or physical transmission medium. Non-volatile storage media include, for example, optical or magnetic disks, such as any of the storage devices in any computer(s) or the like, such as can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 1401 can include or be in communication with an electronic display 1435 that comprises a user interface (UI) 1440 for providing, for example, a UI to upload one or more files (e.g., Sanger sequencing files, target sequences, donor templates, etc.) and a different UI to view results of the analysis of a single guide editing, a multiplex editing, a HDR analysis, or a batch analysis. Examples of UF s include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, generate an initial set of traces comprising a plurality of predicted mutated traces and identify a subset of the initial set, wherein a linear combination of each trace of the subset can yield the user's experimental outcome of gene editing.

EXAMPLES

Example 1

Algorithm(s) for Characterizing Genome Edit

FIG. 1A shows an example of a flowchart 100 of a method of deducing a mutation in a gene. The first step 110 of the method can comprise providing (i) a first sequencing trace of the gene without an exposure to a gene editing tool (i.e., a control AB1 file 111 comprising the first sequencing trace), (ii) a second sequencing trace of the gene with an exposure to the gene editing tool (i.e., a sample AB1 file 112 comprising the second sequencing trace), and (iii) at least one target sequence 113 of the gene (i.e., guide sequence(s)). In some cases, the method can further comprise providing a HDR template sequence 119. The first and second sequencing traces can be a Sanger sequencing trace. In some cases, two or more guide sequence(s) 113 can be provided to analyze multiplex editing. The guide sequence(s) 113 can be provided as nucleotide sequences (DNA or RNA) that correspond to the amino acid sequence. At least a portion of the sequencing trace in each of the control AB1 file 111 and the sample AB1 file 112 can be checked for quality control (QC) 114. In some cases, an average Phred quality score of at least a portion of the first sequencing trace in the control AB1 file 111 and/or at least a portion of the second sequencing trace in the sample AB1 file 112 can be assessed. In an example, such an assessment can identify one or more regions in each of the first and/or second sequencing trace that has an average Phred quality score of at least about 15, 20, 25, or 30. Additionally, the guide sequence(s) 113 can be used to identify at least one cut site 115 in the first sequencing trace of the control AB1 file 111. The cut site 115 can be a cut site of the gene editing tool.

Referring to FIG. 1A, the method can further comprise identifying an alignment window 116 in the first sequencing trace in the control AB1 file 111. Identifying the alignment window 116 can include trimming an end portion of the first sequencing trace of the control AB1 file 111 to terminate at 15 nucleotides upstream of the cut site. The alignment window 116 can have an average Phred quality score of at least about 15, 20, 25, or 30, according to the QC check 114. The alignment window 116 can be trimmed (shortened) such that the average Phred quality score is at least about 15, 20, 25, or 30. The alignment window 116 can be upstream of the cut site 115. The second sequencing trace of the sample AB1 file 112 can be aligned 117, 118 to the alignment window 116 of the first sequencing trace of the control AB1 file 111. Ignoring poor quality nucleotides that can be found at a beginning of a sequencing trace can improve reliability of the alignment method. Once the alignment window 116 is determined, the first sequencing trace in the control AB1 file 111 and the second sequencing trace of the sample AB1 file 112 can be aligned by the alignment window. These two globally aligned sequences can be used for generating visualizations and performing interference and/or prediction calculations.

Referring to FIG. 1A, the method can further comprise identifying an inference window 120. The inference window 120 can be a portion of the first sequencing trace. The inference window 120 can be a portion of the second sequencing trace. The inference window can be a segment of the first and/or second sequencing trace to be used to deduce one or more indels by the gene editing tool. In an example, the inference window 120 can start 25 nucleotides upstream of the cut site 115 and extend up to 100 nucleotides downstream of the cut site 115. Additionally, a quality check of the inference window 120 can be checked for QC. In some cases, the inference window 120 can have an average Phred quality score of at least about 15, 20, 25, or 30, according to the QC check.

Referring to FIG. 1A, the method can further comprise generating an initial set 130 comprising (i) the first sequencing trace of the control AB1 file 111 and (ii) a plurality of predicted mutated traces of the first sequencing trace of the control AB1 file 111 that each comprises an indel at the cut site 115 of the target sequence 113. In some cases, the initial set 130 can further comprise a sequencing trace that uses a portion of the HDR template sequence 119 as an indel. In some cases, the initial set 130 can be referred to as one or more edit proposals. The method can further comprise 140 comparing one or more traces of the initial set 130 and the second sequencing trace of the sample AB1 file 112 at the inference window 120 to predict a subset 150 comprising one or more gene editing outcomes of the gene editing tool in the second sequencing trace of the sample AB1 file 112. In some cases, a regression analysis (e.g., the NNLS regression analysis) 145 can be performed to compare the trace(s) of the initial set 130 and the second sequencing trace of the sample AB1 file 112 at the inference window 120. The regression analysis 145 can identify the subset 150 of the initial set, wherein a linear combination of each trace of the subset 150 can substantially resemble the second sequencing trace of the sample AB1 file 112 at the inference window 120.

Referring to FIG. 1A, the method can further comprise assessing a discordance signal. The discordance signal can show a level of disagreement between the non-edited, first sequencing trace of the control AB1 file 111 and the edited, second sequencing trace of the sample AB1 file 112. In some cases, the discordance signal can show, base-by-base, an amount of signal that disagrees with a reference sequence derived from the non-edited, first sequencing trace. In some cases, the discordance signal can be a measure of a presence of multiple (e.g., 2, 3, or 4), overlapping peaks at a nucleobase. In some cases, a large and/or unexpected genomic edit may not be a part of the plurality of predicted mutated traces of the non-edited, first sequencing trace. In some cases, the discordance signal can range between 0 and 1, indicating a range between a low discordance to a high discordance. In an example, a reference polynucleotide sequence can be determined from the non-edited, first sequencing trace. The first and second sequencing traces can be compared against the reference polynucleotide sequence, base-by-base, in order to detect the amount of signal from each nucleobase of the first and second sequencing traces that disagrees with the control polynucleotide sequence. In some cases, the method can further comprise determining an average discordance signal between the control polynucleotide sequence and the edited, second sequencing trace within the inference window 120. In some cases, the discordance signal and/or the average discordance signal can be reported to the user.

Referring to FIG. 1A, the method can further comprise calculating a frequency of a plurality of indel sizes (e.g., −5, −4, −3, −2, −1, 0, +1, +2, +3, +4, +5 indels) of the subset 150 of the initial set 130. In some cases, the method can further comprise generating a distribution of the plurality of indel sizes (e.g., a plot) of the subset 150. In some cases, the plot can be a bar graph. In some cases, the method can further comprise quantifying a frequency of each trace of each indel size of the plurality of indel sizes of the subset 150. In some cases, different traces comprising a same indel size can be grouped into one overall indel size. In some cases, different traces comprising a same indel size can be separated into different groups.

Figure 1B:
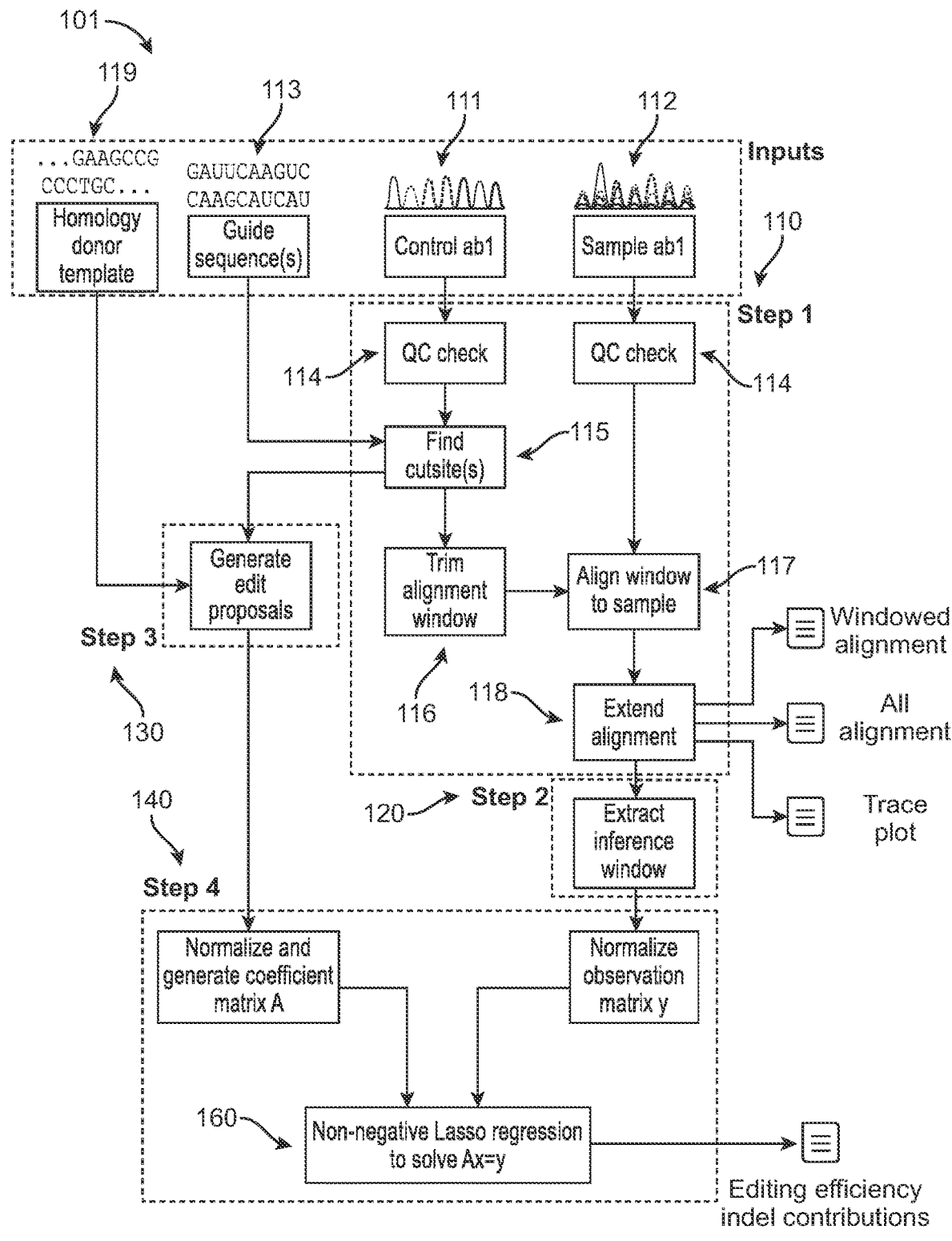

FIG. 1B shows another example of a flowchart 101 of a method of deducing a mutation in a gene. The method of the flowchart 101 of FIG. 1B can utilize one or more processes or tools as provided in the method of the flowchart 100 of FIG. 1A. Referring to FIG. 1B, the method can comprise generating an initial set 130 (i.e., one or more edit proposals) comprising (i) the first sequencing trace of the control AB1 file 111, (ii) a plurality of predicted mutated traces of the first sequencing trace of the control AB1 file 111 that each comprises an indel at the cut site 115 of the target sequence 113, and optionally (iii) a sequencing trace that uses a portion of the HDR template sequence 119 as an indel. The method can comprise comparing one or more traces of the initial set 130 and the second sequencing trace of the sample AB1 file 112 at the inference window 120 to predict a subset 150 comprising one or more gene editing outcomes of the gene editing tool in the second sequencing trace of the sample AB1 file 112. In some cases, a RLS analysis (e.g., the Lasso regression or non-negative Lasso regression, as used interchangeably herein) 160 can be performed to compare the trace(s) of the initial set 130 and the second sequencing trace of the sample AB1 file 112 at the inference window 120. The non-negative Lasso regression analysis 160 can identify the subset 150 of the initial set, wherein a linear combination of each trace of the subset 150 can substantially resemble the second sequencing trace of the sample AB1 file 112 at the inference window 120. When using Sanger sequencing data, the RLS analysis can better mitigate to the noise in sequencing data than the NNLS regression analysis.

Example 2

Cell Culture and Processing

Genome editing (i.e., gene editing) can be performed with any of the nucleases described herein as a gene editing tool. In some cases, the gene editing tool can be a CRISPR system comprising Cas-like nucleases and sgRNAs. Gene editing can be performed on a variety of cell lines. The sgRNAs can be synthesized with or without modifications. The sgRNAs can be complexed with Cas-like proteins (e.g., Cas9) at a molar ratio of sgRNA:Cas9 (e.g., 9:1) to form ribonucleoproteins (RNPs). The resulting RNPs can be transfected into a respective cell line using a transfection agent (e.g., Nucleofector from Lonza). Transfected cells can be recovered in a medium (e.g., a normal growth medium), plated into a plate (e.g., a 96-well tissue culture plate), and incubated in humidified 37° C./5% $CO_2$. After a time (e.g., 48 hours), the cells can be lysed and genomic DNA can be extracted from the cells using a DNA extraction agent (e.g., QuickExtract™ DNA Extraction Solution from, Lucigen) to each well of the plate.

Knock-in editing can be performed in HEK293 cells using modified sgRNAs (e.g., from Synthego) and single-stranded DNA (ssDNA) donor templates (e.g., from Eurofins Genomics). The ssDNA templates can be designed to knock in sequences of varying length (e.g., +0 single nucleotide polymorphism (SNP), +14 SNP, or +36 bp SNP) with symmetric homology arms (e.g., symmetric 40 bp homology arms). The components can be introduced at a ratio of 9:1:3 (sgRNA:Cas9:ssDNA).

A plurality of genes (e.g., 32 genes) can be targeted for gene editing. In some cases, an individual gene of the plurality of genes can be targeted with multiple sgRNAs (e.g., three sgRNAs) that are specifically designed to produce one or more large deletions. For the individual gene, the sgRNAs can be transfected individually or in combination, for a plurality of samples (e.g., 128 samples). In some cases, three to four replicate edits can be performed and Sanger-sequenced, while one replicate can be amplified for NGS of amplicons (e.g., Amp-Seq). Results from analyses of the multiple replicates of Sanger sequencing can be averaged to compare with the Amp-Seq results.

To perform Sanger sequencing, polymerase chain reaction (PCR) primers can be designed to amplify a segment (e.g., a 500-800 nucleobase segment) containing a cut site of the gene editing tool. PCR can be performed on lysed genomic samples using a polymerase (e.g., Taq polymerase). Following, Sanger sequencing of the PCR products can be performed with one of the two primers used for amplification. Sanger sequencing can be performed on a cell (or a population of cells) with or without an exposure to the gene editing tool.

For HDR transfections, primers can be designed such that the same cut can be used for both Sanger sequencing and Amp-Seq. The resulting amplicons can be 300-500 bq with the cut site 100 bp from the forward primer.

The Amp-Seq technique can be used as an example of the NGS technique. To perform Amp-Seq, a segment (e.g., a 200-300 nucleobase segment) containing the cut site of the gene editing tool can be amplified from each lysed genomic sample. Resulting amplicons can be purified, then quantified (e.g., by a Nanodrop instrument). Following, amplicons can be sequenced via Amp-Seq. A summarization analysis can be performed (e.g., by using the Massachusetts General Hospital (MGH)-NGS data pipeline) to obtain sequences and their abundances in the sequenced samples.

Example 3

Predicting Genome Edit

FIG. 2 shows example plots provided by the method for deducing a mutation in a gene by a gene editing tool. In an example, the gene can be the human gene GRK5. FIG. 2A shows a portion of a first sequencing trace 201 without an exposure to the gene editing tool (e.g., from the control AB1 file 111) and a portion of a second sequencing trace 202 with an exposure to the gene editing tool (e.g., from the sample AB1 file 112). A first trace segment 201a (e.g., nucleotides 199 to 264) from the first sequencing trace 201 and a second trace segment 202a (e.g., nucleotides 201 to 266) from the second sequencing trace 202 can be shown. The first trace segment 201a and the second trace segment 202a can be aligned to an alignment window. The first trace segment 201a and the second trace segment 202a can span a position of a cut site 203 of the gene editing tool with respect to the first trace segment 241. A position and length of the guide sequence (or target sequence) of the gene editing tool with respect to the first trace segment 201a can be indicated by a line 204. FIG. 2B shows a discordance plot 210 displaying, base-by-base, an amount of signal from the sequencing traces that disagrees with a reference sequence derived from the non-edited, first sequencing trace. A discordance trace 201b can show, base-by-base, the amount of signal from the first sequencing trace that disagrees with the reference sequence. A discordance trace 202b can show, base-by-base, the amount of signal from the second sequencing trace 202 that disagrees with the reference sequence. The discordance plot can show the position of the cut site 203. The discordance plot can show the position and length of the alignment window 205. The discordance plot can indicate the position of the inference window 204. In some cases, due to the exposure to the gene editing tool, the discordance trace 202b can exhibit a higher discordance than the discordance trace 201b in one or more nucleobases downstream of the cut site 203 or in the inference window 204. FIG. 2C shows a distribution plot 220 displaying a frequency (e.g., a percentage) of each indel size in the subset 150 of the initial set 130. Each indel size can comprise one or more traces with different indel sequences. In some cases, the plot can include a frequency of a trace of the subset 150 that does not have an indel. In addition, the plot can show an edit efficiency 221 (e.g., from a scale 0 to 1) that indicates a portion of traces in the subset 150 that have an indel. In addition, the plot can show an R-squared value 222 of the regression analysis (e.g., the NNLS regression analysis or the Lasso regression analysis) used to identify the subset 150 from the initial set 130. In this example, an indel limit can be set at −30 and +14 for a single DNA break.

Example 4

Comparison of Predicting Genome Edit and Sequencing Genome Edit

FIG. 3 shows example plots 310, 320, 330, and 340 that compare outcomes of two methods of deducing one or more mutations of a gene subsequent to an exposure to a gene editing tool (e.g., a CRISPR/Cas complex). The two methods can include (i) the method(s) provided herein (e.g., as described in FIGS. 1A-1B) that uses a Sanger sequencing trace, and (ii) a NGS method (e.g., Amp-Seq) that does not use any Sanger sequencing trace. Each of the example plots 310, 320, 330, and 340 can comprise a first distribution plot of indels that are predicted by the method(s) provided herein (e.g., similar to the distribution plot 220 shown in FIG. 2C). The first distribution plot can be labeled "P" (e.g., 310-P). Additionally, each of the example plots 310, 320, 330, 340, 342, and 344 can comprise a second distribution plot of indels that are sequenced (i.e., measured) and analyzed by the NGS method. The second distribution ploy can be labeled "S" (e.g., 310-S). The first and second distribution plots of indels can show a size of each of the indels (e.g., a size of an insertion as a positive integer and a size of a deletion as a negative integer) and its respective frequency. The first and second distribution plots can be shown side-by-side for comparison. Referring to FIG. 3A, a plot 310 compares predicting genome edit and sequencing genome edit of the Protein Kinase AMP-Activated Non-Catalytic Subunit Gamma 1 (PRKAG1) gene. A plot 320 compares predicting genome edit and sequencing genome edit of the Receptor-Like Tyrosine Kinase (RYK) gene. Referring to FIG. 3B, a plot 330 compares predicting genome edit and sequencing genome edit of the Calcium/Calmodulin Dependent Protein Kinase I (CAMK1) gene. Referring to A plot 340 compares predicting genome edit and sequencing genome edit of the Serine/Threonine Kinase 4 (STK4) gene. Referring to FIG. 3C, a plot 342 compares predicting genome edit and sequencing genome edit of the mitotic checkpoint serine/threonine-protein kinase BUB1 beta (BUB1B) gene. Referring to FIG. 3D, a plot 344 compares predicting genome edit and sequencing genome edit of the Conserved Helix-Loop-Helix Ubiquitous Kinase 2 (CHUK) gene. The plots 310, 320, 330, 340, 342, and 344 can indicate a high correlation (e.g., an overall R-squared value of 0.93) between the two methods.

FIG. 3E shows an example of a predicted mutated sequence 350 of a gene (e.g., the Uridine-Cytidine Kinase 2 gene) following gene editing by a gene editing tool (e.g., the CRISPR/Cas system). The sequence 350 can be predicted by the method(s) described herein. In an example, the sequence 350 can be a sequence from the subset 150 of the initial set 130, as described in FIGS. 1A-1B. The sequence 350 can comprise a first sequence 351 (in bold) and a second sequence 352 (underlined) that are disposed adjacent to each other due to a predicted deletion 353 (e.g., a deletion of 51 nucleotides) between the first sequence 351 and the second sequence 352. In some cases, a frequency of the sequence 350 can be 51.7% in a group of predicted sequences that in combination resemble a final outcome of the gene editing by the gene editing tool. In an example, a frequency of the sequence 350 can be 51.7% in the subset 150. Additionally, FIG. 3E shows an example of a measured sequence 355 of the same gene following gene editing by the same gene editing tool. The sequence 355 can be sequenced by a NGS technique. The sequence 355 can comprise a first sequence 356 (in bold) and a second sequence 357 (underlined) that are adjacent to each other. In some cases, a frequency of the sequence 355 can be 40.5% in a group of measured sequences from a cell or a population of cells treated by the gene editing tool. The first and second sequences 351 and 352 of the predicted sequence 350 can substantially or entirely match the first and second sequences 356 and 357 of the measured sequence 355, respectively. In addition, the frequency (e.g., 51.7%) of the predicted sequence 350 can be similar to the frequency (e.g., 40.5%) of the measured sequence 355.

FIG. 3F shows another example of a predicted mutated sequence 360 of a gene (e.g., the Uridine-Cytidine Kinase 2 gene) following gene editing by the gene editing tool (e.g., the CRISPR/Cas system). The sequence 360 can be predicted by the method(s) described herein. In an example, the sequence 360 can be a sequence from the subset 150 of the initial set 130, as described in FIGS. 10A-1B. The sequence 360 can comprise a first sequence 361 (in bold) and a second sequence 362 (underlined) that are disposed adjacent to each other due to a predicted deletion 363 (e.g., a deletion of 30 nucleotides) between the first sequence 361 and the second sequence 362. In some cases, a frequency of the sequence 360 can be 9.8% in a group of predicted sequences that in combination resemble a final outcome of the gene editing by the gene editing tool. In an example, a frequency of the sequence 360 can be 9.8% in the subset 150. Additionally, FIG. 3F shows an example of a measured sequence 365 of the same gene following gene editing by the same gene editing tool. The sequence 365 can be sequenced by a NGS technique. The sequence 365 can comprise a first sequence 366 (in bold) and a second sequence 368 (underlined) that are adjacent to each other. In some cases, a frequency of the sequence 365 can be 9.99% in a group of measured sequences from a cell or a population of cells treated by the gene editing tool. The first and second sequences 361 and 362 of the predicted sequence 360 can substantially or entirely match the first and second sequences 366 and 368 of the measured sequence 365, respectively. In addition, the frequency (e.g., 9.8%) of the predicted sequence 360 can be similar to the frequency (e.g., 9.99%) of the measured sequence 365.

Figure 3A:
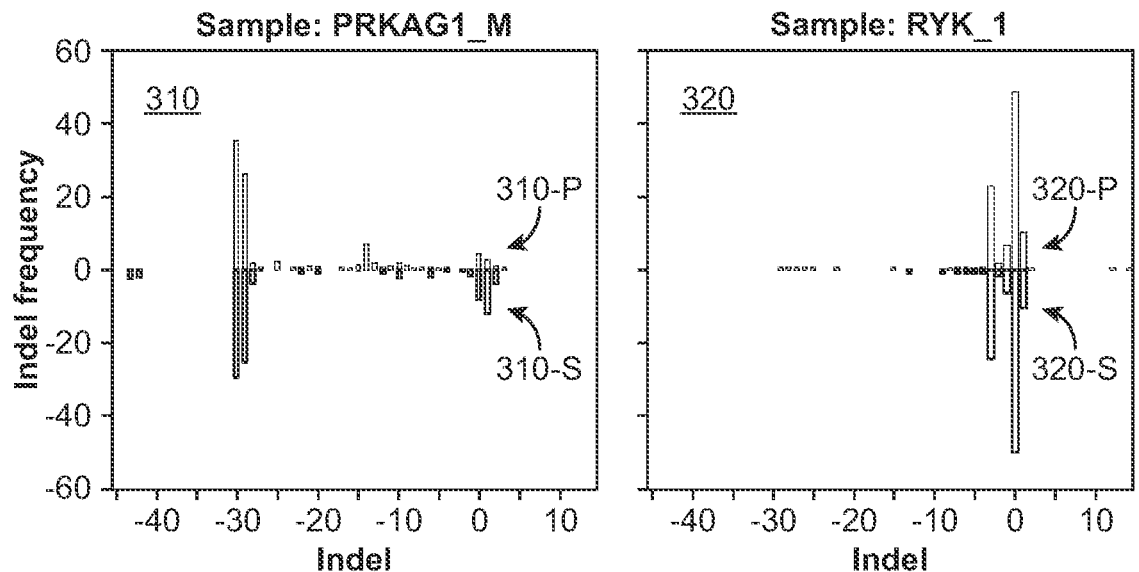
FIGS. 3A-3D show examples of plots of comparison between a prediction method and a next generation sequencing method of deducing an edit in a nucleic acid.
Figure 3B:
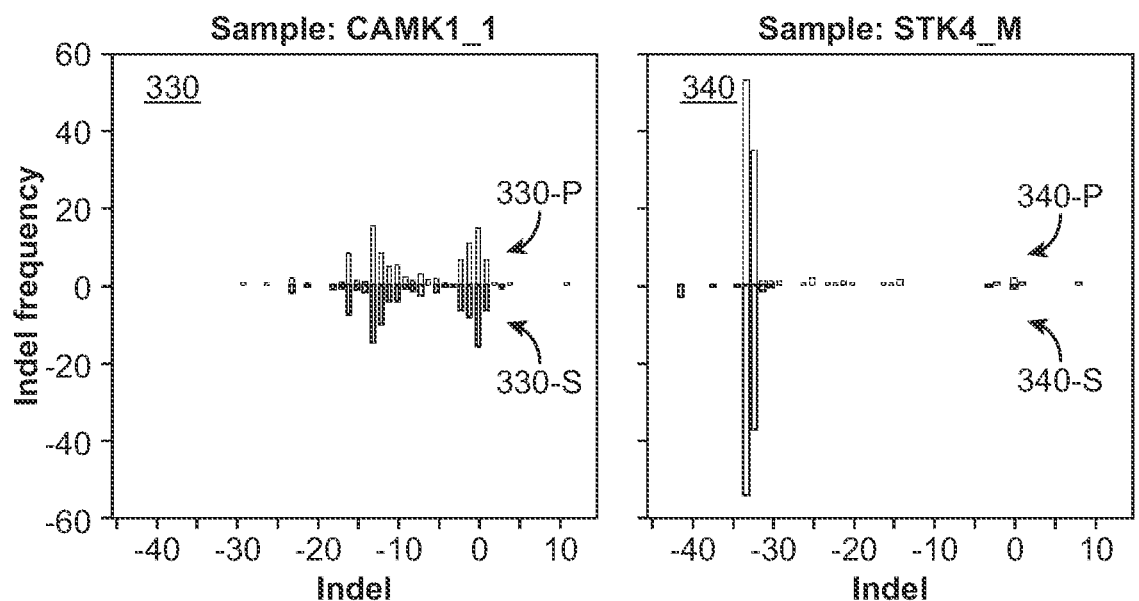
Figure 3C:
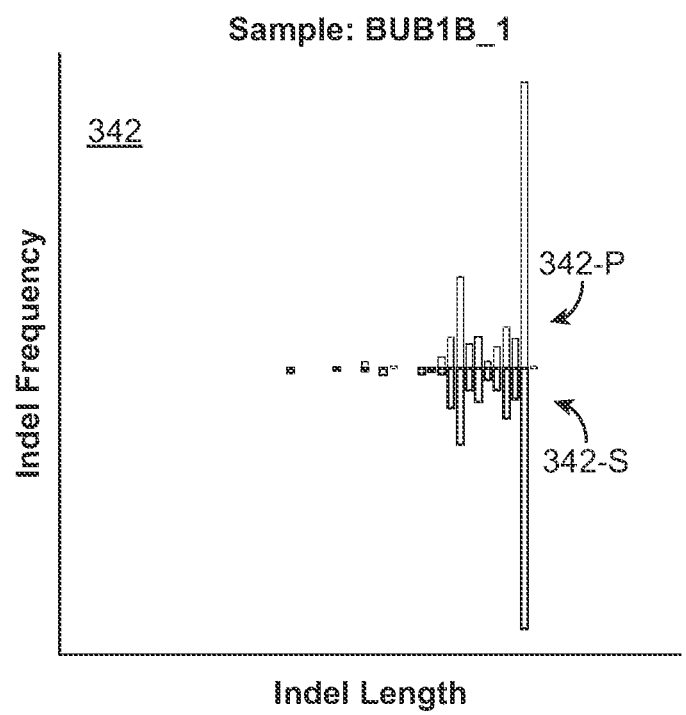
Figure 3D:
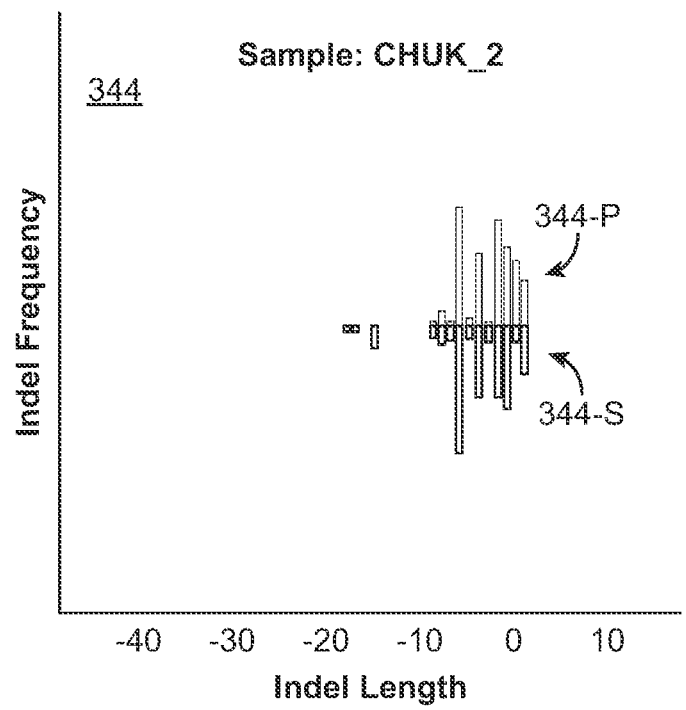
Figure 3G:
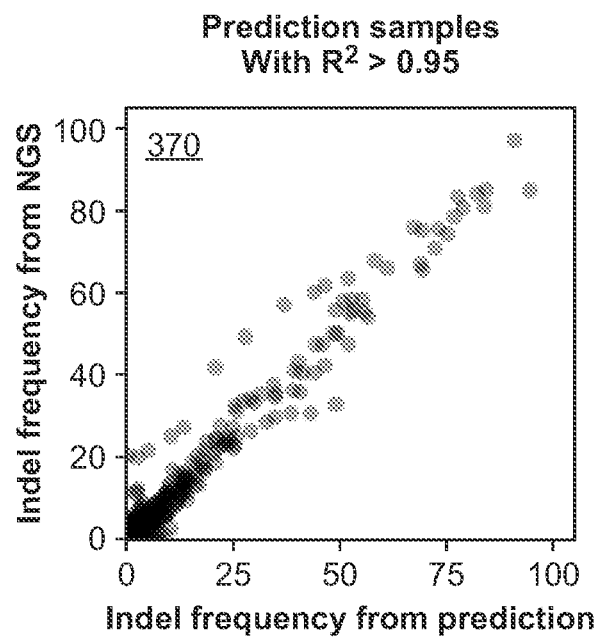
FIGS. 3G-3H show examples of a pair-wise comparison of indel frequencies obtained from a prediction method and a next generation sequencing method of an edit in a nucleic acid.
Figure 3H:
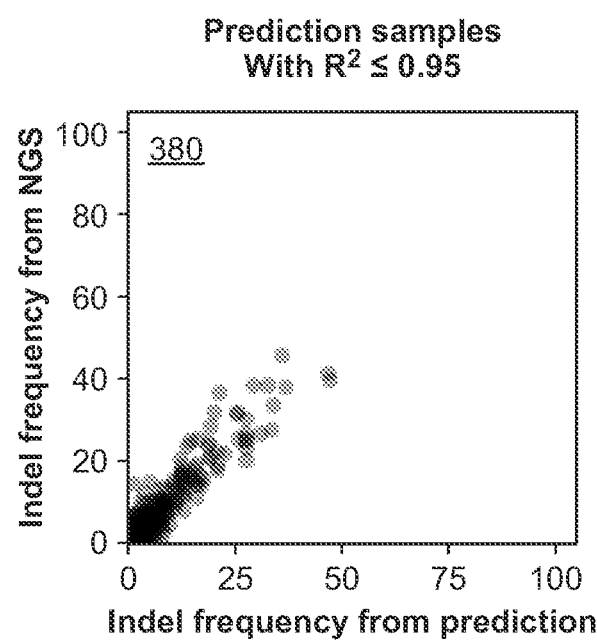

As shown in FIGS. 3G and 3H, each of the pairwise points from the indel distributions between the prediction method and the sequencing method (e.g., the indel distributions shown in FIGS. 3A-3D) can be plotted in one or more scatterplots. In some cases, for each gene, a frequency of each indel size (e.g., a deletion of 30 nucleotides) of a gene obtained from the prediction method described herein can be plotted against a respective frequency of the same indel size of the same gene obtained from the NGS technique. In some cases, a data point in the scatterplot can comprise the indel frequency from the prediction method on the X-axis and the respective indel frequency from the NGS technique on the Y-axis. Referring to FIG. 3G, a scatterplot 370 can compare all of the pairwise points from the indel distributions for high quality prediction analysis samples with an R-squared value of the regression analysis greater than 0.95 ($R^2>0.95$). In the scatterplot 370, an R-squared value of a correlation (e.g., by using a Pearson correlation method) between the two methods can be 0.96. Referring to FIG. 3H, a scatterplot 380 can compare all of the pairwise points from the indel distributions for low quality prediction analysis samples with an R-squared value of the regression analysis less than or equal to 0.95 ($R^2 \leq 0.95$). In the scatterplot 380, an R-squared value of a correlation (e.g., by using a Pearson correlation method) between the two methods can be 0.88.

Example 5

Non-Negative Least Square Regression and Lasso Regression

As abovementioned, after the edit proposal stage (e.g., generating an initial set comprising at least a plurality of predicted sequencing traces), a regression is performed to infer the frequencies of each proposal sequence. The frequencies of each proposal sequence can be used, for example, to generate a subset of the initial set that substantially resembles the experimental sequencing trace (e.g., an edited sequencing trace of an edited sample). In some cases, a RLS regression analysis (e.g., Lasso regression or Ridge regression) can be used in place of non-negative least squares regression for one or more advantages as provided in the present disclosure. For example, in Lasso regression, x is solved for in the equation $Ax=y$, where A is a matrix composed of the predicted sequencing traces (i.e., simulated traces) and y is the edited sequencing trace. Lasso regression finds a linear combination of the one or more of the simulated traces that best explains the edited sequencing trace of the edited sample. In comparison to non-negative least squares regression that can overfit to the noise in sequencing data (e.g., Sanger sequencing data), Lasso regression mitigates overfitting to the noise in Sanger sequencing data via regularization, e.g., L1 regularization. Lasso regression thus can produce more accurate results compared to alternative regression algorithms like non-negative least squares regression. In Lasso regression, the relative prevalence of each edit proposal is extracted from the vector of weights of the regression (x). Percentages of individual edits are rounded to the nearest whole percentage point to reflect the model's underlying confidence about the accuracy of contribution estimations. The correlation between the regression derived and the observed edited sequencing trace ($r^2$) measures the extent to which the edit proposals can explain the edited sequencing trace.

Figure 3I:
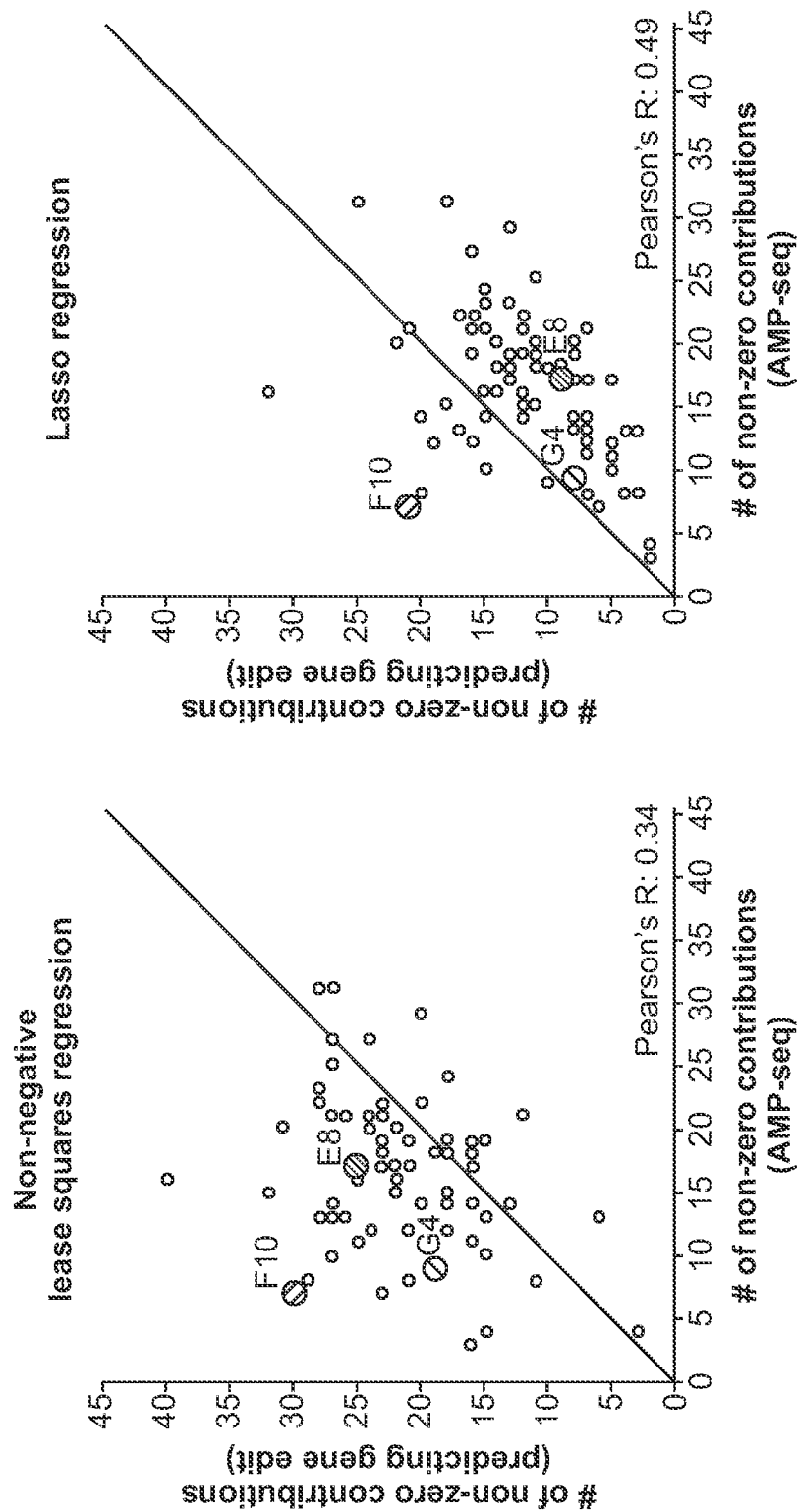
FIGS. 3I-3J show comparisons of regression analysis with and without regularization of data set when analyzing predicted gene edits.
Figure 3J:
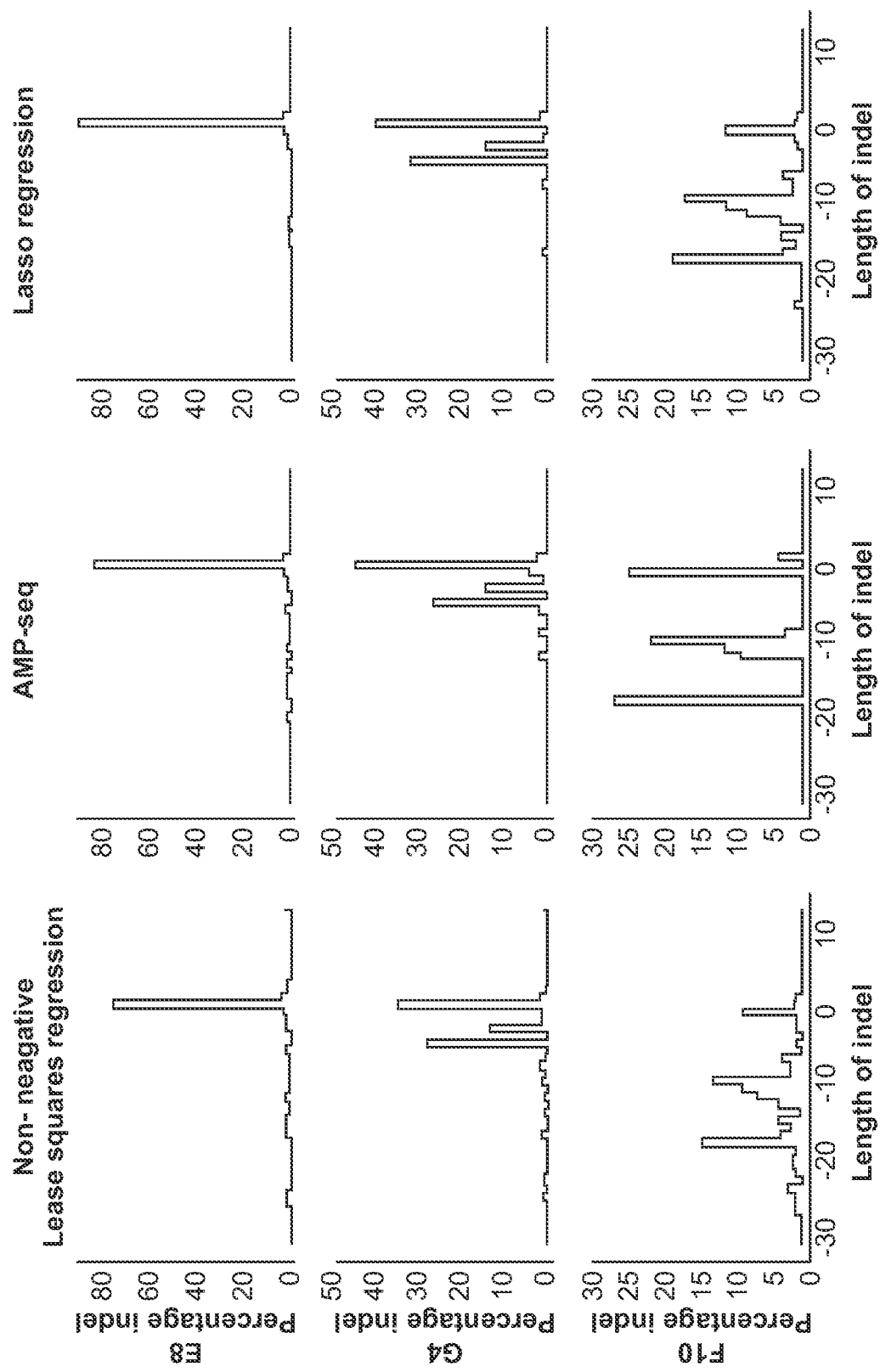

FIGS. 3I and 3J show comparisons of non-negative least squares regression and Lasso regression when applied to the method(s) provided herein (i.e., prediction of gene edit). The results are presented in comparison to Amp-Seq as a control in CRISPR genomic analysis. Amplicon sequencing on 92 samples were performed using Massachusetts General Hospital (MGH) CRISPR sequencing service. As shown in FIG. 3I (left), while some samples correlated well between Amp-Seq and the prediction of gene edit using non-negative least squares regression, there was little correlation in terms of the overall group of samples tested (as shown by Pearson's correlation coefficient of 0.34). Three representative samples (F10, G4, and F8) are shown to be scattered randomly and without any correlation to a model 1:1 correlation line. This can be due to predicting one or more indels that were not present in Amp-Seq. Alternatively, or in addition to, this can be due to overfitting a noise signal associated with Sanger sequencing and predicting false-positive edits to compensate for the background noise. One way of reducing (or removing) such false-positive edits can be to use regularization. In the instant case, Lasso regression was used instead of the non-negative least square regression to reduce the false-positive edits. As shown in FIG. 3I (right), applying the Lasso regression with an L1 parameter of 0.8 to the prediction of gene edit yielded a decreased in the number of false-positives predictions, while improving the correlation with the Amp-Seq results (as shown by Pearson's correlation coefficient of 0.49). The three representative samples (F10, G4, and F8) are shown to be uniformly scattered relative to the model 1:1 correlation line. As shown in FIG. 3J, regularization via the Lasso regression resulted in an indel profile more closely resembling that of Amp-seq across tested edits, in comparison to the non-negative least squares regression method, at least by reducing the influence of the underlying noise in Sanger sequencing data during the analysis.

Figure 3K:
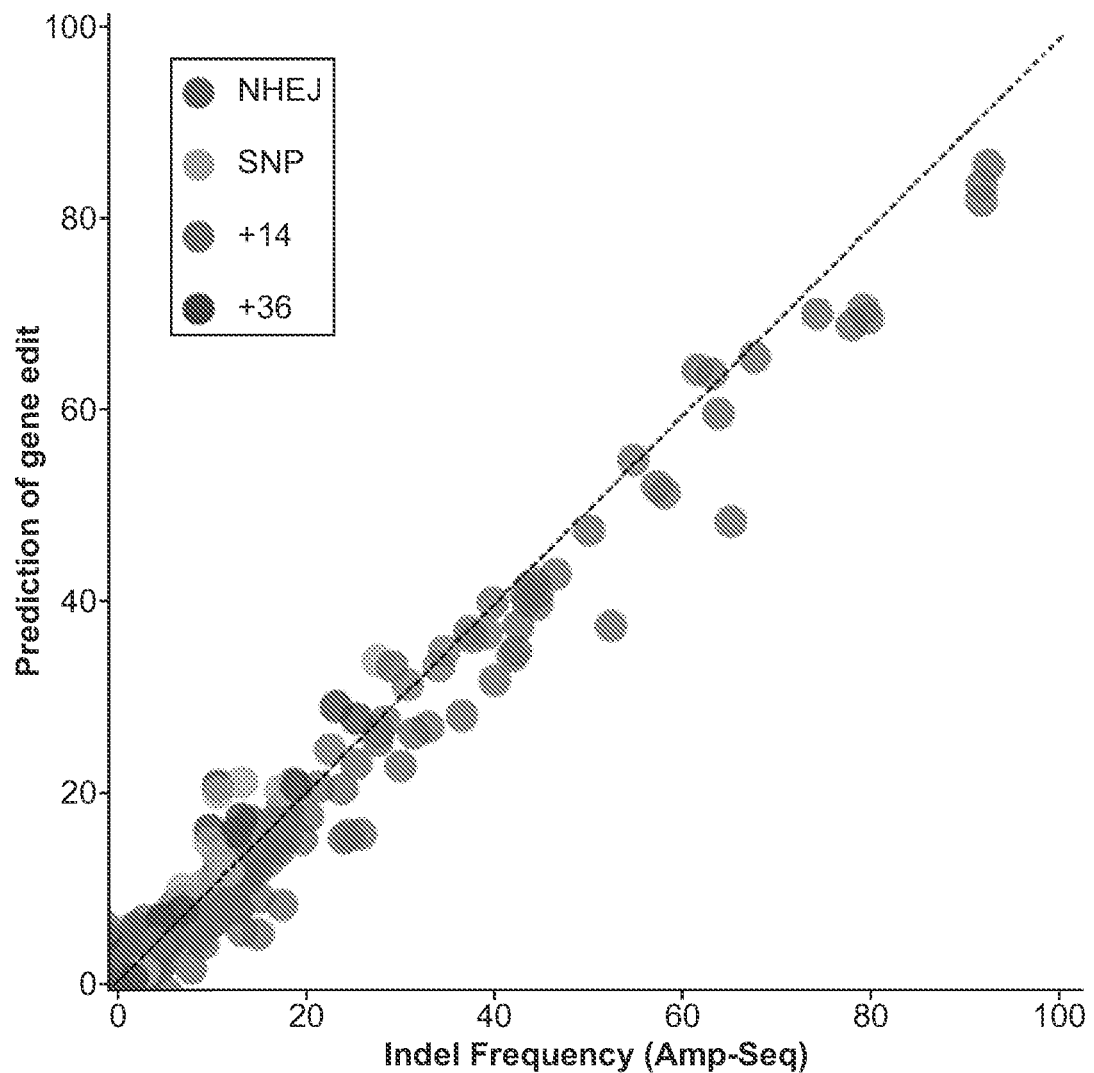
FIG. 3K shows an example comparison of next generation sequencing and the prediction method of the present disclosure in deducing a nucleic acid edit from homology directed repair editing and non-homologous end joining editing.

Furthermore, Sanger sequencing-based prediction of gene edit and Amp-Seq were performed on an additional 40 samples to test whether the prediction of gene edit can estimate rates of HDR. A single-stranded DNA donor template was provided for the additional 40 samples. The samples were designed to target 15 different cut sites and utilized donor templates with a range of insert sequence sizes, ranging from 0 to 36 bp. In an example, the insert sequence can be a single base, i.e., SNP. In another example, the insert sequence can be 14 bp long (i.e., +14). In a different example, the insert sequence can be 36 bp long (i.e., +36). As shown in FIG. 3K, a high correlation between Amp-Seq and the prediction of gene edit was observed for the HDR and NHEJ editing outcomes. An overall correlation between the Amp-Seq and the prediction of gene edit in FIG. 3K was $r^2=0.97$. In the case of prediction of HDR-based gene edit, the Sanger sequencing-based prediction can require provision of the donor template sequence. However, the Sanger sequencing-based prediction may not require provision of a Sanger sequencing trace of the donor template itself. Alternatively, the Sanger sequencing-based prediction can utilize the Sanger sequencing trace of the donor template.

In some cases, Sanger sequencing-based gene edit analysis (e.g., CRISPR analysis) can utilize one or more assumptions in predicting one or more edited outcomes. An example assumption can be that a peak signal "S" for different bases at each position is linearly proportional to the molarity of the base "m" with the relationship "S=bm." Furthermore, the coefficient "b" can be assumed to be the same for all bases. However, the peak height and phasing for a particular base in the Sanger sequencing trace is a function of the local sequence context, and thus the one or more assumptions can result in one or more sequences in which molar ratios of bases present at a given position are not reflected by the Sanger signal ratios. Because base editing and HDR can rely on the signal from single base positions, the peak height and phasing assumptions can have an adverse effect. However, the high correlation between the prediction of gene edit based on Sanger sequencing and Amp-Seq (as shown in FIG. 3K, for example) can indicate that such assumption(s) may not affect an ability of the Sanger sequencing-based prediction of gene edit to predict insertions and/or deletions. In some cases, because an indel affects the signal for all bases downstream, the effect of peak signal variance can cancel out over many bases.

Example 6

Simulation of Variant Outcomes

The performance of the method(s) of deducing a mutation in a gene as described herein (e.g., the algorithm shown in FIGS. 1A-1B) can be validated by a simulated base editing. A single nucleotide polymorphism (SNP) can be amplified from genomic lysates of two cell types (e.g., SNP rs2072579 from the induced pluripotent stem cell line PGP1 and the HEK293 cell line). The amplicons can be sequenced to verify that the first cell (e.g., PGP1) is homozygous G/G and the second cell (e.g., HEK293) is homozygous C/C. Amplicon masses can be quantified (e.g., by using a Fragment Analyzer from AATI), then mixed (e.g., by hand-pipetting) in different ratios (e.g., 5%, 10%, 20%, 40%, 60%, 80%, 90%, 95% of PGP1 amplicons in the mixture of amplicons from PGP1 and HEK293) to generate simulated gene editing outcomes with varying single base editing. Subsequently, the simulated gene editing outcomes with varying single base editing can be analyzed by Sanger sequencing and the method(s) of deducing a mutation in a gene as described herein.

Figure 4:
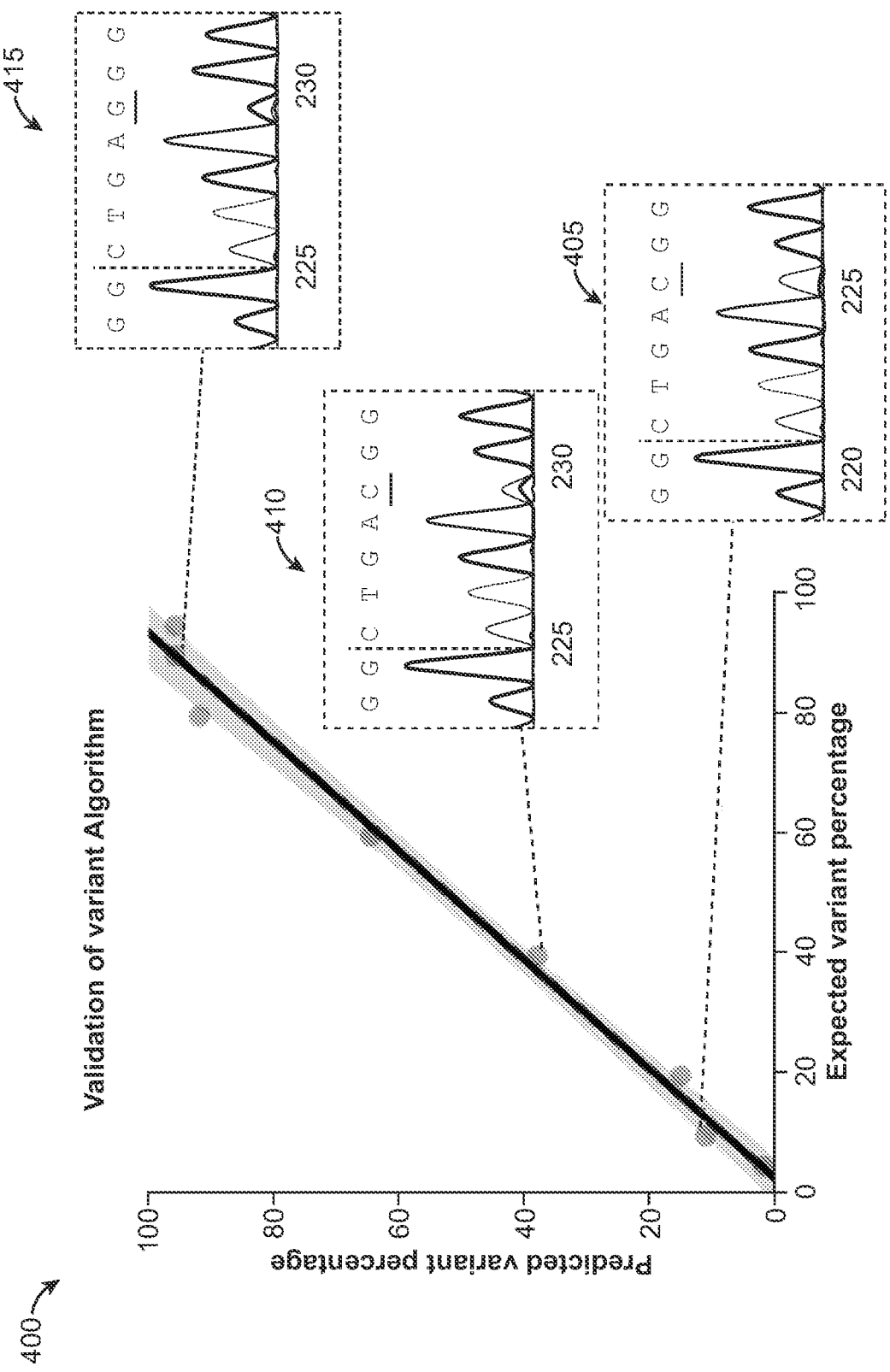
FIG. 4 shows an example plot of validating a prediction method of deducing an edit in a nucleic acid.

As shown by the correlation plot 400 in FIG. 4, the predicted variant percentage obtained by the method(s) described herein can correlate with the expected variant percentages. Examples chromatograms of the simulated gene editing outcomes are shown in the insets 405 (10% PGP1 and 90% HEK293), 410 (40% PGP1 and 60% HEK293), and 415 (90% PGP1 and 10% HEK293). In some cases, an R-squared value of a correlation (e.g., by using a Pearson correlation method) between the predicted variant percentages and the expected variant percentages can be 0.99, indicating a high correlation.

Example 7

User Interface for a Single Guide Editing

In some cases, the computer system described herein can comprise one or more user interfaces for a user to provide information and/or data needed for deducing a mutation in a gene by a gene editing tool. The gene editing tool can be a CRISPR/Cas9 system. In some cases, the user interface(s) can also display results of deducing the mutation in the gene to the user. In some cases, the user interface(s) can allow the user to download the results of deducing the mutation in the gene.

Figure 5A:
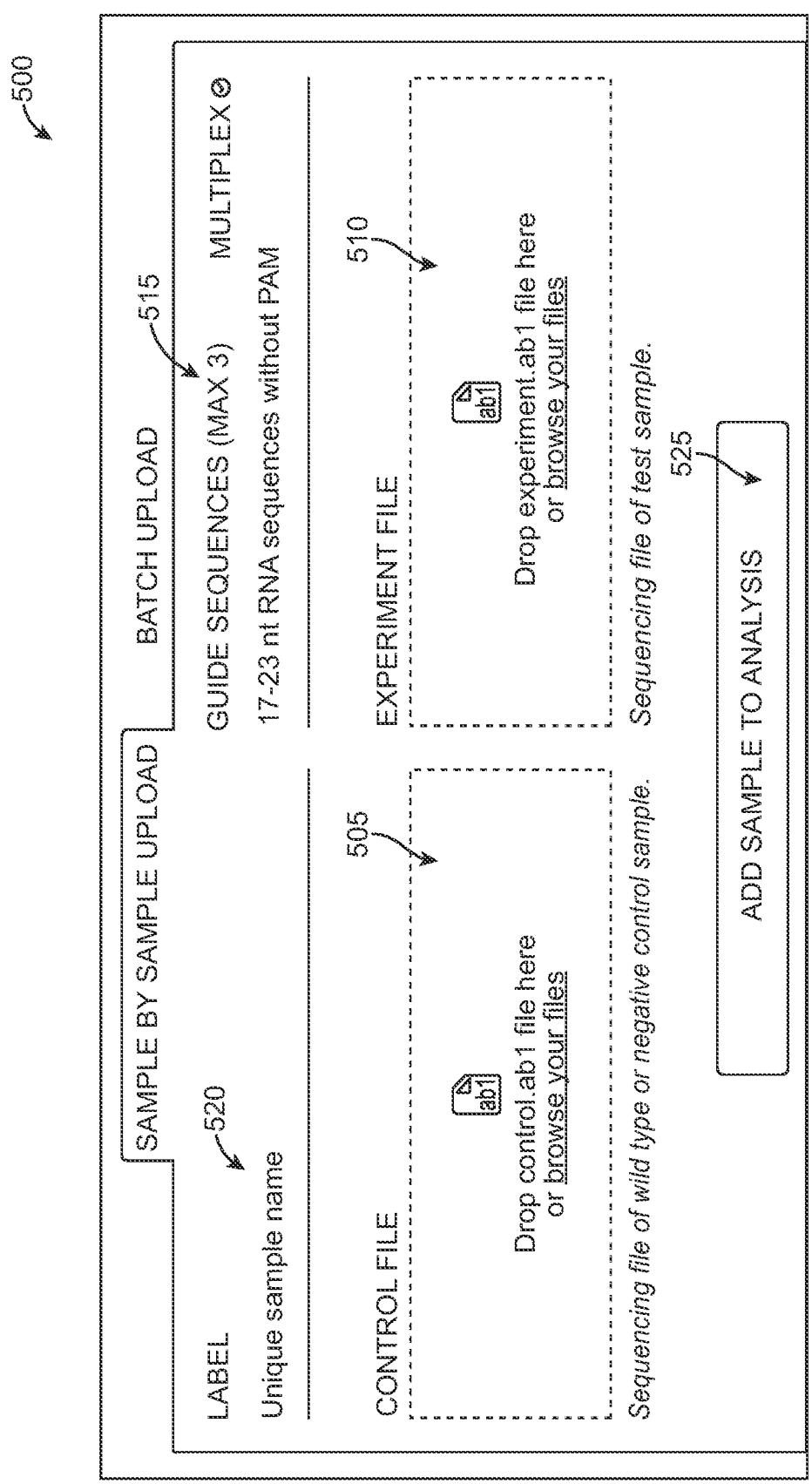
FIGS. 5A-5B illustrate examples of a window of a graphical user interface (GUI) for a user to provide sequencing files and a target sequence for deducing an edit in a nucleic acid from a single guide editing.
Figure 5B:
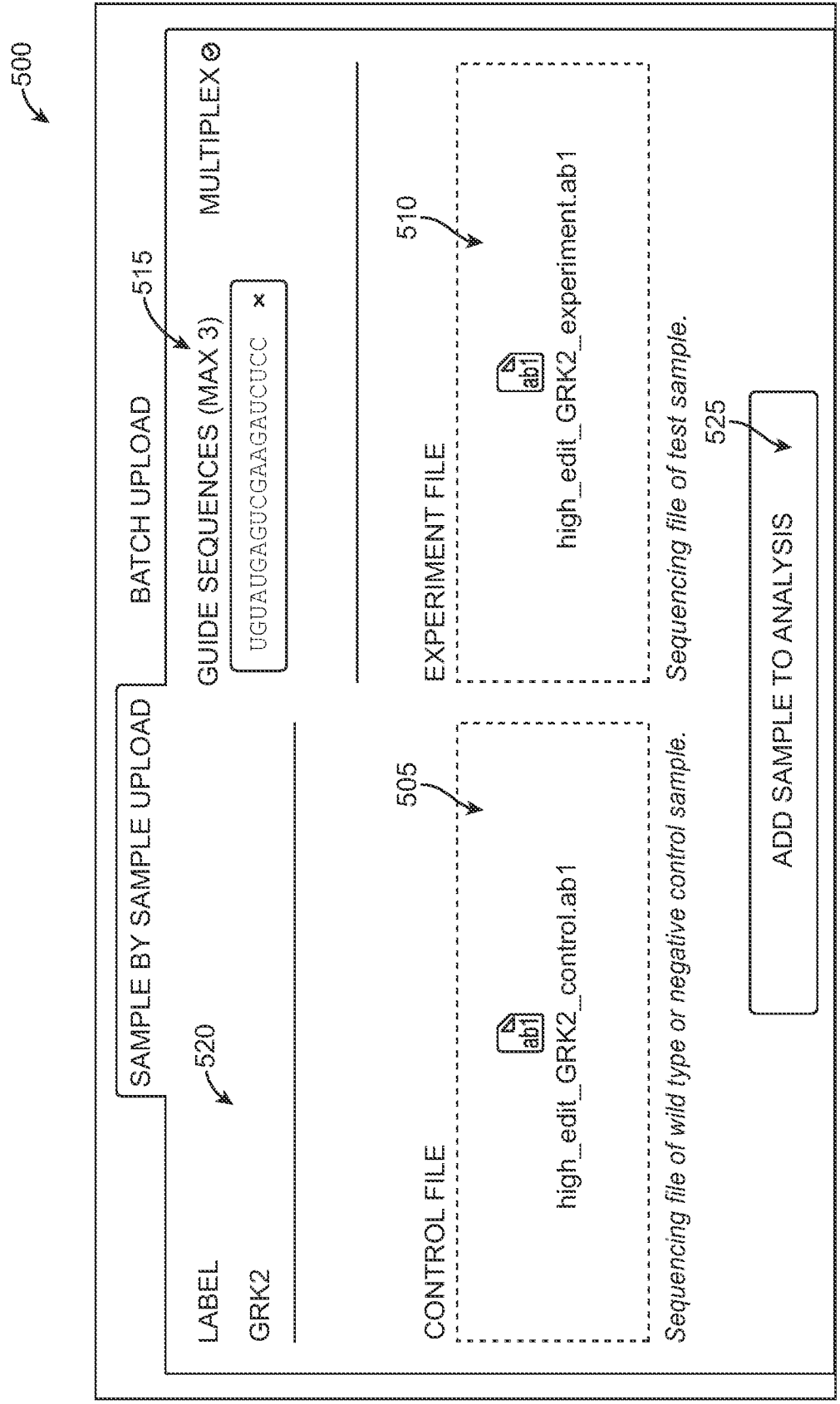

FIG. 5A illustrates an example of a window 500 of a graphical user interface (GUI) for the user to provide (i) a first AB1 file 505 comprising a first sequencing trace of the gene without an exposure to a gene editing tool (i.e., control file), (ii) a second AB1 file 510 comprising a second sequencing trace of the gene with an exposure to the gene editing tool (i.e., experiment file), and (iii) a target sequence 515 of the gene (i.e., guide sequence). In some cases, the first sequencing trace can be a sequencing trace of a wild type or control sample. In some cases, the second sequencing trace can be a sequencing trace of a test sample or an edited sample. The first and second sequencing traces of the first and second AB1 files 505 and 510, respectively, can each be a Sanger sequencing trace. In some cases, the user can designate a name 520 for the analysis of the samples provided. The window 500 of the GUI can have an option 525 for the user to initiate analysis of the samples. In some cases, such option 525 may not be available until necessary information (e.g., the files 505, 510 and the information regarding the target sequence 515 and the name 520) have been provided and uploaded to the GUI successfully. FIG. 5B illustrates another example of the window 500 of the GUI after the user has provided the files 505, 510 and the information regarding the target sequence 515 and the name 520. As shown, the option 525 for the user to initiate analysis of the samples can now be available.

The analysis can comprise generating an initial set comprising (i) the first sequencing trace and (ii) a plurality of predicted mutated traces of the first sequencing trace that each comprises an indel at a cut site of the target sequence 515. The analysis can also comprise identifying a subset of the initial set by using a regression analysis, wherein a linear combination of each trace of the subset can substantially resemble the second sequencing trace.

Figure 6A:
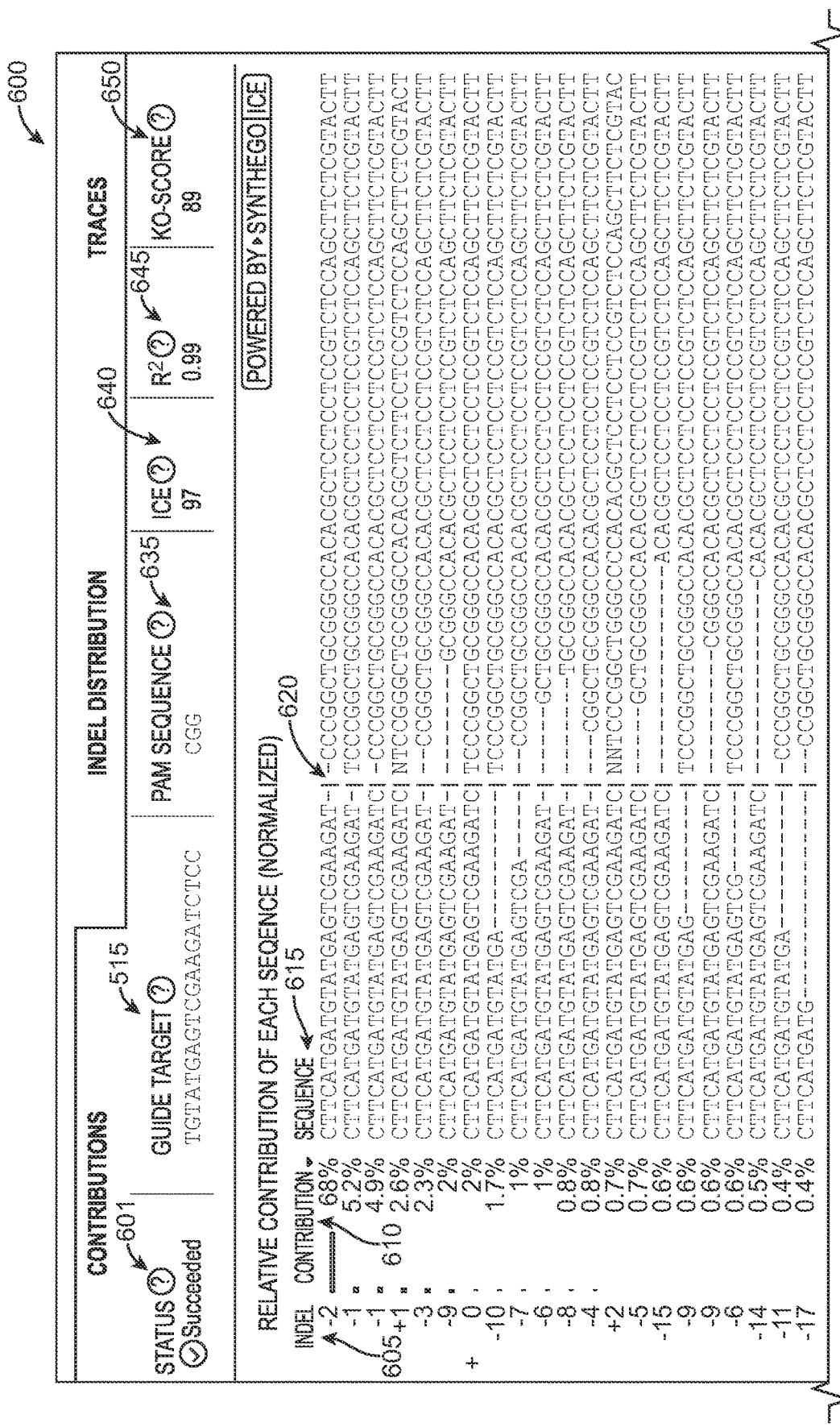
FIGS. 6A-6D illustrate examples of a window of a GUI for displaying one or more results of deducing an edit in a nucleic acid from a single guide editing.

FIG. 6A illustrates an example of a window 600 of the GUI for displaying results of deducing the mutation in the gene to the user. The window 600 can report a status 601 of the analysis, the status 601 indicating whether the analysis was successful or not. The window 600 can display each trace of the subset, as aforementioned. Information displayed for each trace of the subset can include a size 605 of the indel of the trace, a frequency (or distribution) 610 of the trace in the subset, a sequence 615 of the trace, and a relative position 620 of the cut site. In the traces of the subset, a horizontal line "-" 625 can indicate a deletion of a nucleotide, while a letter "N" 630 can indicate an insertion of a nucleotide. In some cases, the analysis method can assume a uniform distribution for each of the four nucleotides for an insertion (e.g., a uniform distribution of 25% for each nucleotide). In some cases, the window 600 can display the guide target sequence 515 that is provided by the user in the window 500. In some cases, the window 600 can display a PAM sequence 635 adjacent to the target sequence 515 in the gene. The window 600 can display an edit efficiency 640 of the gene editing tool. In some cases, when CRISPR/Cas is used as a nuclease, the edit efficiency 640 can also be referred to as Inference of CRISPR Edits (ICE). In some cases, the window 600 can display an R-squared value 645 of the regression analysis (e.g. the NNLS regression analysis or the Lasso regression analysis) used for the analysis. The R-squared 645 value can be an indication of how reliable the edit efficiency 640 can be. In some cases, the window 600 can display a knockout (KO) score 650. The KO score can indicate how many of the contributing indels can result in a functional KO of the targeted gene. In some cases, the user can be able to download 603 the analysis data.

Figure 6B:
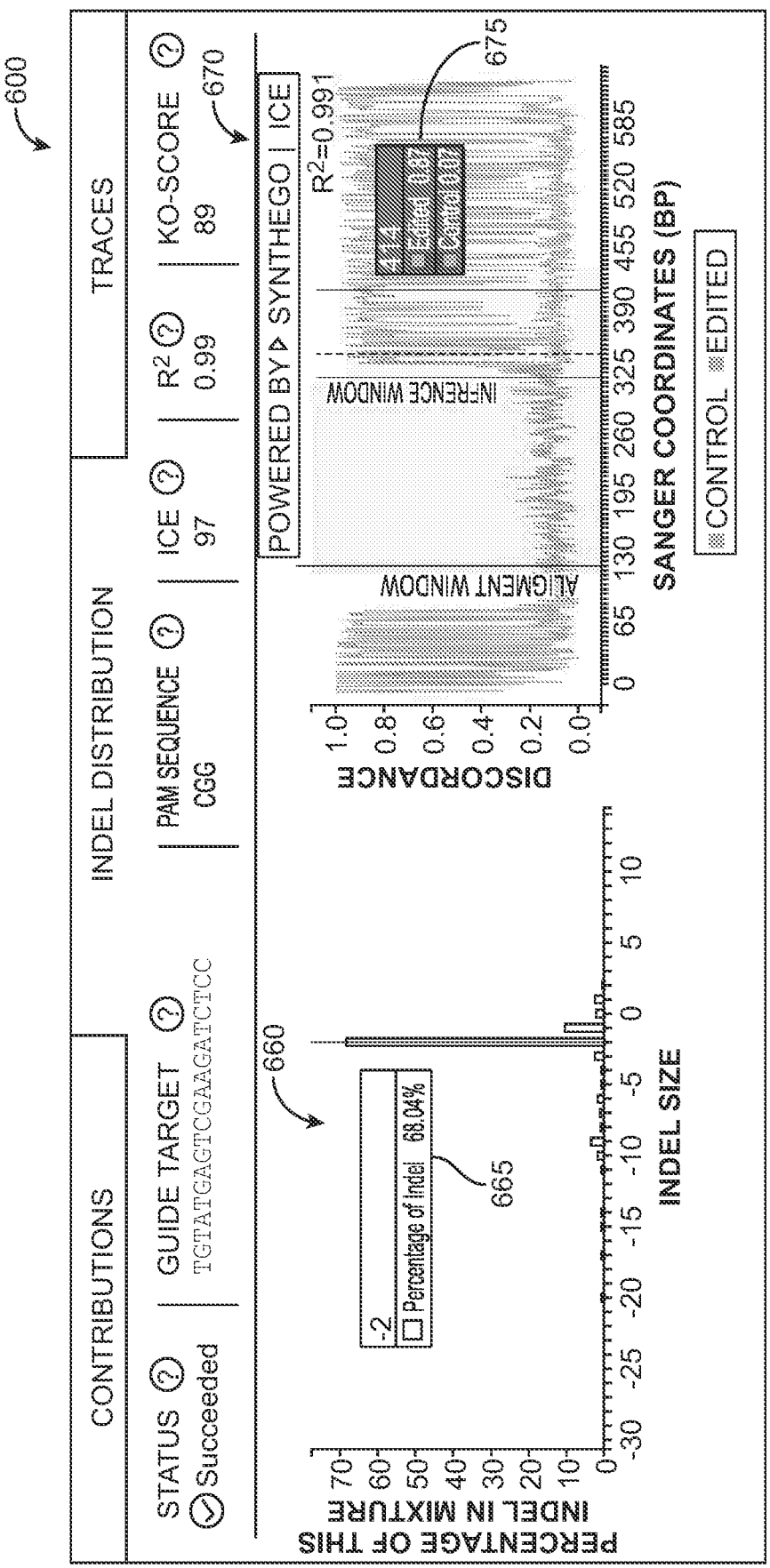

FIG. 6B illustrates another example of the window 600 of the GUI for displaying results of deducing the mutation in the gene to the user. In some cases, the window 600 can display an indel distribution plot 660 that shows an inferred distribution (frequency) of indel sizes in a population of mutated sequences that are predicted to be present (e.g., in the subset as described in the aforementioned Examples) after gene editing by the gene editing tool. The indel distribution plot 660 can be similar to the distribution plot 220. In some cases, the user can be able to select each bar in the indel distribution plot 660 to reveal additional information 665. The additional information 665 can include the size of the selected indel (e.g., + or −1 or more nucleotides), along with the percentage of the population of mutated sequences that contain the selected indel. In some cases, the window 600 can display a discordance plot 670 that shows, base-by-base, an amount of signal from that disagrees with a reference sequence derived from the non-edited, first sequencing trace. The discordance plot 670 can be similar to the discordance plot 210. In some cases, regions of the discordance plot 670 can be highlighted to indicate an alignment window and an inference window. In some cases, the user can be able to select each nucleobase position in the discordance plot 670 to reveal additional information 675. The additional information 675 can include a discordance value the control sample (e.g., the first AB1 file 505) and a discordance value of the edited sample (e.g., the second AB1 file 510) at the selected nucleobase position.

Figure 6C:
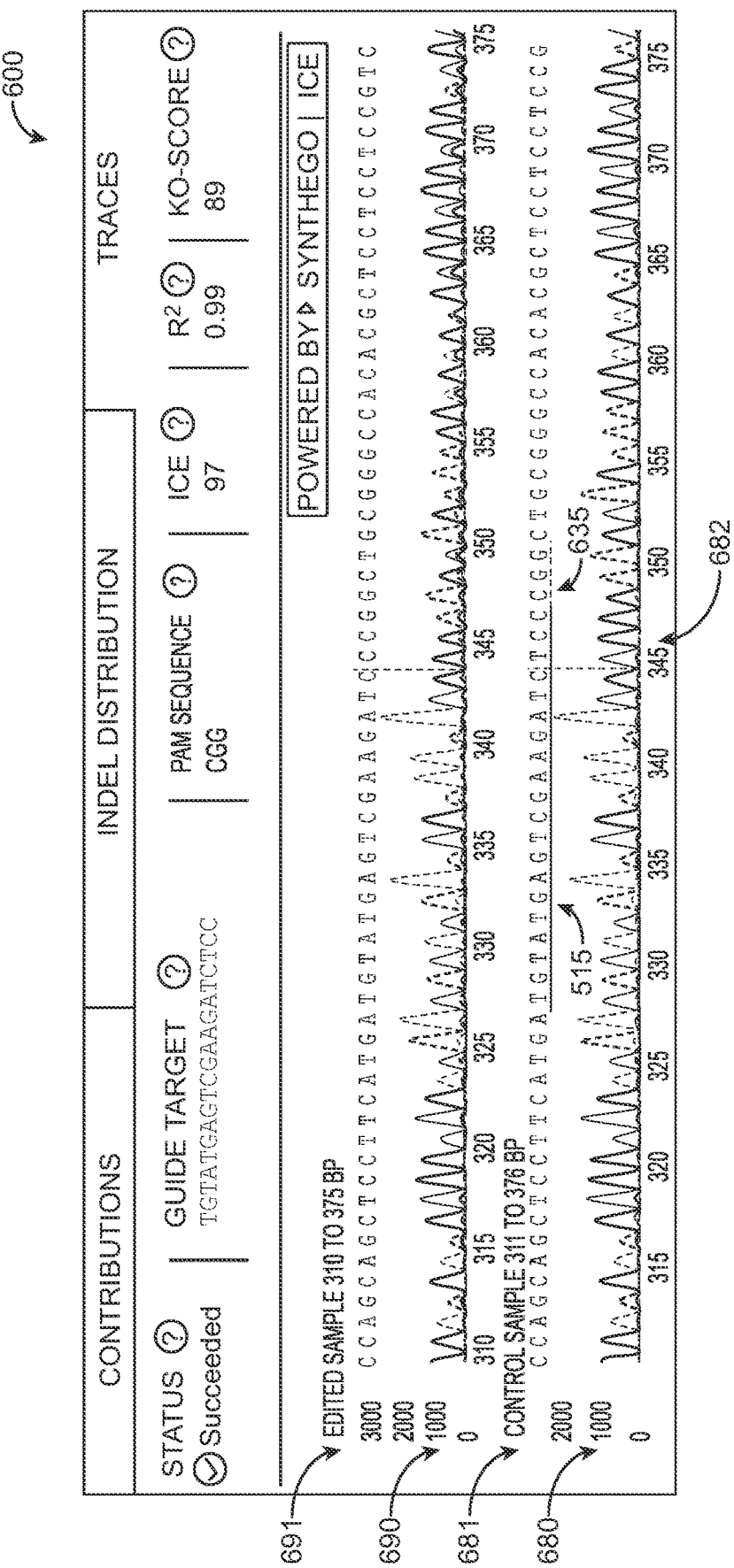

FIG. 6C illustrates another example of the window 600 of the GUI for displaying results of deducing the mutation in the gene to the user. In some cases, the window 600 can display an electropherogram 680 from the control sample (e.g., the first AB1 file 505) and an electropherogram 690 from the edited sample (e.g., the second AB1 file 510). The window 600 can display sequence base calls 681 of the electropherogram 680 and sequence base calls 691 of the electropherogram 690. The window 600 can display a position and length (indicated by a horizontal solid line) of the target sequence 515 with respect to the electropherogram 680 of the control sample. The window 600 can display a relative position of the cut site 682 (indicated by a vertical dotted line) of the target sequence 515 with respect to the electropherogram 680 of the control sample. The window 600 can indicate the PAM sequence 635 (indicated by a horizontal dotted line) adjacent to the target sequence 515.

Figure 6D:
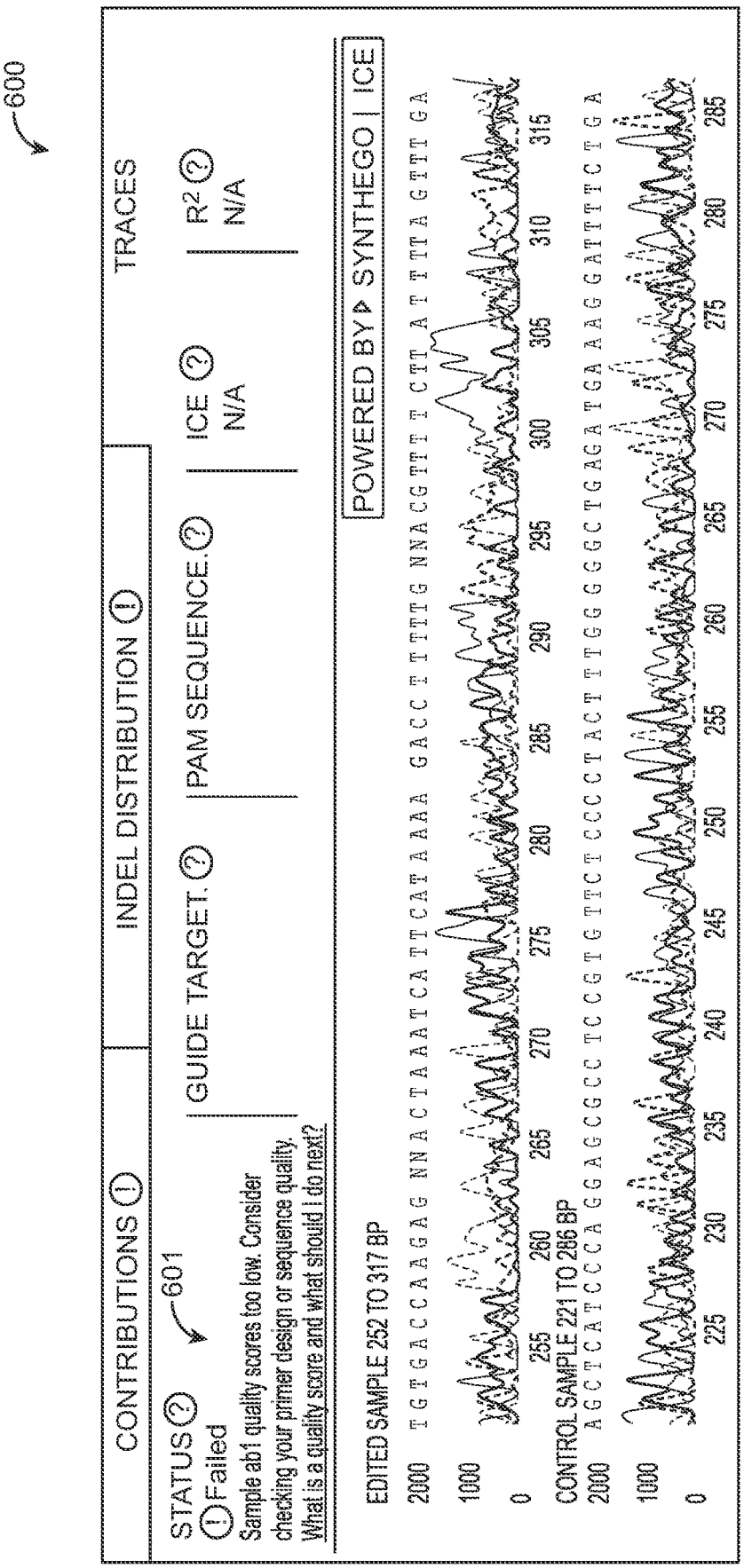

FIG. 6D illustrates another example of the window 600 of the GUI for displaying results of deducing the mutation in the gene to the user. In some cases, a quality of the sequencing traces provided by the user can be assessed prior to analysis. In some cases, a Phred score can be used to assess the quality of the sequencing traces. In some cases, an average Phred score of the sequencing traces can need to be greater than or equal to a threshold value. In some cases, the average Phred score of either or both of the sequencing traces can be lower than the threshold value, and the window 600 will display the status 601 of the analysis as "failed."

Example 8

User Interface for Multiplex Editing

Figure 7:
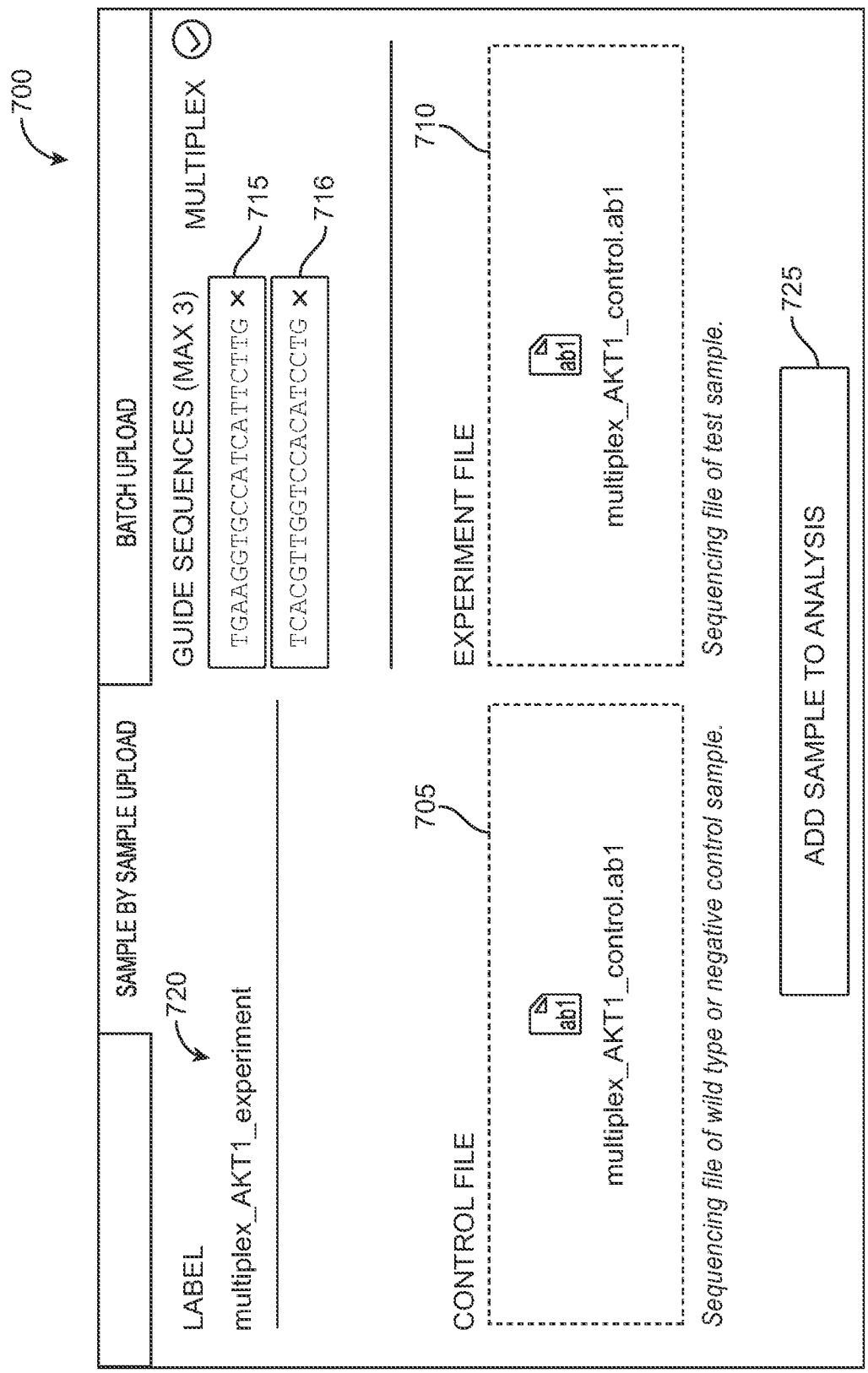
FIG. 7 illustrates an example of a window of a GUI for a user to provide sequencing files and two or more target sequences for deducing an edit in a nucleic acid from a multiplex editing.

In some cases, the user can provide two or more target sequences of the gene by the gene editing tool for analyzing multiplex editing. FIG. 7 illustrates an example of a window 700 of a graphical user interface (GUI) for the user to provide (i) a first AB1 file 705 comprising a first sequencing trace of the gene without an exposure to a gene editing tool (i.e., control file), (ii) a second AB1 file 710 comprising a second sequencing trace of the gene with an exposure to the gene editing tool (i.e., experiment file), (iii) a first target sequence 715 of the gene (i.e., guide sequence), and a different, second target sequence 716 of the gene. The first sequencing trace can be a sequencing trace of a control sample. The second sequencing trace can be a sequencing trace of an edited sample. The first and second sequencing traces of the first and second AB1 files 705 and 710, respectively, can each be a Sanger sequencing trace. In some cases, the user can designate a name 720 for the analysis of the samples provided. The window 700 of the GUI can have an option 725 for the user to initiate analysis of the samples. In some cases, such option 725 may not be available until necessary information (e.g., the files 705, 710 and the information 715, 716, and 720) have been provided and uploaded to the GUI successfully.

Figure 8A:
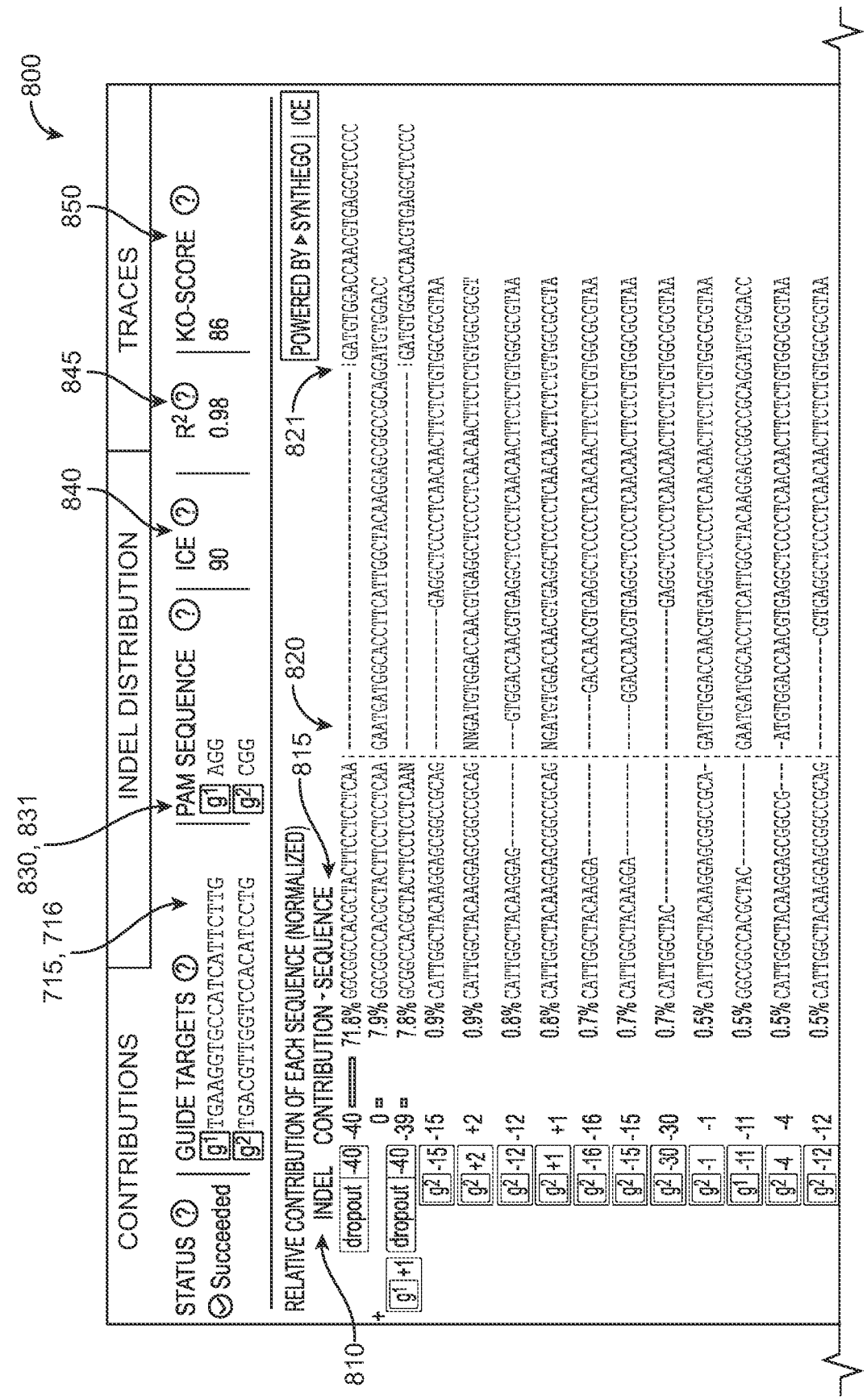
FIGS. 8A-8C illustrate examples of a window of a GUI for displaying one or more results of deducing an edit in a nucleic acid from a multiplex editing.

FIG. 8A illustrates an example of a window 800 of the GUI for displaying results of deducing the mutation in the gene from multiplex editing. The window 800 can comprise features of the window 600 of FIGS. 6A-6D. Referring to FIG. 8A, the window 800 can display each trace of a subset of an initial set comprising a plurality of predicted mutation traces, as aforementioned in the present disclosure. A linear combination of each trace of the subset can resemble the second sequencing trace from the edited sample. The window 800 can display one or more information for each trace of the subset. The one or more information can include a size 805 of the indel of the trace. Each trace can be marked 806 to indicate whether the indel was predicted based on the first target sequence 715 (marked as "g1"), the second target sequence 716 (marked as "g2"), or both. The one or more information can further include a frequency (or distribution) 810 of the trace in the subset, a sequence 815 of the trace, and a relative position of a cut site 820. In some cases, the indel of the trace can have been predicted based on an assumption that the gene was cut at both the first target sequence 715 and the second target sequence 716. In such a case, the trace can show the relative position of the cut site 820 and an additional cut site 821. In some cases, the window 800 can display the target sequences 715 and 716 that are provided by the user in the window 700. In some cases, the window 800 can display PAM sequences 830 and 831 adjacent to the target sequences 715 and 716 in the gene, respectively. The window 800 can display an edit efficiency 840 of the multiplex editing. In some cases, when CRISPR/Cas is used as a nuclease, the edit efficiency 840 can also be referred to as Inference of CRISPR Edits (ICE). In some cases, the window 800 can display an R-squared value 845 of the regression analysis (e.g. the NNLS regression analysis or the Lasso regression analysis) used for the analysis of the samples. In some cases, the window 800 can display a knockout (KO) score 850.

Figure 8B:
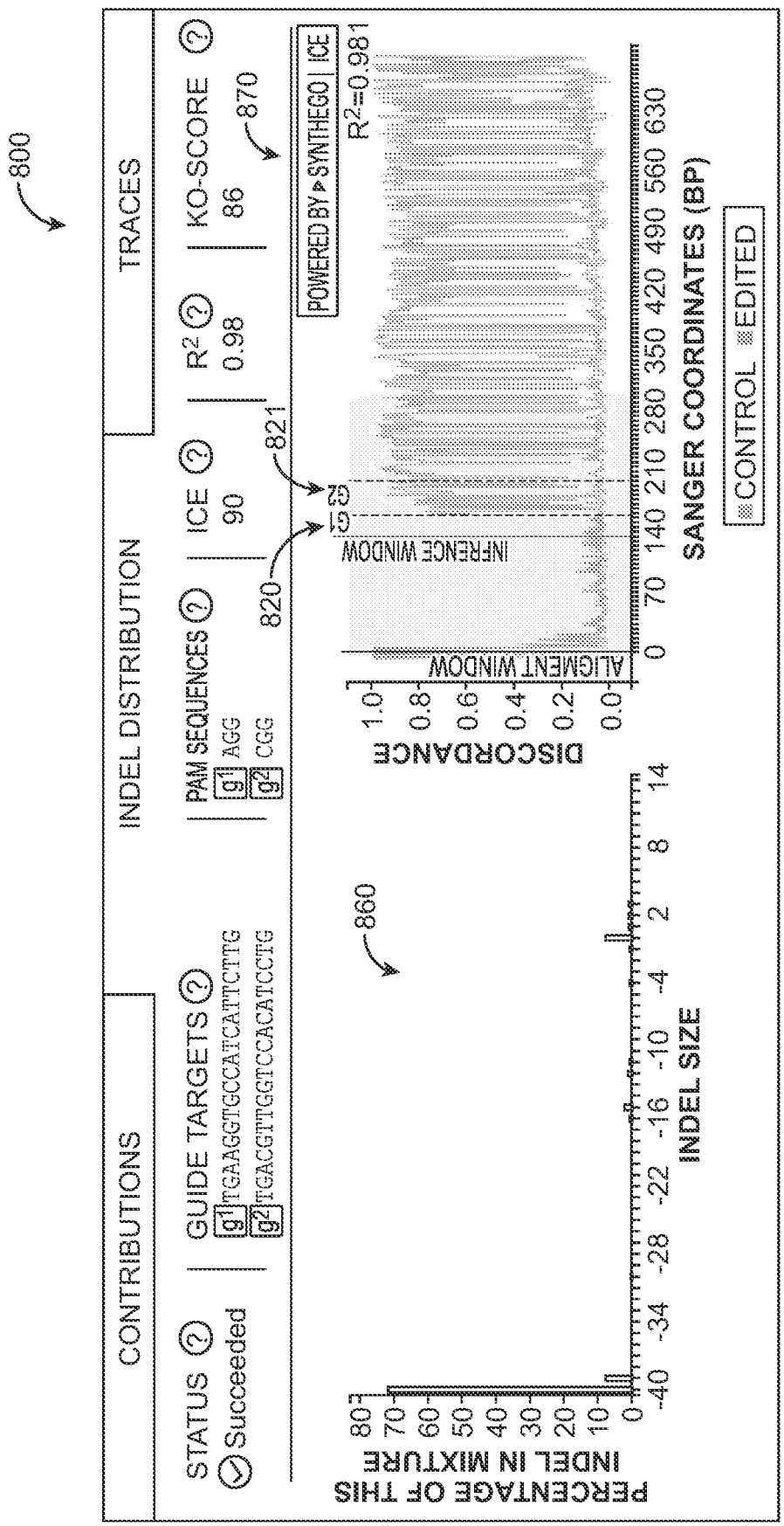

FIG. 8B illustrates another example of the window 800 of the GUI for displaying results of deducing the mutation in the gene from multiplex editing. The window 800 can display similar features that are present in the window 600 of FIG. 6B. Referring to the window 800 of FIG. 8B, examples of such features include (i) an indel distribution plot 860, which is similar to the indel distribution plot 660 of the window 600, and (ii) a discordance plot 870, which is similar to the discordance plot 670 of the window 600. In some cases, the two cut sites 820 and 821 of the multiplex editing can be indicated in the discordance plot 670.

Figure 8C:
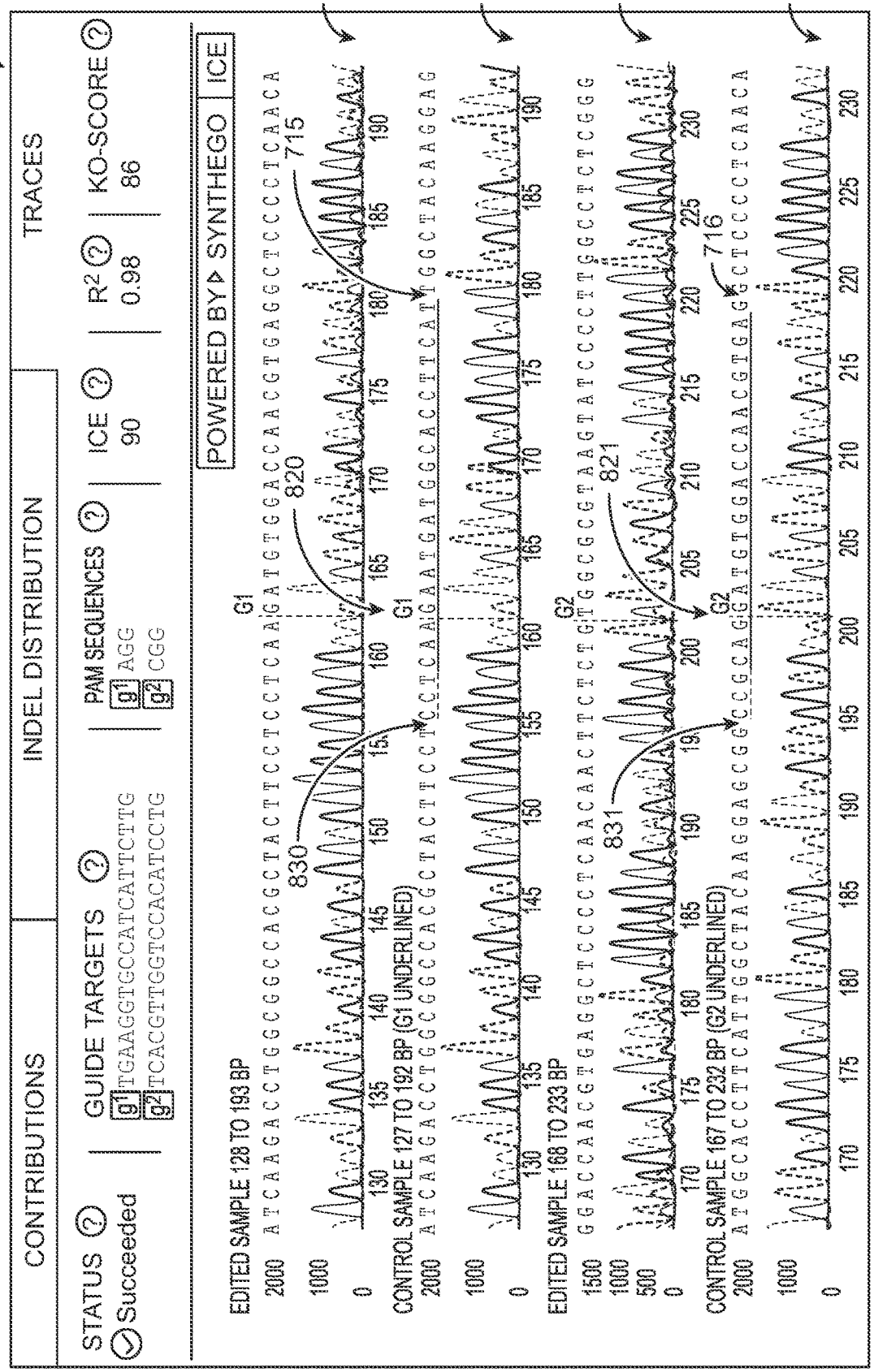

FIG. 8C illustrates another example of the window 800 of the GUI for displaying results of deducing the mutation in the gene from multiplex editing. In some cases, the window 800 can display (i) a first portion 880a of an electropherogram from the control sample (e.g., the first AB1 file 705) that is marked with a relative position of the first target sequence 715, its cut site 820, and its PAM site 820, (ii) a first portion 885a of an electropherogram from the edited sample (e.g., the second AB1 file 710), (iii) a second portion 880b of the electropherogram from the control sample that is marked with a relative position of the second target sequence 716, its cut site 821, and its PAM site 831 and (iv) a second portion 885b of the electropherogram from the edited sample. The electropherograms 880a, 880b, 885a, and 885b can display their sequence base calls.

Example 9

User Interface for Homology Directed Repair

Figure 9:
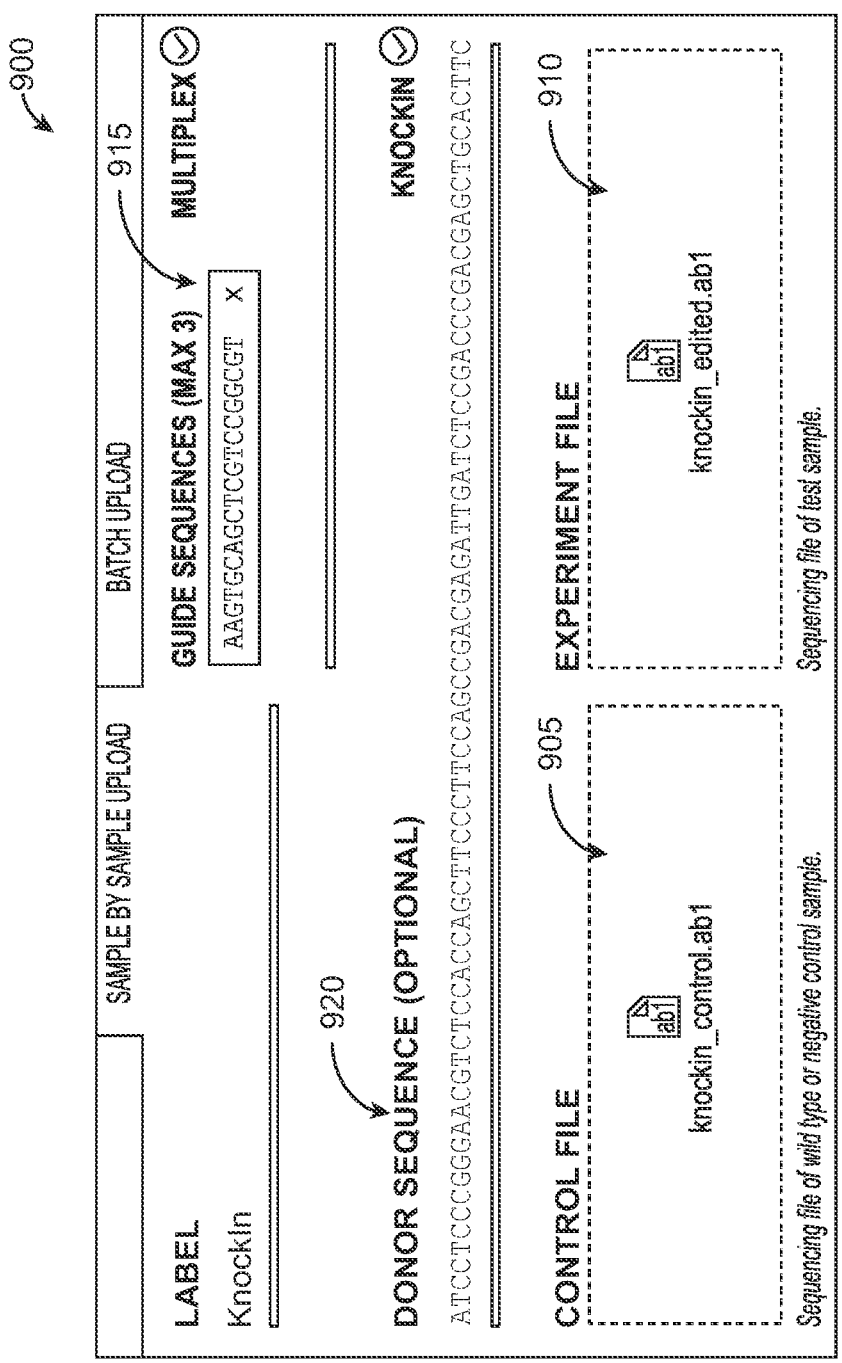
FIG. 9 illustrates an example of a window of a GUI for a user to provide sequencing file, a target sequence, and a donor sequence for deducing an edit in a nucleic acid from a nucleic acid knockin.

In some cases, the user can provide one or more target sequences of the gene by the gene editing tool and a donor sequence of HDR for analyzing gene knockin. FIG. 9 illustrates an example of a window 900 of a graphical user interface (GUI) for the user to provide (i) a first AB1 file 905 comprising a first sequencing trace of the gene without an exposure to a gene editing tool (i.e., control file), (ii) a second AB1 file 910 comprising a second sequencing trace of the gene with an exposure to the gene editing tool (i.e., experiment file), (iii) a target sequence 915 of the gene (i.e., guide sequence), and (iv) a donor sequence 920 of HDR for gene knockin. In some cases, the donor sequence 920 can include sequences of the two homology arms and a sequence to be knocked into the gene. The first sequencing trace can be a sequencing trace of a control sample. The second sequencing trace can be a sequencing trace of an edited sample. The first and second sequencing traces of the first and second AB1 files 705 and 710, respectively, can each be a Sanger sequencing trace. In some cases, the user can designate a name for the analysis of the samples provided.

Figure 10A:
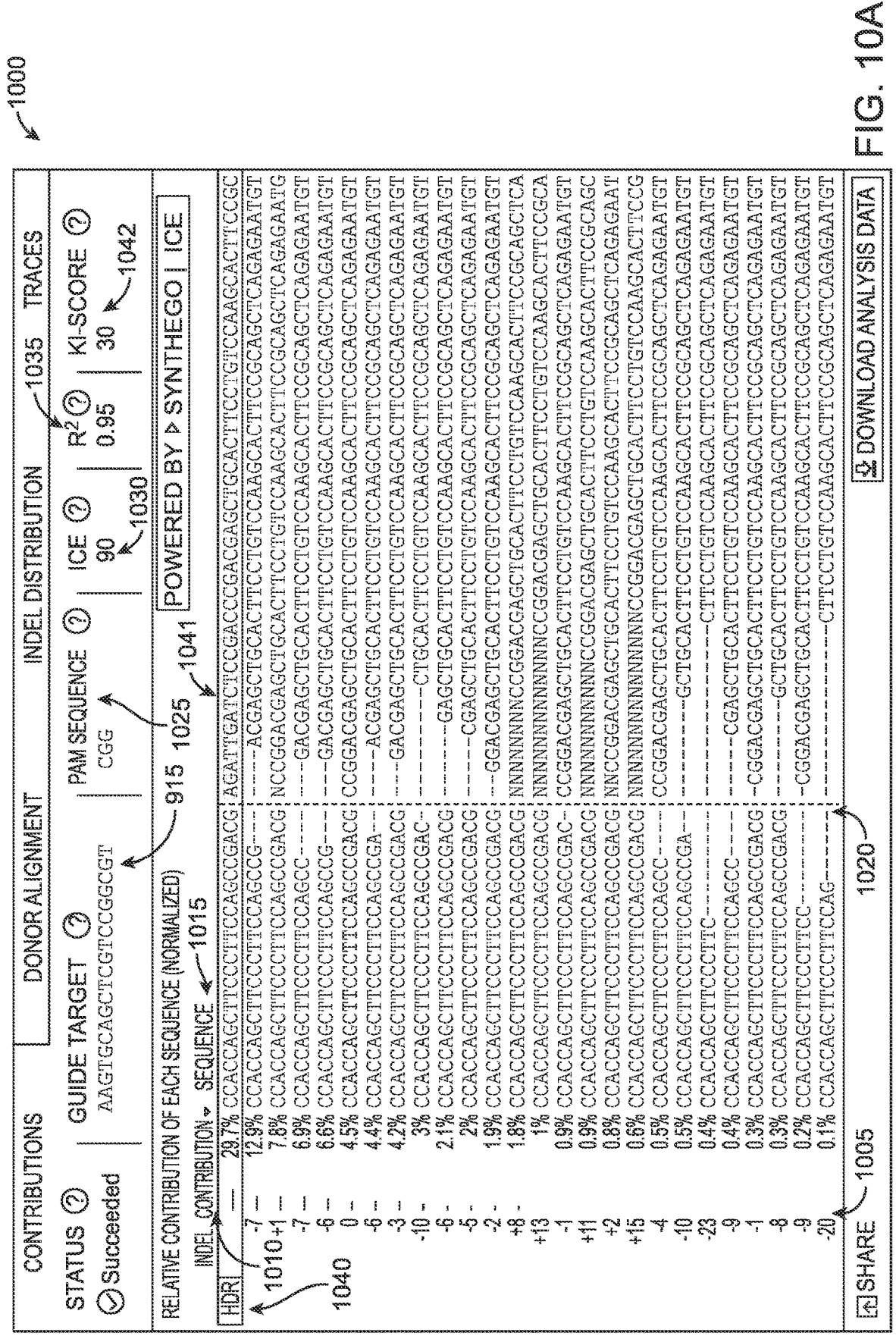
FIGS. 10A-10C illustrate examples of a window of a GUI for displaying one or more results of deducing an edit in a nucleic acid from a nucleic acid knockin.

FIG. 10A illustrates an example of a window 1000 of the GUI for displaying results of deducing the mutation in the gene for gene knockin. The window 1000 can comprise features of the window 600 of FIGS. 6A-6D. Referring to FIG. 10A, the window 1000 can display each trace of a subset of an initial set comprising a plurality of predicted mutation traces, as aforementioned in the present disclosure. A linear combination of each trace of the subset can resemble the second sequencing trace from the edited sample. The window 1000 can display one or more information for each trace of the subset. The one or more information can include a size 1005 of the indel of the trace. The one or more information can further include a frequency (or distribution) 1010 of the trace in the subset, a sequence 1015 of the trace, and a relative position of a cut site 1020. In some cases, the window 1000 can display the target sequence 915 that is provided by the user in the window 900. In some cases, the window 1000 can display a PAM sequence 1025 adjacent to the target sequence 915 in the gene. The window 1000 can display an edit efficiency 1030 of the multiplex editing. In some cases, when CRISPR/Cas is used as a nuclease, the edit efficiency 1030 can also be referred to as Inference of CRISPR Edits (ICE). In some cases, the window 1000 can display an R-squared value 1035 of the regression analysis (e.g. the NNLS regression analysis or the Lasso regression analysis) used for the analysis of the samples. In some cases, the window 1000 can indicate 1040 which of the traces shown is the HDR trace 1040 with the donor sequence. The window 1000 can also highlight the knockin sequence 1041 of the HDR trace 1040. The window 1000 can also display the HDR score 1042. In some cases, the HDR score 1042 can be referred to as a knockin (KI) score.

Figures 10B, 10C:
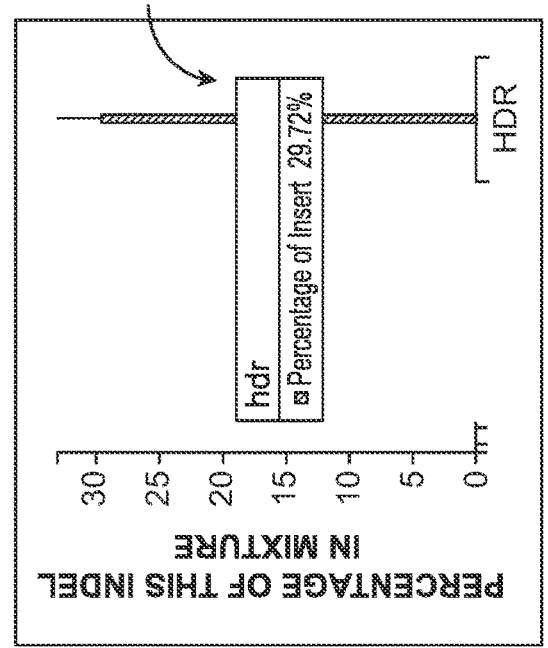

FIG. 10B illustrates another example of the window 1000 of the GUI for displaying results of deducing the mutation in the gene for gene knockin. In some cases, the window 1000 can display an alignment between the donor sequence 920 and the first sequencing trace 1050 of the control sample without the exposure to the gene editing tool. The donor sequence can comprise a first homology arm sequence 920a, a second homology arm sequence 920b that is downstream of the first homology arm sequence 920a, and a donor sequence 920c that is to be knocked into the gene and disposed between the first homology arm sequence 920a and the second homology arm sequence 920b. In some cases, the alignment between the donor sequence 920 and the first sequencing trace 1050 can be used for troubleshooting donor alignment. The alignment can visualize any mismatch between the donor sequence 920 and the first sequencing trace 1050.

FIG. 10C illustrates another example of the window 1000 of the GUI for displaying results of deducing the mutation in the gene for gene knockin. In some cases, the window 1000 can graphically show the HDR (KI) score 1042 of the HDR trace in the subset.

Example 10

User Interface for a Batch Analysis

In some cases, the user can provide a plurality of gene sequencing data sets at once for a batch analysis. In some cases, the plurality of gene sequencing data sets can comprise a data set for deducing a mutation in a gene by a gene editing tool, as illustrated in Example 7. In some cases, the plurality of gene sequencing data sets can comprise a data set for deducing a mutation in a gene from multiplex editing, as illustrated in Example 8. In some cases, the plurality of gene sequencing data sets can comprise a data set for deducing an efficiency of gene knockin, as illustrated in Example 9.

FIG. 11 illustrates an example of a window 1100 of a GUI for the user to provide (i) a first batch file 1105 (e.g., a zipped file) comprising a plurality of sequencing data sets (e.g., a plurality of AB1 files), and (ii) a second batch file 1110 (e.g., a spreadsheet file) comprising definitions of the plurality of sequencing data sets included in the first batch file 1105. FIG. 12A illustrates an example of a table 1200 comprising the plurality of sequencing data sets included in the first batch file 1005. The plurality of sequencing data sets can comprise two or more pairs of sequencing data, wherein each pair comprises (i) a control file from a cell or a population of cells without an exposure to the gene editing tool and (ii) an experimental file from the same cell or the same population of cells with an exposure to the gene editing tool. FIG. 12B illustrates an example of a spreadsheet 1210 comprising definitions of the plurality of sequencing data sets (e.g., from the table 1200) included in the second file 1110. For each data set, the spreadsheet 1210 can include a name of the analysis 1215, a name of the control file 1220, a name of the experiment file 1225, a target sequence 1230 (or guide sequence) of the gene editing tool, and, optionally, a donor sequence 1235 for HDR. In some cases, the user can provide two or more different target sequences of the gene for multiplex analysis. In some cases, the user can provide a donor sequence of HDR for gene knockin analysis.

Figure 13:
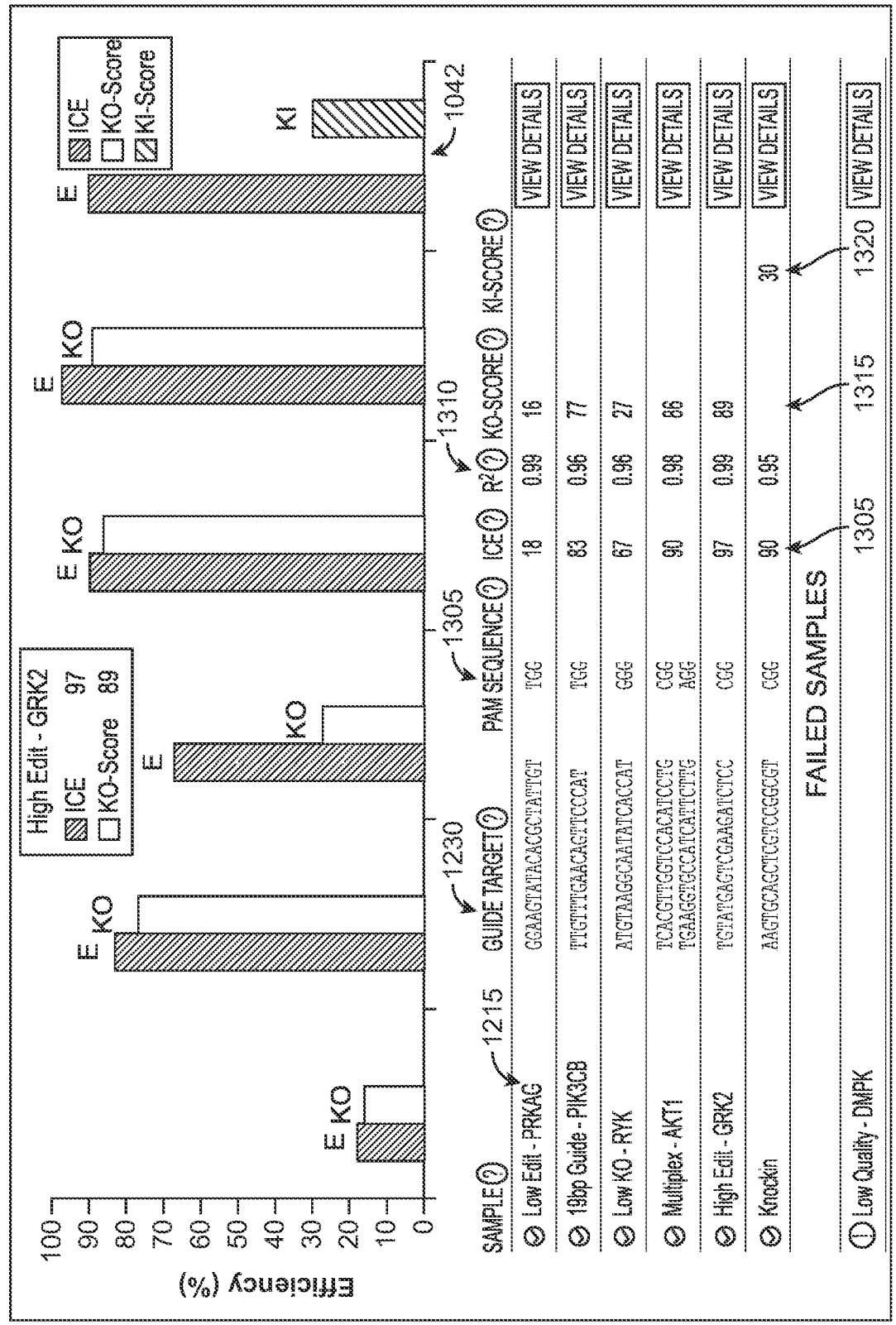
FIG. 13 illustrates an example of a window of a GUI for displaying one or more results of a batch analysis of deducing an edit in a nucleic acid.

Once the user uploads the first file 1105 and the second file 1110, one or more computer programs can automatically parse the sequencing data from the first batch file 1105 in accordance with the definitions provided in the table 1200. Following, a batch analysis of the plurality of sequencing data sets can be performed, and a summary of results can be displayed to the user. FIG. 13 illustrates an example of a summary 1300 of results from the batch analysis. In some cases, the summary 1300 can include a bar graph indicating, for each sequencing data set, an edit efficiency score (indicated by "E"), a gene knockout score (indicated by "KO"), and, optionally, a knockin score (indicated by "KI"). In some cases, the summary 1300 can include a table displaying the name of the analysis 1215, the target sequence 1230, the PAM sequence 1305 that is disposes adjacent to the target sequence 1230 in the gene, the edit efficiency score 1305, the R-squared value 1310 of the regression analysis, the gene knockout score 1315, and/or the gene knockin score 1320. In some cases, the user can select a data set of interest to be directed to a different window that displays more details on the analysis of the selected data set, such as the window 600 in FIGS. 6A-6D, the window 800 in FIGS. 8A-8C, or the window 1000 in FIGS. 10A-10C.

While preferred embodiments of the present disclosure have been shown and described herein, it will be obvious to those skilled in the art that such embodiments are provided by way of example only. It is not intended that the disclosure be limited by the specific examples provided within the specification. The descriptions and illustrations of the embodiments herein are not meant to be construed in a limiting sense. Numerous variations, changes, and substitutions will now occur to those skilled in the art without departing from the invention. Furthermore, it shall be understood that all aspects of the disclosure are not limited to the specific depictions, configurations or relative proportions set forth herein which depend upon a variety of conditions and variables. It should be understood that various alternatives to the embodiments of the disclosure described herein can be employed in practicing the disclosure. It is therefore contemplated that the disclosure shall also cover any such alternatives, modifications, variations or equivalents. It is intended that the following claims define the scope of the invention and that methods and structures within the scope of these claims and their equivalents be covered thereby.

What is claimed is:

1. A method comprising:
   determining, by a computer system, a plurality of predicted sequences of individual nucleic acid molecules in a sample,
   wherein the sample has been contacted by at least two different nucleic acid editing tools, and
   wherein the determining is based on a Sanger sequencing trace of a plurality of nucleic acid molecules from the sample that has been contacted by the at least two different nucleic acid editing tools;
   assessing, by the computer system, an outcome of contacting the sample with the at least two different nucleic acid tools based on determining the plurality of predicted sequences; and
   reporting, by the computer system, a predicted knockout sequence to a user.

2. The method of claim 1, wherein the determining is further based on an additional Sanger sequencing trace of a plurality of nucleic acid molecules from an additional sample not contacted by a nucleic acid editing tool.

3. The method of claim 2, wherein the determining is further based on at least two different guide sequences of the at least two different nucleic acid editing tools.

4. The method of claim 3, further comprising determining a base trace by trimming the additional Sanger sequencing trace based on the at least two different guide sequences.

5. The method of claim 4, wherein the trimming comprises subtracting a portion of the additional Sanger sequencing trace disposed between (i) a predicted cut site operatively coupled to a first guide sequence of the at least two different guide sequences and (ii) an additional predicted cut site operatively coupled to a second guide sequence of the at least two different guide sequences.

6. The method of claim 5, wherein an individual predicted sequence of the plurality of predicted sequences comprises an insertion or a deletion adjacent to (i) the predicted cut site or (ii) the additional predicted cut site.

7. The method of claim 4, further comprising identifying a subset of the plurality of predicted sequences by performing a regression analysis.

8. The method of claim 7, wherein the regression analysis comprises a non-negative least squares regression analysis or a regularized regression analysis.

9. The method of claim 7, wherein an R-squared value of the regression analysis is at least 0.5, 0.55, 0.6, 0.65, 0.7, 0.75, 0.8, 0.85, 0.9, or 0.95.

10. The method of claim 7, further comprising reporting to a user a predicted sequence of the subset and a frequency of the predicted sequence in the subset.

11. The method of claim 7, wherein the regression analysis comprises a Lasso regression analysis.

12. The method of claim 1, wherein an individual nucleic acid editing tool of the at least two different nucleic acid editing tools comprises a nuclease system.

13. The method of claim 12, wherein the nuclease system comprises a CRISPR/Cas system.

14. The method of claim 1, wherein assessing the outcome comprises determining an editing efficiency.

15. A method comprising:
   determining, by a computer system, a predicted knockout sequence of a single nucleic acid molecule based on a first Sanger sequencing trace and a second Sanger sequencing trace,
   wherein the predicted knockout sequence comprises an indel when compared to the second Sanger sequencing trace; and
   reporting, by the computer system, the predicted knockout sequence to a user.

16. The method of claim 15, wherein the indel of the predicted knockout sequence yields a stop codon.

17. The method of claim 15, wherein the indel of the predicted knockout sequence is not a multiple of three nucleotides and/or longer than a threshold length.

18. A method comprising:
   determining, by a computer system, a first predicted sequence of a single nucleic acid molecule and a second predicted sequence of a single nucleic acid molecule,
   wherein the first and second predicted sequences are based on a first Sanger sequencing trace of a first plurality of nucleic acid molecules from a first sample,
   wherein the first and second predicted sequences each comprises an indel when compared to a second Sanger sequencing trace of a second plurality of nucleic acid molecules from a second sample, and
   wherein the indels of the first and second predicted sequences have a same size and a different nucleic acid sequence; and
   reporting, by the computer system, the first predicted sequence and the second predicted sequence to a user.

* * * * *